US012571040B2

(12) United States Patent
Stengel et al.

(10) Patent No.: US 12,571,040 B2
(45) Date of Patent: Mar. 10, 2026

(54) CHROMATIN PROFILING COMPOSITIONS AND METHODS

(71) Applicant: ALIDA BIOSCIENCES, INC., San Diego, CA (US)

(72) Inventors: Gudrun Stengel, San Diego, CA (US); Hua Yu, San Diego, CA (US); Byron Purse, San Diego, CA (US)

(73) Assignee: ALIDA BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 19/212,398

(22) Filed: May 19, 2025

(65) Prior Publication Data

US 2025/0277266 A1     Sep. 4, 2025

Related U.S. Application Data

(63) Continuation of application No. PCT/US2023/081014, filed on Nov. 22, 2023.

(60) Provisional application No. 63/427,759, filed on Nov. 23, 2022.

(51) Int. Cl.
| | |
|---|---|
| *C12Q 1/6874* | (2018.01) |
| *C12Q 1/6806* | (2018.01) |
| *C12Q 1/6855* | (2018.01) |

(52) U.S. Cl.
CPC ......... *C12Q 1/6874* (2013.01); *C12Q 1/6806* (2013.01); *C12Q 1/6855* (2013.01)

(58) Field of Classification Search
CPC ... C12Q 1/6874; C12Q 1/6806; C12Q 1/6855
See application file for complete search history.

(56) References Cited

U.S. PATENT DOCUMENTS 10,655,162 B1     5/2020  Goren

FOREIGN PATENT DOCUMENTS

| | | |
|---|---|---|
| EP | 2 783 001 B1 | 1/2018 |
| WO | 2016/011364 A1 | 1/2016 |
| WO | 2018/031897 A1 | 2/2018 |
| WO | 2018/204854 A1 | 11/2018 |
| WO | 2020/072829 A2 | 4/2020 |
| WO | WO-2022094449 A1 * | 5/2022 ............... C12Q 1/68 |
| WO | WO-2022115608 A1 * | 6/2022 ........... C12Q 1/6804 |

OTHER PUBLICATIONS

Ungerer et al., Nature Scientific Reports, 11, 9460, 1-20 (Year: 2021).*
International Search Report and Written Opinion dated Mar. 18, 2024 issued in International Patent Application PCT/US2023/081014. (14 pages).
Gopalan, Sneha et al; "Simultaneous profiling of multiple chromatin proteins in the same cells", Molecular Cell; vol. 81, Nov. 18, 2021; pp. 4736-4746 (17 pages).
Carter, Benjamin et al; "Mapping histone modifications in low cell number and single cells using antibody-guided chromatin tagmentation (ACT-seq)", Nature Communications, vol. 10, No. 1, (2019) (5 pages).
Sadeh, Ronen et al; "Elucidating Combinatorial Chromatin States at Single-Nucleosome Resolution", Molecular Cell; vol. 63, Sep. 15, 2016; pp. 1080-1088 (10 pages).
Zhu, Chenxu et al; "Joint profiling of histone modifications and transcriptome in single cells from mouse brain", nature methods, vol. 18, Mar. 2021; pp. 283-292 (24 pages).
Ohnuki, Hidetaka et al; "Iterative epigenomic analyses in the same single cell", Genome Research, vol. 31, Feb. 24, 2021 (Feb. 24, 2021); pp. 1819-1830 (13 pages).

* cited by examiner

*Primary Examiner* — Cynthia B Wilder
(74) *Attorney, Agent, or Firm* — ROTHWELL, FIGG, ERNST & MANBECK, P.C.

(57)                    ABSTRACT

Compositions and methods for single reaction and multi-plexed profiling of histone modifications. Compositions include a binding domain and adaptor or a nucleosome binding conjugate comprising a binding domain conjugated to an adapter. Methods include analyzing a plurality of nucleosomes comprising (i) contacting a plurality of sub-strates comprising a binding domain and adaptor composition with a solution comprising the plurality of nucleosomes, wherein a nucleosome comprising a histone modification or DNA binding protein binds to the binding domain; (ii) ligating an adapter with the nucleic acid barcode to the target DNA of the nucleosome comprising the histone modification or DNA binding protein; (iii) introducing universal sequences for amplifying the target DNA; (iv) amplifying the barcoded target DNA; and (v) analyzing the amplified barcoded target DNA by sequencing.

30 Claims, 27 Drawing Sheets

Specification includes a Sequence Listing.

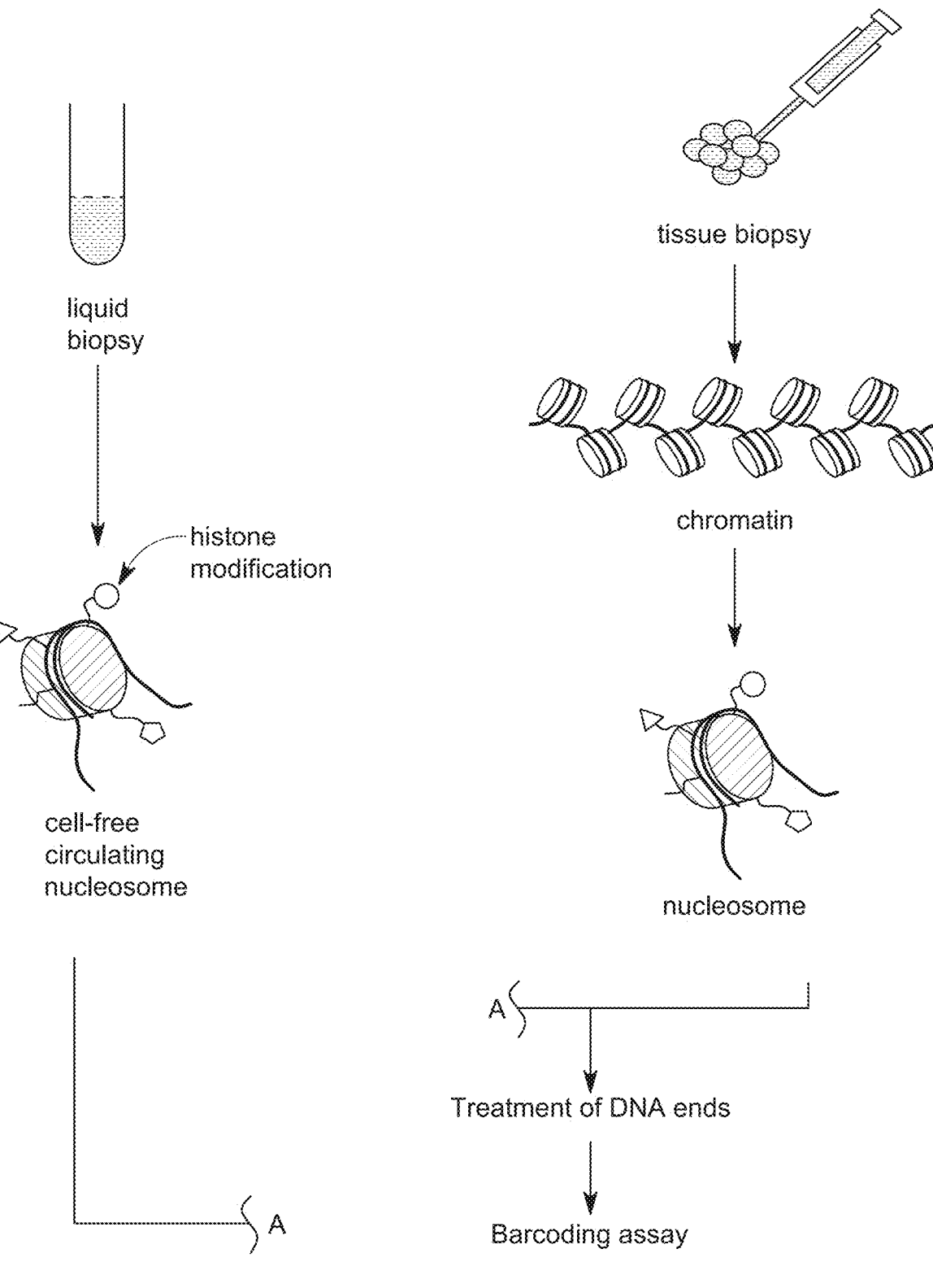
FIG. 1A                    FIG. 1B

| Gel lane | Description |
|---|---|
| M | E-Gel™ 50 bp DNA Ladder |
| 1 | IP library. Library barcoded for the histone modifications H3K4me3 and H3K4me2. |
| 2 | INPUT control library |

| Nucleosome | Clipped MBC109 | Clipped UMI | Basecall after clipping |
|---|---|---|---|
| KmetStat_H3K4me3_A | CTCTCGT | CGCGT | TCTGAGACTACCGTGAAACGCGTATCGCGCGCAAATAGCTCAATTGGTCGT AGCAAG |
| KmetStat_H3K4me3_A | CTCTCGT | GATTA | TGTAAACTACCGTGAAACGCGTATCGCGCGCATAATAGCTCAATTGGTCGT AGCAAG |
| KmetStat_H3K4me3_A | CTCTCGT | CTGGG | TTAATTACTACCGTGAAACGCGTATCGCGCGCATAATAGCTCAATTGGTCGT AGCAAG |
| KmetStat_H3K4me3_A | CTCTCGT | AATTA | TATTTAACTACCGTGAAACGCGTATCGCGCGCATAATAGCTCAATTGGTCGT AGCAAG |
| KmetStat_H3K4me3_A | CTCTCGT | AACTT | TTTCGGACTACCGTGAAACGCGTATCGCGCGCATAATAGCTCAATTGGTCGT AGCAAG |
| KmetStat_H3K4me3_A | CTCTCGT | CACTG | TTTTTAACTACCGTGAAACGCGTATCGCGCGCATAATAGCTCAATTGGTCGT AGCAAG |
| KmetStat_H3K4me3_A | CTCTCGT | AGTTA | TGATATACTACCGTGAAACGCGTATCGCGCGCATAATAGCTCAATTGGTCGT AGCAAG |
| KmetStat_H3K4me3_A | CTCTCGT | CGGGG | TTAATTACTACCGTGAAACGCGTATCGCGCGCATAATAGCTCAATTGGTCG TAGCAAG |
| KmetStat_H3K4me3_A | CTCTCGT | GTTTA | TAGGGGGACTACCGTGAAACGCGTATCGCGCGGAATAATAGCTCAATTGGTCGT AGCA |
| KmetStat_H3K4me3_A | CTCTCGT | ACTTA | TGAGTATATACTACCGTGAAACGCGTATCGCGCGCATAATAGCTCAATTGGTC GTAGCA |
| KmetStat_H3K4me3_A | CTCTCGT | CACTG | TTTTTAACTACCGTGAAACGCGTATCGCGCGCATAATAGCTCAATTGGTCG TAGCAAG |
| KmetStat_H3K4me3_A | CTCTCGT | CTTGG | TTAATTACTACCGTGAAACGCGTATCGCGCGCATAATAGCTCAATTGGTCG TAGCAAG |
| KmetStat_H3K4me3_A | CTCTCGT | AACTA | TTTCGGACTACCGTGAAACGCGTATCGCGCGCATAATAGCTCAATTGGTCGT AGCAAG |

FIG. 13C

| Gel lane | Description | Library conc. (ng/µL) |
|---|---|---|
| M | E-Gel™ 50 bp DNA Ladder | |
| 1 | No elution control | 54.0 |
| 2 | Serial IP.Elution by H3K9ac peptide. | 13.2 |
| 3 | Remaining bead bound nucleosomes after elution by H3K9ac peptide. | 37.7 |
| 4 | Serial IP.Elution by protein G. | 3.3 |
| 5 | Remaining bead bound nucleosomes after elution by peotein G. | 52.0 |
| 6 | Serial IP.Elution by gentle elution buffer. | 18.1 |
| 7 | Remaining bead bound nucleosomes after elution by gentle elution buffer. | 0.9 |

FIG. 14

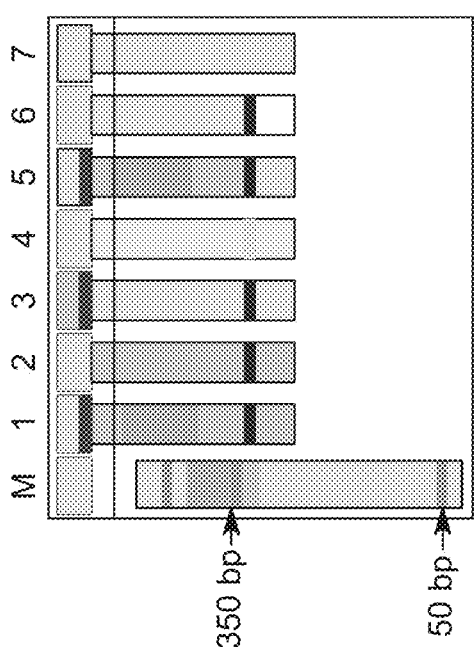

SEQUENCE LISTING

```
Sequence total quantity: 89
SEQ ID NO: 1          moltype = DNA  length = 40
FEATURE               Location/Qualifiers
source                1..40
                      mol_type = other DNA
                      organism = synthetic construct
modified_base         35
                      mod_base = OTHER
```

```
                              note = uracil
SEQUENCE: 1
gtgatcgnnn nnctgtctct tatacacatc tgactttttt                                40

SEQ ID NO: 2          moltype = DNA   length = 40
FEATURE               Location/Qualifiers
source                1..40
                      mol_type = other DNA
                      organism = synthetic construct
modified_base         35
                      mod_base = OTHER
                      note = uracil
SEQUENCE: 2
ccgcattnnn nnctgtctct tatacacatc tgactttttt                                40

SEQ ID NO: 3          moltype = DNA   length = 22
FEATURE               Location/Qualifiers
source                1..22
                      mol_type = other DNA
                      organism = synthetic construct
SEQUENCE: 3
gtcagatgtg tataagagac ag                                                   22

SEQ ID NO: 4          moltype = DNA   length = 21
FEATURE               Location/Qualifiers
source                1..21
                      mol_type = other DNA
                      organism = synthetic construct
SEQUENCE: 4
agacgtgtgc tcttccgatc t                                                    21

SEQ ID NO: 5          moltype = DNA   length = 12
FEATURE               Location/Qualifiers
source                1..12
                      mol_type = other DNA
                      organism = synthetic construct
SEQUENCE: 5
gatcggaaga gc                                                              12

SEQ ID NO: 6          moltype = DNA   length = 20
FEATURE               Location/Qualifiers
source                1..20
                      mol_type = other DNA
                      organism = synthetic construct
modified_base         19
                      mod_base = OTHER
                      note = phosphorothioate base
SEQUENCE: 6
ttaattaagc atcgatcact                                                      20

SEQ ID NO: 7          moltype = DNA   length = 19
FEATURE               Location/Qualifiers
source                1..19
                      mol_type = other DNA
                      organism = synthetic construct
SEQUENCE: 7
gtgatcgatg cttaattaa                                                       19

SEQ ID NO: 8          moltype = DNA   length = 17
FEATURE               Location/Qualifiers
source                1..17
                      mol_type = other DNA
                      organism = synthetic construct
modified_base         15..16
                      mod_base = OTHER
                      note = phosphorothioate base
SEQUENCE: 8
ttaattaatg cattcat                                                         17

SEQ ID NO: 9          moltype = DNA   length = 15
FEATURE               Location/Qualifiers
source                1..15
                      mol_type = other DNA
                      organism = synthetic construct
SEQUENCE: 9
gaattgctta attaa                                                           15

SEQ ID NO: 10         moltype = DNA   length = 26
FEATURE               Location/Qualifiers
```

-continued

```
source                  1..26
                        mol_type = other DNA
                        organism = synthetic construct
modified_base           21
                        mod_base = OTHER
                        note = uracil
SEQUENCE: 10
gatcggaaga gcacacgtct tttttt                                        26

SEQ ID NO: 11           moltype = DNA   length = 21
FEATURE                 Location/Qualifiers
source                  1..21
                        mol_type = other DNA
                        organism = synthetic construct
modified_base           20
                        mod_base = OTHER
                        note = phosphorothioate base
SEQUENCE: 11
agacgtgtgc tcttccgatc t                                             21

SEQ ID NO: 12           moltype = DNA   length = 24
FEATURE                 Location/Qualifiers
source                  1..24
                        mol_type = other DNA
                        organism = synthetic construct
modified_base           22..23
                        mod_base = OTHER
                        note = phosphorothioate base
SEQUENCE: 12
ctacacgacg ctcttccgat ctat                                          24

SEQ ID NO: 13           moltype = DNA   length = 22
FEATURE                 Location/Qualifiers
source                  1..22
                        mol_type = other DNA
                        organism = synthetic construct
SEQUENCE: 13
agatcggaag agcgtcgtgt ag                                            22

SEQ ID NO: 14           moltype = DNA   length = 21
FEATURE                 Location/Qualifiers
source                  1..21
                        mol_type = other DNA
                        organism = synthetic construct
modified_base           8
                        mod_base = OTHER
                        note = uracil
SEQUENCE: 14
cggtagttnn nnnactaccg t                                             21

SEQ ID NO: 15           moltype = DNA   length = 21
FEATURE                 Location/Qualifiers
source                  1..21
                        mol_type = other DNA
                        organism = synthetic construct
modified_base           8
                        mod_base = OTHER
                        note = uracil
SEQUENCE: 15
acgagagtnn nnnctctcgt t                                             21

SEQ ID NO: 16           moltype = DNA   length = 42
FEATURE                 Location/Qualifiers
source                  1..42
                        mol_type = other DNA
                        organism = synthetic construct
modified_base           21
                        mod_base = OTHER
                        note = uracil
SEQUENCE: 16
gatcggaaga gcacacgtct ttacacgacg ctcttccgat ct                     42

SEQ ID NO: 17           moltype = DNA   length = 19
FEATURE                 Location/Qualifiers
source                  1..19
                        mol_type = other DNA
                        organism = synthetic construct
SEQUENCE: 17
ggaaacagct atgaccatg                                                19
```

```
SEQ ID NO: 18                 moltype = DNA   length = 18
FEATURE                       Location/Qualifiers
source                        1..18
                              mol_type = other DNA
                              organism = synthetic construct
SEQUENCE: 18
ggttttccca gtcacgac                                                   18

SEQ ID NO: 19                 moltype = DNA   length = 18
FEATURE                       Location/Qualifiers
source                        1..18
                              mol_type = other DNA
                              organism = synthetic construct
SEQUENCE: 19
gtaaaacgac ggccagtg                                                   18

SEQ ID NO: 20                 moltype = DNA   length = 18
FEATURE                       Location/Qualifiers
source                        1..18
                              mol_type = other DNA
                              organism = synthetic construct
SEQUENCE: 20
tgtaaaacga cggccagt                                                   18

SEQ ID NO: 21                 moltype = DNA   length = 20
FEATURE                       Location/Qualifiers
source                        1..20
                              mol_type = other DNA
                              organism = synthetic construct
SEQUENCE: 21
agcggataac aatttcacac                                                 20

SEQ ID NO: 22                 moltype = DNA   length = 22
FEATURE                       Location/Qualifiers
source                        1..22
                              mol_type = other DNA
                              organism = synthetic construct
SEQUENCE: 22
tacgatttag gtgacactat ag                                              22

SEQ ID NO: 23                 moltype = DNA   length = 20
FEATURE                       Location/Qualifiers
source                        1..20
                              mol_type = other DNA
                              organism = synthetic construct
SEQUENCE: 23
caattaaccc tcactaaagg                                                 20

SEQ ID NO: 24                 moltype = DNA   length = 20
FEATURE                       Location/Qualifiers
source                        1..20
                              mol_type = other DNA
                              organism = synthetic construct
SEQUENCE: 24
taatacgact cactataggg                                                 20

SEQ ID NO: 25                 moltype = DNA   length = 22
FEATURE                       Location/Qualifiers
source                        1..22
                              mol_type = other DNA
                              organism = synthetic construct
SEQUENCE: 25
atgtcgtaat aaccccgccc cg                                              22

SEQ ID NO: 26                 moltype = DNA   length = 20
FEATURE                       Location/Qualifiers
source                        1..20
                              mol_type = other DNA
                              organism = synthetic construct
SEQUENCE: 26
tagttattgc tcagcggtgg                                                 20

SEQ ID NO: 27                 moltype = DNA   length = 19
FEATURE                       Location/Qualifiers
source                        1..19
                              mol_type = other DNA
                              organism = synthetic construct
SEQUENCE: 27
```

-continued

```
gctagttatt gctcagcgg                                                            19

SEQ ID NO: 28          moltype = DNA   length = 17
FEATURE                Location/Qualifiers
source                 1..17
                       mol_type = other DNA
                       organism = synthetic construct
SEQUENCE: 28
tcgaggtcga cggtatc                                                              17

SEQ ID NO: 29          moltype = DNA   length = 20
FEATURE                Location/Qualifiers
source                 1..20
                       mol_type = other DNA
                       organism = synthetic construct
SEQUENCE: 29
cgctctagaa ctagtggatc                                                           20

SEQ ID NO: 30          moltype = DNA   length = 23
FEATURE                Location/Qualifiers
source                 1..23
                       mol_type = other DNA
                       organism = synthetic construct
SEQUENCE: 30
ccgggagctg catgtgtcag agg                                                       23

SEQ ID NO: 31          moltype = DNA   length = 23
FEATURE                Location/Qualifiers
source                 1..23
                       mol_type = other DNA
                       organism = synthetic construct
SEQUENCE: 31
gggctggcaa gccacgtttg gtg                                                       23

SEQ ID NO: 32          moltype = DNA   length = 20
FEATURE                Location/Qualifiers
source                 1..20
                       mol_type = other DNA
                       organism = synthetic construct
SEQUENCE: 32
acccaatgtg cctggatgcg                                                           20

SEQ ID NO: 33          moltype = DNA   length = 21
FEATURE                Location/Qualifiers
source                 1..21
                       mol_type = other DNA
                       organism = synthetic construct
SEQUENCE: 33
gaggtatata ttaatgtatc g                                                         21

SEQ ID NO: 34          moltype = DNA   length = 18
FEATURE                Location/Qualifiers
source                 1..18
                       mol_type = other DNA
                       organism = synthetic construct
SEQUENCE: 34
gatttaatct gtatcagg                                                             18

SEQ ID NO: 35          moltype = DNA   length = 21
FEATURE                Location/Qualifiers
source                 1..21
                       mol_type = other DNA
                       organism = synthetic construct
SEQUENCE: 35
cgcaaatggg cggtaggcgt g                                                         21

SEQ ID NO: 36          moltype = DNA   length = 20
FEATURE                Location/Qualifiers
source                 1..20
                       mol_type = other DNA
                       organism = synthetic construct
SEQUENCE: 36
agtaggaaag tcccgtaagg                                                           20

SEQ ID NO: 37          moltype = DNA   length = 22
FEATURE                Location/Qualifiers
source                 1..22
                       mol_type = other DNA
                       organism = synthetic construct
```

-continued

```
SEQUENCE: 37
catggtcctg ctggagttcg tg                                                     22

SEQ ID NO: 38          moltype = DNA   length = 21
FEATURE                Location/Qualifiers
source                 1..21
                       mol_type = other DNA
                       organism = synthetic construct
SEQUENCE: 38
cgtcgccgtc cagctcgacc a                                                      21

SEQ ID NO: 39          moltype = DNA   length = 18
FEATURE                Location/Qualifiers
source                 1..18
                       mol_type = other DNA
                       organism = synthetic construct
SEQUENCE: 39
tagaaggcac agtcgagg                                                          18

SEQ ID NO: 40          moltype = DNA   length = 18
FEATURE                Location/Qualifiers
source                 1..18
                       mol_type = other DNA
                       organism = synthetic construct
SEQUENCE: 40
cccgaaaagt gccacctg                                                          18

SEQ ID NO: 41          moltype = DNA   length = 19
FEATURE                Location/Qualifiers
source                 1..19
                       mol_type = other DNA
                       organism = synthetic construct
SEQUENCE: 41
gttctgaggt cattactgg                                                         19

SEQ ID NO: 42          moltype = DNA   length = 24
FEATURE                Location/Qualifiers
source                 1..24
                       mol_type = other DNA
                       organism = synthetic construct
SEQUENCE: 42
cccgccgctg cttttgcacg tgag                                                   24

SEQ ID NO: 43          moltype = DNA   length = 17
FEATURE                Location/Qualifiers
source                 1..17
                       mol_type = other DNA
                       organism = synthetic construct
SEQUENCE: 43
ctttatccag ccctcac                                                           17

SEQ ID NO: 44          moltype = DNA   length = 21
FEATURE                Location/Qualifiers
source                 1..21
                       mol_type = other DNA
                       organism = synthetic construct
SEQUENCE: 44
accctaactg acacacattc c                                                      21

SEQ ID NO: 45          moltype = DNA   length = 20
FEATURE                Location/Qualifiers
source                 1..20
                       mol_type = other DNA
                       organism = synthetic construct
SEQUENCE: 45
ccctcatagt tagcgtaacg                                                        20

SEQ ID NO: 46          moltype = DNA   length = 24
FEATURE                Location/Qualifiers
source                 1..24
                       mol_type = other DNA
                       organism = synthetic construct
SEQUENCE: 46
aatatacctc tatactttaa cgtc                                                   24

SEQ ID NO: 47          moltype = DNA   length = 20
FEATURE                Location/Qualifiers
source                 1..20
                       mol_type = other DNA
```

-continued

```
                                    organism = synthetic construct
SEQUENCE: 47
atgccatagc atttttatcc                                                   20

SEQ ID NO: 48        moltype = DNA   length = 18
FEATURE              Location/Qualifiers
source               1..18
                     mol_type = other DNA
                     organism = synthetic construct
SEQUENCE: 48
gatttaatct gtatcagg                                                     18

SEQ ID NO: 49        moltype = DNA   length = 18
FEATURE              Location/Qualifiers
source               1..18
                     mol_type = other DNA
                     organism = synthetic construct
SEQUENCE: 49
ccacacctcc ccctgaac                                                     18

SEQ ID NO: 50        moltype = DNA   length = 18
FEATURE              Location/Qualifiers
source               1..18
                     mol_type = other DNA
                     organism = synthetic construct
SEQUENCE: 50
cgcctggaga cgccatcc                                                     18

SEQ ID NO: 51        moltype = DNA   length = 19
FEATURE              Location/Qualifiers
source               1..19
                     mol_type = other DNA
                     organism = synthetic construct
SEQUENCE: 51
gatgttaacg ataccagcc                                                    19

SEQ ID NO: 52        moltype = DNA   length = 19
FEATURE              Location/Qualifiers
source               1..19
                     mol_type = other DNA
                     organism = synthetic construct
SEQUENCE: 52
gcgtgaatgt aagcgtgac                                                    19

SEQ ID NO: 53        moltype = DNA   length = 20
FEATURE              Location/Qualifiers
source               1..20
                     mol_type = other DNA
                     organism = synthetic construct
SEQUENCE: 53
ctagcaaaat aggctgtccc                                                   20

SEQ ID NO: 54        moltype = DNA   length = 20
FEATURE              Location/Qualifiers
source               1..20
                     mol_type = other DNA
                     organism = synthetic construct
SEQUENCE: 54
gacgatagtc atgccccgcg                                                   20

SEQ ID NO: 55        moltype = DNA   length = 23
FEATURE              Location/Qualifiers
source               1..23
                     mol_type = other DNA
                     organism = synthetic construct
SEQUENCE: 55
tgtatcttat ggtactgtaa ctg                                               23

SEQ ID NO: 56        moltype = DNA   length = 23
FEATURE              Location/Qualifiers
source               1..23
                     mol_type = other DNA
                     organism = synthetic construct
SEQUENCE: 56
ctttatgttt ttggcgtctt cca                                               23

SEQ ID NO: 57        moltype = DNA   length = 18
FEATURE              Location/Qualifiers
source               1..18
```

-continued

```
                          mol_type = other DNA
                          organism = synthetic construct
SEQUENCE: 57
gcgagagtag ggaactgc                                            18

SEQ ID NO: 58            moltype = DNA   length = 22
FEATURE                  Location/Qualifiers
source                   1..22
                          mol_type = other DNA
                          organism = synthetic construct
SEQUENCE: 58
aacatcagag attttgagac ac                                       22

SEQ ID NO: 59            moltype = DNA   length = 20
FEATURE                  Location/Qualifiers
source                   1..20
                          mol_type = other DNA
                          organism = synthetic construct
SEQUENCE: 59
cctctacaaa tgtggtatgg                                          20

SEQ ID NO: 60            moltype = DNA   length = 20
FEATURE                  Location/Qualifiers
source                   1..20
                          mol_type = other DNA
                          organism = synthetic construct
SEQUENCE: 60
gcccctaact ccgcccatcc                                          20

SEQ ID NO: 61            moltype = DNA   length = 19
FEATURE                  Location/Qualifiers
source                   1..19
                          mol_type = other DNA
                          organism = synthetic construct
SEQUENCE: 61
gggcaggaag agggcctat                                           19

SEQ ID NO: 62            moltype = DNA   length = 19
FEATURE                  Location/Qualifiers
source                   1..19
                          mol_type = other DNA
                          organism = synthetic construct
SEQUENCE: 62
tatggctagc atgactggt                                           19

SEQ ID NO: 63            moltype = DNA   length = 20
FEATURE                  Location/Qualifiers
source                   1..20
                          mol_type = other DNA
                          organism = synthetic construct
SEQUENCE: 63
gtggtttgtc caaactcatc                                          20

SEQ ID NO: 64            moltype = DNA   length = 21
FEATURE                  Location/Qualifiers
source                   1..21
                          mol_type = other DNA
                          organism = synthetic construct
SEQUENCE: 64
gagggcctat ttcccatgat t                                        21

SEQ ID NO: 65            moltype = DNA   length = 20
FEATURE                  Location/Qualifiers
source                   1..20
                          mol_type = other DNA
                          organism = synthetic construct
SEQUENCE: 65
taattagaat taatttgact                                          20

SEQ ID NO: 66            moltype = DNA   length = 33
FEATURE                  Location/Qualifiers
source                   1..33
                          mol_type = other DNA
                          organism = synthetic construct
SEQUENCE: 66
acactctttc cctacacgac gctcttccga tct                           33

SEQ ID NO: 67            moltype = DNA   length = 34
FEATURE                  Location/Qualifiers
```

-continued

```
source                  1..34
                        mol_type = other DNA
                        organism = synthetic construct
SEQUENCE: 67
gtgactggag ttcagacgtg tgctcttccg atct                                  34

SEQ ID NO: 68           moltype = DNA   length = 33
FEATURE                 Location/Qualifiers
source                  1..33
                        mol_type = other DNA
                        organism = synthetic construct
SEQUENCE: 68
tcgtcggcag cgtcagatgt gtataagaga cag                                   33

SEQ ID NO: 69           moltype = DNA   length = 34
FEATURE                 Location/Qualifiers
source                  1..34
                        mol_type = other DNA
                        organism = synthetic construct
SEQUENCE: 69
gtctcgtggg ctcggagatg tgtataagag acag                                  34

SEQ ID NO: 70           moltype = DNA   length = 36
FEATURE                 Location/Qualifiers
source                  1..36
                        mol_type = other DNA
                        organism = synthetic construct
SEQUENCE: 70
cgtgctggat tggctcacca gacaccttcc gaccat                                36

SEQ ID NO: 71           moltype = DNA   length = 35
FEATURE                 Location/Qualifiers
source                  1..35
                        mol_type = other DNA
                        organism = synthetic construct
SEQUENCE: 71
agttgacaag cggtagcctg cacaccttcc gacat                                 35

SEQ ID NO: 72           moltype = DNA   length = 30
FEATURE                 Location/Qualifiers
source                  1..30
                        mol_type = other DNA
                        organism = synthetic construct
SEQUENCE: 72
ccatctcatc cctgcgtgtc tccgactcag                                       30

SEQ ID NO: 73           moltype = DNA   length = 23
FEATURE                 Location/Qualifiers
source                  1..23
                        mol_type = other DNA
                        organism = synthetic construct
SEQUENCE: 73
cctctctatg ggcagtcggt gat                                              23

SEQ ID NO: 74           moltype = DNA   length = 38
FEATURE                 Location/Qualifiers
source                  1..38
                        mol_type = other DNA
                        organism = synthetic construct
SEQUENCE: 74
tttttttttt aatgtacttc gttcagttac gtattgct                              38

SEQ ID NO: 75           moltype = DNA   length = 22
FEATURE                 Location/Qualifiers
source                  1..22
                        mol_type = other DNA
                        organism = synthetic construct
SEQUENCE: 75
gcaatacgta actgaacgaa gt                                                22

SEQ ID NO: 76           moltype = DNA   length = 45
FEATURE                 Location/Qualifiers
source                  1..45
                        mol_type = other DNA
                        organism = synthetic construct
SEQUENCE: 76
atctctctct tttcctcctc ctccgttgtt gttgttgaga gagat                      45

SEQ ID NO: 77           moltype = DNA   length = 69
```

```
FEATURE              Location/Qualifiers
source               1..69
                     mol_type = other DNA
                     organism = synthetic construct
SEQUENCE: 77
ctctcgtcgc gttctgagac taccgtgaaa cgcgtatcgc gcgcaaatag ctcaattggt   60
cgtagcaag                                                           69

SEQ ID NO: 78        moltype = DNA   length = 70
FEATURE              Location/Qualifiers
source               1..70
                     mol_type = other DNA
                     organism = synthetic construct
SEQUENCE: 78
ctctcgtgat tatgataaac taccgtgaaa cgcgtatcgc gcgcataata gctcaattgg   60
tcgtagcaag                                                          70

SEQ ID NO: 79        moltype = DNA   length = 70
FEATURE              Location/Qualifiers
source               1..70
                     mol_type = other DNA
                     organism = synthetic construct
SEQUENCE: 79
ctctcgtctg ggttaattac taccgtgaaa cgcgtatcgc gcgcataata gctcaattgg   60
tcgtagcaag                                                          70

SEQ ID NO: 80        moltype = DNA   length = 70
FEATURE              Location/Qualifiers
source               1..70
                     mol_type = other DNA
                     organism = synthetic construct
SEQUENCE: 80
ctctcgtaat tatatttaac taccgtgaaa cgcgtatcgc gcgcataata gctcaattgg   60
tcgtagcaag                                                          70

SEQ ID NO: 81        moltype = DNA   length = 69
FEATURE              Location/Qualifiers
source               1..69
                     mol_type = other DNA
                     organism = synthetic construct
SEQUENCE: 81
ctctcgtaac tttttcgact accgtgaaac gcgtatcgcg cgcataatag ctcaattggt   60
cgtagcaag                                                           69

SEQ ID NO: 82        moltype = DNA   length = 70
FEATURE              Location/Qualifiers
source               1..70
                     mol_type = other DNA
                     organism = synthetic construct
SEQUENCE: 82
ctctcgtcac tgtttttaac taccgtgaaa cgcgtatcgc gcgcataata gctcaattgg   60
tcgtagcaag                                                          70

SEQ ID NO: 83        moltype = DNA   length = 70
FEATURE              Location/Qualifiers
source               1..70
                     mol_type = other DNA
                     organism = synthetic construct
SEQUENCE: 83
ctctcgtagt tatgatatac taccgtgaaa cgcgtatcgc gcgcataata gctcaattgg   60
tcgtagcaag                                                          70

SEQ ID NO: 84        moltype = DNA   length = 70
FEATURE              Location/Qualifiers
source               1..70
                     mol_type = other DNA
                     organism = synthetic construct
SEQUENCE: 84
ctctcgtcgg ggttaattac taccgtgaaa cgcgtatcgc gcgcataata gctcaattgg   60
tcgtagcaag                                                          70

SEQ ID NO: 85        moltype = DNA   length = 69
FEATURE              Location/Qualifiers
source               1..69
                     mol_type = other DNA
                     organism = synthetic construct
SEQUENCE: 85
ctctcgtgtt tataggggac taccggtgaa acgcgtatcg cgcgaataat agctcaattg   60
gtcgtagca                                                           69
```

-continued

```
SEQ ID NO: 86          moltype = DNA  length = 69
FEATURE                Location/Qualifiers
source                 1..69
                       mol_type = other DNA
                       organism = synthetic construct
SEQUENCE: 86
ctctcgtact tatgagtata ctaccgtgaa acgcgtatcg cgcgcataat agctcaattg  60
gtcgtagca                                                          69

SEQ ID NO: 87          moltype = DNA  length = 70
FEATURE                Location/Qualifiers
source                 1..70
                       mol_type = other DNA
                       organism = synthetic construct
SEQUENCE: 87
ctctcgtcac tgtttttaac taccgtgaaa cgcgtatcgc gcgcataata gctcaattgg  60
tcgtagcaag                                                         70

SEQ ID NO: 88          moltype = DNA  length = 70
FEATURE                Location/Qualifiers
source                 1..70
                       mol_type = other DNA
                       organism = synthetic construct
SEQUENCE: 88
ctctcgtctt ggttaattac taccgtgaaa cgcgtatcgc gcgcataata gctcaattgg  60
tcgtagcaag                                                         70

SEQ ID NO: 89          moltype = DNA  length = 69
FEATURE                Location/Qualifiers
source                 1..69
                       mol_type = other DNA
                       organism = synthetic construct
SEQUENCE: 89
ctctcgtaac tatttcgact accgtgaaac gcgtatcgcg cgcataatag ctcaattggt  60
cgtagcaag                                                          69
```

CHROMATIN PROFILING COMPOSITIONS AND METHODS

CROSS-REFERENCE TO RELATED APPLICATION

This application is a continuation of International Application PCT/US2023/081014, filed Nov. 22, 2023, which claims the priority benefit of U.S. provisional application No. 63/427,749 filed Nov. 23, 2022, the contents of which are incorporated herein in their entireties by reference thereto.

INCORPORATION OF SEQUENCE LISTING

The instant application contains a Sequence Listing which has been submitted electronically in XML format and is hereby incorporated by reference in its entirety. Said XML copy, created on Nov. 22, 2023 is named 5371105pct and is 86,016 bytes in size.

FIELD

The instant disclosure relates generally to the identification and analysis of epigenetic and other modifications to the structures or features of chromatin, nucleosomes, and related nucleic acids.

BACKGROUND

Chromatin is the complex of DNA and proteins that organizes the genetic code within the nuclei of eukaryotic cells. The nucleosome is the fundamental subunit of chromatin. A nucleosome consists of an octamer of proteins around which approximately two turns of DNA is wrapped plus a linker of DNA that is approximately 80 bp long. The two turns of DNA wrapping the proteins consist of approximately 146 base pairs. The octamer of proteins includes two copies of each of the histone proteins H2A, H2B, H3, and H4. The 80 bp linker connects the nucleosome to another nucleosome in a repeating pattern that together makes up a chromosome.

The structural features of chromatin, which regulate gene expression, are determined by how the nucleosomes and other proteins are packed together in the nucleus. Loosely packed chromatin is called euchromatin and is transcriptionally active; the genes encoded by these regions are being expressed. Densely packed chromatin is called heterochromatin and is inactive in gene expression. Histone tail modifications are one of the most important features that determine how chromatin is packed. These modifications can be added or removed by cells to regulate packing and, accordingly, gene expression.

A histone tail is the disordered extension of the N-terminal domain of each histone protein beyond the nucleosome core structure. They range in length from approximately 25 to 60 amino acids and are typically rich in basic amino acids residues, especially lysine and arginine. Most histone tail modifications are methylation and acetylation of specific lysine and arginine residues, but other modifications including phosphorylation and ubiquitination also occur naturally. These modifications are known to be intimately connected with cell development, tissue differentiation, aging, and disease progression, such as cancer. Enzymes involved in histone modification are clinically proven drug targets. For example, there are currently four FDA-approved cancer chemotherapeutic drugs on the market that inhibit histone deacetylation, an enzyme involved in removing the acetyl mark from histone tails.

Another important class of gene expression regulators that are associated with chromatin are transcription factors. There are 1500-1600 transcription factors in the human genome. Transcription factors are DNA binding proteins that can promote or inhibit gene expression by coordinating access of RNA polymerase II to the promotor region of a gene. RNA polymerase II is another DNA binding protein that transcribes DNA into different RNA species.

Motivated by histone modifications' key roles as regulators of chromatin packing, gene expression and human health, a number of methods have been developed for determining which histone modifications are associated with the specific sequence of DNA of each nucleosome. The most prevalent of these analysis methods is ChIP sequencing, which combines chromatin immunoprecipitation with DNA sequencing. In ChIP-seq, an antibody specific to a histone modification is coupled to a bead. A sample of chromatin is sheared mechanically or treated enzymatically to break it into separate nucleosomes. A solution containing these nucleosomes is then combined with the beads under conditions suitable for the antibody to bind to its cognate histone modification. Nucleosomes bearing this modification are thus bound to the beads and can be separated by isolating the beads from the solution. Following isolation, the beads are washed to remove the modified histones, library preparation for DNA sequencing is performed, and next-generation DNA sequencing is then used to identify the specific DNA sequences corresponding to the modified nucleosomes. Antibody-guided chromatin tagmentation (ACT-seq) is an alternative to this method that also uses modification-specific antibodies to recognize histone tail modifications, but uses barcode-loaded transposomes to barcode the DNA of a nucleosome if the antibody-specific histone tail modification is present.

Upon cell death, the genome degrades, and chromatin, mostly in the form of nucleosomes, is released into the blood as cell-free circulating nucleosomes that retain their histone modifications.

There are over 60 distinct sites at which the histones of one nucleosome can be modified, and each site can be modified in more than one way, leading to a large number of possible modifications. Some of these modifications are more prevalent than others and are associated with well-established functional significance. The most commonly analyzed histone modifications are acetylation, methylation, phosphorylation, ubiquitination, and sumoylation. Modifications can either promote or repress gene expression, depending on the nature and site of the modification. It is known that modifications can operate cooperatively to influence gene expression.

Traditional histone modification profiling methods provide information on the types and levels of histone modifications present in a sample, but they do not reveal the spatial distribution of these molecules within a tissue.

Despite the significance of these modifications and their complexity, the existing methods for histone modification analysis are limited in their capacity to analyze multiple modifications concurrently without splitting the sample and performing the analysis of each modification in a separate assay. Another unmet need is the ability to obtain information about the spatial organization of chromatin and its underlying histone modifications in the context of a tissue. Accordingly, there is a need in the art for improved compositions and methods for identifying, analyzing, quantifying, and locating chromatin and nucleosome modifications in relation to genome coordinate and in relation to the broader context of a tissue. Such advancements would pave the way for discovery of key regulatory mechanisms of biology in health and disease, and the development of new treatment paradigms in medicine.

SUMMARY OF THE INVENTION

Provided herein are compositions and methods for the identification and analysis of epigenetic and other chemical modifications to the nucleosomes including nucleic acids and histone proteins, or DNA binding proteins. The instant disclosure provides highly parallelized, sensitive, accurate, and high-throughput methods for profiling a potentially unlimited number of nucleosome modifications and DNA binding proteins simultaneously.

In some embodiments, the disclosure provides a target-binding conjugate comprising a binding domain and an adapter, wherein the binding domain binds specifically to a histone modification or to a DNA binding protein, and wherein the adapter comprises a nucleic acid barcode sequence unique to the target bound specifically by the binding domain. In some aspects, the present disclosure includes a composition comprising the nucleosome-binding conjugate and a buffer, e.g., a ligation buffer. In some aspects, the DNA binding protein may be bound to a DNA region that connects two nucleosomes.

In some embodiments, the disclosure provides a composition comprising (i) a substrate, (ii) a binding domain coupled to the substrate, and (iii) an adapter, wherein the binding domain binds specifically to a histone modification or DNA binding protein, wherein the adapter comprises a nucleic acid barcode sequence unique to the histone modification or DNA binding protein.

In some embodiments, the disclosure provides a method for analyzing a plurality of nucleosomes and protein-DNA complexes, the method comprising: (i) contacting a plurality of substrates comprising at least one composition of any one or combination of numbered aspects disclosed herein with a solution comprising the plurality of nucleosomes and protein-DNA complexes, wherein the binding domain binds to a DNA binding protein or a nucleosome comprising a histone modification; (ii) ligating an adapter with the nucleic acid barcode to the target DNA of the nucleosome comprising the histone modification or DNA binding protein; (iii) introducing, e.g., ligating universal sequences for amplifying the target DNA; (iv) amplifying the barcoded target DNA; and (v) analyzing the amplified barcoded target DNA by sequencing.

In some embodiments, the disclosure provides a method for analyzing a plurality of nucleosomes and protein-DNA complexes, the method comprising: (i) contacting a plurality of substrates comprising at least one of any one or combination of numbered aspects disclosed herein with a solution comprising the plurality of nucleosomes and protein-DNA complexes, wherein the binding domain binds to a DNA binding protein or a nucleosome comprising a histone modification; (ii) ligating an adapter with the nucleic acid barcode to the target DNA of the nucleosome comprising the histone modification or DNA binding protein; (iii) releasing the nucleosome or DNA binding protein from the substrate by cleaving the ligated adapter; (iv) repeating steps (i) through (iii) at least once; (v) introducing, e.g., ligating universal nucleic acid sequences for amplifying the target DNA; (vi) amplifying the barcoded target DNA; and (vii) analyzing the amplified barcoded target DNA by sequencing.

In some embodiments, the disclosure provides a method for analyzing a plurality of nucleosomes and protein-DNA complexes, the method comprising: (i) contacting one or a plurality of substrates comprising one composition of any one or combination of numbered aspects disclosed herein with a solution comprising the plurality of nucleosomes and protein-DNA complexes, wherein the binding domain binds to a DNA binding protein or a nucleosome comprising a histone modification; (ii) adding an adapter to the plurality of nucleosomes bound to the binding domain; (iii) ligating the adapter with the nucleic acid barcode to the target DNA of the nucleosome comprising the histone modification or DNA binding protein; (iv) releasing the nucleosome from the binding domain by adding a buffer that disrupts the interaction between binding domain and nucleosome; (v) repeating steps (i) to (iv) at least once; (vi) introducing, e.g., ligating universal sequences for amplifying the target DNA; (vii) amplifying the barcoded target DNA; and (viii) analyzing the amplified barcoded target DNA by sequencing.

In some embodiments, the disclosure provides a nucleosome-binding conjugate comprising: i) a binding domain, and ii) an adapter conjugated to the binding domain, wherein the binding domain binds to a DNA binding protein or a nucleosome comprising a histone modification, wherein the adapter comprises a nucleic acid barcode sequence unique to the histone modification or the DNA binding protein.

In some embodiments, the disclosure provides a method for analyzing a plurality of nucleosomes and protein-DNA complexes, the method comprising: (i) contacting a solution comprising the plurality of nucleosomes and protein-DNA complexes with a solution comprising at least one nucleosome-binding conjugate of any one or combination of numbered aspects disclosed herein, wherein the binding domain binds to a DNA binding protein or a nucleosome comprising a histone modification; (ii) ligating an adapter with the nucleic acid barcode of the binding conjugate to the target DNA of the nucleosome comprising the histone modification or DNA binding protein to produce barcoded target DNA in an environment wherein generation of off-target barcoded DNA is less than 20% of the barcoded target DNA; (iii) ligating universal sequences for amplifying the target DNA; (iv) amplifying the barcoded target DNA; and (v) analyzing the amplified barcoded target DNA by sequencing.

In some embodiments, the disclosure provides a method for analyzing a plurality of nucleosomes and protein-DNA complexes, the method comprising: (i) immobilizing a plurality of nucleosomes and protein-DNA complexes on a substrate at a spacing wherein off-target barcoding is less than 20%; (ii) contacting the immobilized nucleosomes and protein-DNA complexes with a solution comprising at least one composition of any one or combination of numbered aspects disclosed herein, wherein the binding domain binds to a DNA binding protein or a nucleosome comprising a histone modification; (iii) ligating an adapter with the nucleic acid barcode of the nucleosome-binding conjugate to the target DNA of the nucleosome comprising the histone modification or DNA binding protein; (iv) cleaving the adapter such that a nucleic acid end is generated with the structure suitable for ligation to other adapters; (v) repeating steps (ii) through (iv) at least once; (vi) introducing, e.g., ligating universal nucleic acid sequences for amplifying the target DNA; (vii) amplifying the barcoded target DNA; and (viii) analyzing the amplified barcoded target DNA by sequencing.

In some embodiments, the disclosure provides a method for analyzing a plurality of nucleosomes in the context of a tissue, the method comprising: (i) immobilizing a plurality of nucleosome-binding conjugates on a planar microarray substrate at a spacing wherein off-target barcoding is less than 20%; (ii) layering a tissue section on top of the planar microarray substrate comprising the plurality of nucleosome-binding conjugates; (iii) permeabilizing the tissue cells; (iv) digesting the chromatin with endonuclease and capturing the nucleosomes by the immobilized nucleosome-binding conjugates; (v) ligating an adapter with the nucleic acid barcode and a spatial identifier sequence of the nucleosome-binding conjugate to the target DNA of the nucleosome comprising the histone modification or DNA binding protein to produce barcoded target DNA in an environment wherein generation of off-target barcoded DNA is less than 20% of the barcoded target DNA; (vi) introducing universal sequences for amplifying the target DNA; (vii) amplifying the barcoded target DNA; (vii) analyzing the amplified barcoded target DNA by sequencing; and (viii) determining the identity of the histone modification or DNA binding protein and their spatial location on the planar microarray substrate based on the barcode and the spatial identifier sequence.

In some embodiments, the disclosure provides a method for analyzing a plurality of nucleosomes and protein-DNA complexes, the method comprising: (i) introducing a universal connector to the target DNA of the nucleosome or protein-DNA complex; (ii) contacting a solution comprising the plurality of nucleosomes and protein-DNA complexes with a solution comprising at least one binding conjugate of any one or combination of numbered aspects disclosed herein, wherein the binding domain binds to a DNA binding protein or a nucleosome comprising a histone modification; (iii) connecting the adapters of the bound plurality of binding conjugates by ligation; (iv) hybridizing the universal connector of the target DNA to the 5'end of the ligated adapters; (v) copying the sequence of the ligated adapters to produce a copy of barcoded target DNA; (vi) introducing, e.g., ligating universal nucleic acid sequences for amplifying the target DNA; (vii) amplifying the barcoded nucleosome DNA, and (viii) analyzing the barcoded target DNA by sequencing.

In some embodiments, the disclosure provides a method for diagnosing a cancer or cancer sub-type associated with one or more types of histone modifications, comprising analyzing a plurality of nucleosomes and protein-DNA complexes according to any one or combination of numbered aspects disclosed herein.

In some embodiments, the disclosure provides a method of detecting the presence of a cancer, or monitoring the progression or treatment response of a cancer, comprising analyzing a plurality of nucleosomes and protein-DNA complexes according to any one or combination of numbered aspects disclosed herein.

In some embodiments, the disclosure provides a method of detecting histone modifications of cell-free nucleosomes as biomarkers in liquid biopsy of blood plasma. Histone modifications of cell-free nucleosomes inform on DNA-related activities within the cells of origin. In some embodiments, the disclosure provides multiplexed detection of histone modifications in low sample input scenarios, such as the analysis of cell-free nucleosomes in blood plasma, which contains only 20 to 60 ng of nucleosomes per mL.

In some embodiments, the disclosure provides a method of any one or combination of numbered aspects disclosed herein, comprising obtaining the plurality of nucleosomes and protein-DNA complexes from a blood sample.

In some embodiments, the disclosure provides a method of any one or combination of numbered aspects disclosed herein, comprising obtaining the plurality of nucleosomes and protein-DNA complexes from a tissue biopsy sample.

In some embodiments, the disclosure provides a kit for monitoring epigenetic changes over time in a subject undergoing treatment for cancer, comprising the composition of any one or combination of numbered aspects disclosed herein.

In some embodiments, the disclosure provides any of the molecules, complexes, work flows, or methods depicted in the figures or described in the following disclosures and examples.

These and other aspects of the invention will be apparent upon reference to the following detailed description, claims, embodiments, procedures, compounds, and/or compositions and associated background information and references, which are hereby incorporated in their entirety.

BRIEF DESCRIPTION OF THE DRAWINGS

FIGS. 1A-1B are schematics showing sample preparation for histone profiling, including, depending on the downstream assay chemistry, end-repair or A-tailing and/or ligation of the ends of the DNA that is wrapped around the histone to a universal capture sequence. As a non-limiting example, FIG. 1A shows that blood contains circulating nucleosomes that can be directly used in the barcoding assay. As a non-limiting example, FIG. 1B shows that tissue or cell culture samples comprise nucleosomes that can be isolated by digesting the chromatin with a DNA nuclease and used in the assay.

In FIG. 2A, "MBC1", "MBC2" and "MBC3" are ligated to the same target nucleic acid to indicate the presence of three different histone modifications ("Mods").

FIG. 2B depicts a scenario where a plurality of nucleosomes is present, each with a single modification.

FIG. 3A shows a schematic of a substrate-based barcoding assay where the adapters are tethered to a bead surface. A bead pool is assembled from different bead types, where each bead type displays one type of binding domain and barcoded adapter. Because each bead type exhibits one type of binding domain and one type of barcoded adapter, the surface density of the molecules does not affect barcoding specificity. FIG. 3B shows barcoding by nucleosome-binding conjugates that are spaced out on a surface to significantly reduce off-target barcoding.

FIG. 11A shows the number of sequencing reads for each MBC associated with each synthetic nucleosome. KmetStat H3K4me3 control nucleosomes were enriched in MBC101 indicating correct identification of H3K4me3. KmetStat_H3K4me2 control nucleosomes were enriched in MBC103 indicating correct identification of H3K4me2. The KmetStat_WT nucleosomes were unmodified and received very few MBCs. FIG. 11B shows the number of control nucleosome sequences that were identified for each MBC. For MBC101, KmetStat_H3K4me3 nucleosomes are the most represented reads. For MBC103, KmetStat_H3K4me2 nucleosomes are the most represented reads consistent with correct barcoding. FIG. 11C and FIG. 11D show the enrichment factors calculated from the raw sequencing reads. The enrichment factor is defined as the reads per million for the IP reaction (beads with binding domains directed against H3K4me3 and H3K4me2) divided by the reads per million of the INPUT reaction (beads directed against histone 3 (H3)). FIG. 11E and FIG. 11F show two example genes and the read pile ups indicating genomic regions with modifications in HeLa cells.

FIG. 13A shows the sequencing reads that associated the synthetic nucleosomes with MBC107 and MBC109. FIG. 13B shows the associated enrichment factors. FIG. 13C shows example sequencing reads providing evidence for the presence of two barcodes (SEQ ID NOs: 77-89 are listed in FIG. 13C).

FIG. 14 shows an agrose gel and library yields obtained in an experiment that optimized the conditions for eluting the synthetic nucleosome after the first barcoding cycle without causing any damage that would prevent a second barcoding cycle.

FIGURE REFERENCE KEY

Figure 2A:
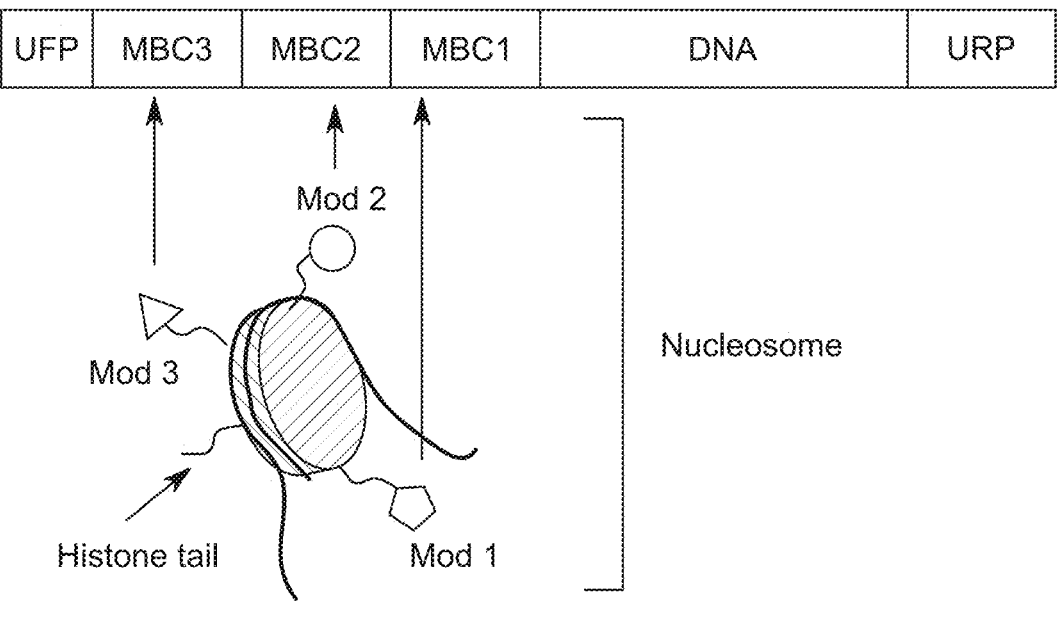
FIGS. 2A-2B show co-localizing histone modifications of the same nucleosome by DNA barcoding (FIG. 2A) and multiplexed detection of histone modifications of different nucleosomes (FIG. 2B).

IP: immunoprecipitation
MBC: Modification barcode
MOD: Modification
Read 1: Read 1 primer site
Read 2: Read 2 primer site
5'-P: 5'-phosphate
U: Uracil
UL: Universal ligation site
UFP: Universal forward primer site
URP: Universal reverse primer site
FSA: Forward sequencing adapter
RSA: Reverse sequencing adapter
UMI: Unique Molecular Identifier
RE: Restriction site
"MBC" means modification barcode.
"SP" means spatial identifier.

DETAILED DESCRIPTION

Provided herein are compositions and methods for the profiling of histone modifications and DNA binding proteins. The methods combine molecular recognition of histone modifications and DNA binding proteins with a step of writing the information from this recognition event into the neighboring genetic sequence of the target nucleic acid the histone or DNA binding protein is attached to using a barcode. The resultant barcoded nucleic acids are then converted into sequencing libraries and read by, for example, nucleic acid sequencing methods or other methods. This step reveals the sequence of the barcode, which is correlated with the target DNA. Sequencing may also allow for localization of the histone modification and DNA binding proteins, such as transcription factors. The high through-put profiling methods described herein allow for identification of the nature and location of several or all histone modifications in parallel. These methods also allow for determination of abundance and stoichiometry of the histone modifications.

The disclosures of WO2022/115608 are incorporated herein by reference in their entirety for all purposes.

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope described herein to those skilled in the art.

Method steps recited herein may be performed concurrently or sequentially unless stated otherwise or unless it is apparent from the described methods that a step must first be performed before its product is used in a subsequent step.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

All publications, patent applications, patents, GenBank/Uniprot or other accession numbers and other references mentioned herein are incorporated by reference in their entirety for all purposes.

Definitions

The following terms are used in the description herein and the appended claims.

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, can be used to describe reasonably understood variations, for example ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features described herein can be used in any combination. Moreover, in some embodiments, any feature or combination of features set forth herein can be excluded or omitted. To illustrate further, if, for example, the specification indicates that a particular DNA base can be selected from A, T, G and/or C, this language also indicates that the base can be selected from any subset of these base(s) for example A, T, G, or C; A, T, or C; T or G; only C; etc., as if each such subcombination is expressly set forth herein. Moreover, such language also indicates that one or more of the specified bases can be disclaimed. For example, in some embodiments the nucleic acid is not A, T or G; is not A; is not G or C; etc., as if each such possible disclaimer is expressly set forth herein.

As used herein, the terms "reduce," "reduces," "reduction" and similar terms can be used to disclose a decrease of at least about 10%, about 15%, about 20%, about 25%, about 35%, about 50%, about 75%, about 80%, about 85%, about 90%, about 95%, about 97% or more.

As used herein, the terms "increase," "improve," "enhance," "enhances," "enhancement" and similar terms can be used to disclose an increase of at least about 10%, about 15%, about 20%, about 25%, about 50%, about 75%, about 100%, about 150%, about 200%, about 300%, about 400%, about 500%, or more.

As used herein the term "histone modification" refers to modifications to chromatin associated protein. In some embodiments, a nucleosome comprises the histone modification. In some embodiments, the histone modification is one or more of acetylation, methylation, citrullination, phosphorylation, ubiquitylation (also referred to as ubiquitination), sumoylation, ADP ribosylation, deamination, proline isomerization, and other histone modifications known to persons skilled in the art. In some embodiments, the histone modification is sumoylation of lysine or arginine. In some embodiments, the histone modification is phosphorylation of tyrosine, serine, and threonine. In some embodiments, the histone modification is any single modification or any combination of modifications listed in Table 3.

The term "epigenetic change" is used herein to refer to a phenotypic change in a living cell, organism, etc., that is not encoded in the primary sequence (i.e., A, T, C, and G) of that cell's or organism's DNA. Epigenetic changes may include, for example, chemical alterations of nucleotides and/or histones (i.e., the proteins involved in coiling and packaging DNA in the nucleus). Epigenetic changes may include the histone modifications discussed herein and other histone modifications known to persons skilled in the art. Common histone modifications include H3K4me1, H3K4me3, H3K36me3, H3K79me2, H3K9Ac, H3K27Ac, H4K16Ac, H3K27me3, H3K9me3. Illustrative DNA nucleotide modifications include the common epigenetic marker 5-methylcytidine (5mC) and its oxidation products 5-hydroxymethylcytidine (5hmC), 5-formylcytidine (5fC), 5-carboxymethylcytidine (5caC). 5mC is well known for its role in gene silencing, and a growing body of evidence suggests metabolic function for the oxidized intermediates 5hmC, 5fC, and 5caC on the pathway for demethylation of 5mC.

The term "genome" refers to all the DNA in a cell or population of cells, or a selection of specific types of DNA molecules (e.g., coding DNA, noncoding DNA, mitochondrial DNA, or chloroplast DNA.) The term "transcriptome" refers to all RNA molecules produced in one or a population of cells, or a selection of specific types of RNA molecules (e.g., mRNA vs. ncRNA, or specific mRNAs within an mRNA transcriptome) contained in a complete transcriptome. In some embodiments, a transcriptome comprises multiple different types of RNA, such as coding RNA (i.e., RNA that is translated into a protein, e.g., mRNA) and non-coding RNA. A non-limiting list of various types of RNA molecules found in a transcriptome, all of which may contain modified nucleosides, includes: 7SK RNA, signal recognition particle RNA, antisense RNA, CRISPR RNA, Guide RNA, long non-coding RNA, microRNA, messenger RNA, piwi-interacting RNA, repeat-associated siRNA, retrotransposon, ribonuclease MRP, ribonuclease P, ribosomal RNA, small Cajal body-specific RNA, small interfering RNA, smY RNA, small nucleolar RNA, small nuclear RNA, and trans-acting siRNA. The term "chromatin," as used herein, refers to a complex of molecules including proteins and polynucleotides (e.g. DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA. The function of chromatin is to efficiently package DNA into a small volume to fit into the nucleus of a cell and protect the DNA structure and sequence. Packaging DNA into chromatin allows for mitosis and meiosis, prevents chromosome breakage, and regulates DNA replication and accessibility of genes for expression.

The term "isolated chromatin," as used herein, refers to a source of chromatin that is caused to be made available. Isolated nuclei (which can be lysed to produce chromatin) as well as isolated chromatin (i.e., the product of lysed nuclei) are both considered types of chromatin isolated from a population of cells. The term "nucleosome" means a complex of at least a core of eukaryotic (e.g., mammalian, yeast, insect, or plant) mammalian histone proteins (e.g., two H2A proteins, two H2B proteins, two H3 proteins, and two H4 proteins) with about 147 base pairs of a dsDNA molecule wrapped around the core of mammalian histone proteins. Structural features of nucleosomes are well known in the art.

As used herein, the term "target nucleic acid" refers to a nucleic acid that is wrapped around the histones forming the nucleosome. In some aspects, the target nucleic acid is a target DNA. The target DNA may be part of a nucleosome. The binding domain described herein may recognize a histone modification or a DNA binding protein of a nucleosome and bind thereto. In some aspects, the DNA binding protein may be bound to a DNA region that connects two nucleosomes.

As used herein, the term "surface" or "substrate" will be used to refer to any solid support. For example, a substrate may be a bead, microarray, chip, flowcell, fluidics device, plate, slide, dish, membrane, frits, or 3-dimensional matrix. Microarrays are slides spotted with biomolecules, for example adapters or nucleosome-binding conjugates, where each spot comprises a distinct composition. Flowcells are sample cells designed so that liquid samples can be continuously flowed through. As described herein, the binding domains described herein may be coupled to one or more substrates, and a substrate may be coupled to one or more binding domains. Substrates may be formed from a variety of materials. In some embodiments, the substrate is a resin, a membrane, a fiber, or a polymer. In some embodiments, the substrate comprises sepharose, agarose, cellulose, polystyrene, polymethacrylate, and/or polyacrylamide. In some embodiments, the substrate comprises a polymer, such as a synthetic polymer. A non-limiting list of synthetic polymers includes: poly(ethylene)glycol, polyisocyanopeptide polymers, polylactic-co-glycolic acid, poly($\epsilon$-caprolactone) (PCL), polylactic acid, poly(3-hydroxybutyrate-co-3-hydroxyvalerate) (PHBV), chitosan and cellulose.

Figures 3A, 3B:
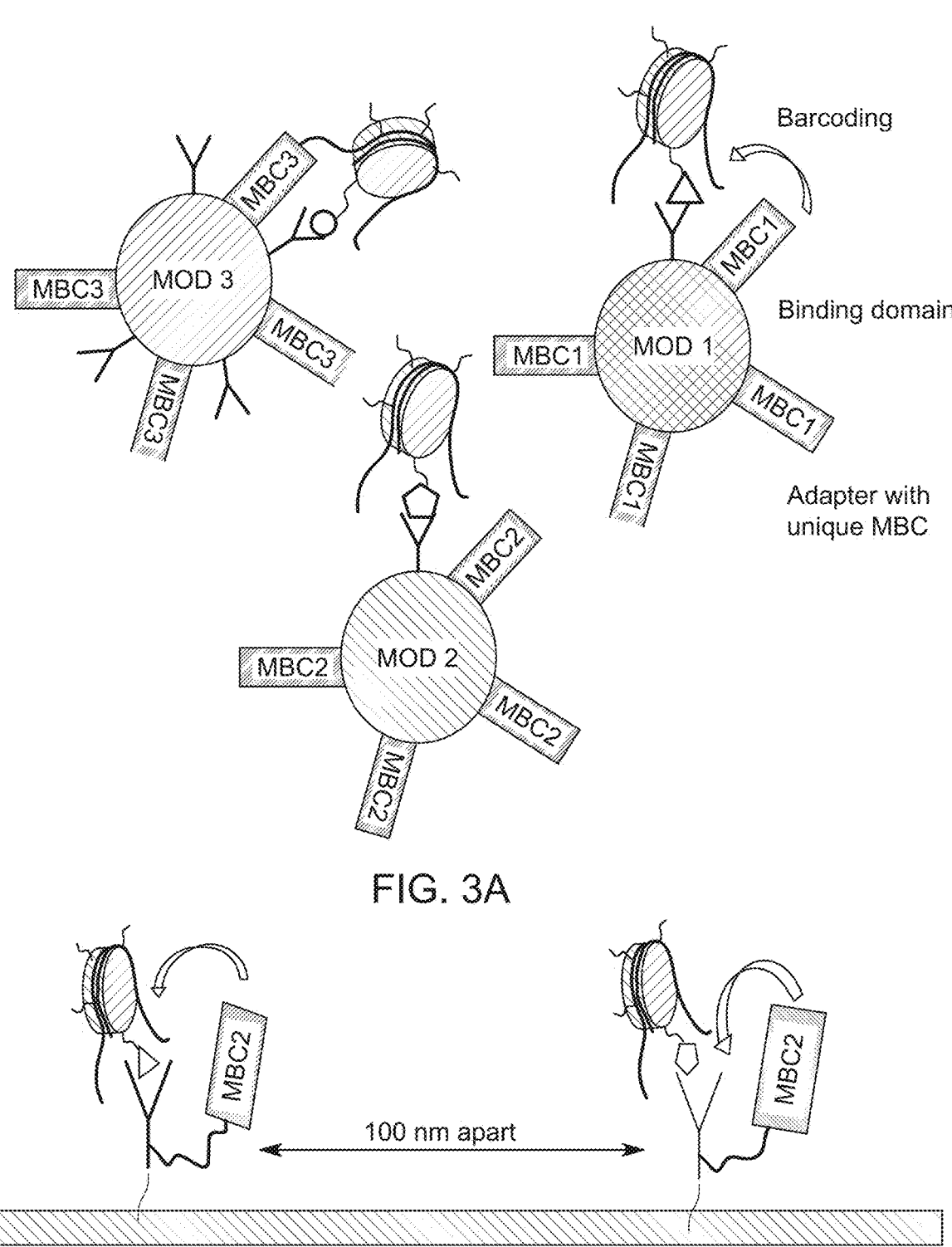
FIGS. 3A and 3B show that multiplexed detection of histone modifications may be performed in two configurations: adapters may be tethered to a surface proximal to the binding domains (FIG. 3A) or the adapters are tethered directly to the binding domain (FIG. 3B).

As shown in FIG. 3A, "monoclonal substrates" may comprise binding domains and barcoded DNA adapters. The substrate can be a bead, a section of a microarray, a lane of a microfluidics device, or a well in a microtiter plate. Each monoclonal substrate comprises one type of binding domain specific to a histone modification, for example an antibody, and many copies of a DNA adapter exhibiting a modification barcode (MBC). After or while immunoprecipitating the nucleosomes and the DNA binding proteins, the adapter is transferred to the DNA to indicate the modification.

As used herein, the term "barcode" refers to a synthetically produced nucleic acid. Unique barcodes may be assigned to specific nucleosome modifications or DNA binding proteins, to allow for specific identification of those targets in the methods described herein. Accordingly, a barcode is "unique" to a histone modification or a DNA binding protein if it is used specifically to identify that modification or protein in one or more of the methods described herein. In other instances, a barcode is "unique" to the location of nucleosome-binding conjugate that is tethered to the surface of a microarray. Barcodes may be produced using methods known in the art, such as solid phase oligonucleotide synthesis. In some embodiments, a barcode may be a DNA barcode (i.e., it may comprise a DNA sequence). In some embodiments, a barcode may comprise a synthetic DNA structure, such as a peptide nucleic acid (PNA) or a locked nucleic acid (LNA). In some embodiments, the synthetic DNA structure may comprise one or more modified bases. In some embodiments, a barcode may be an RNA barcode (i.e., it may comprise an RNA sequence). Barcodes may be any length, such as a length in the range of about 4 to about 150 nucleotides. In some embodiments, a barcode is about 4 to about 20 nucleotides in length, such as about 4, about 5, about 6, about 7, about 8, about 9, about 10, about 11, about 12, about 13, about 14, about 15, about 16, about 17, about 18, about 19, or about 20 nucleotides in length. Typically, a barcode will comprise a rationally designed sequence that is not found in the genome of any known organism. However, in some embodiments, a barcode may comprise a known sequence. For example, the sequence of the barcode may comprise a signature associated with a pathogen or other biological material. In some embodiments, a barcode may comprise a sequence configured to facilitate a sequencing reaction. The terms "barcode" and "adapter" may sometimes be used interchangeably herein. As will be understood in the art, an adapter may, in some embodiments, consist of a barcode. In some embodiments, an adapter may comprise a barcode and one or more additional elements as described below and as shown in FIGS. 2A-2B, FIG. 4, FIGS. 7A-7B, FIG. 8, FIG. 9 and FIGS. 15A-15B. In some embodiments, an "adapter" may comprise a spatial identifier (SP) sequence. As used herein a "spatial identifier sequence" or "spatial identifier" defines the location of a nucleosome-binding conjugate or an adapter on a microarray. In some embodiments, an "adapter" may comprise a sequencing adapter. In some embodiments, the sequencing adapter comprises a Y-shaped sequencing adapter or a bell-shaped sequencing adapter. In some aspects, the adapter comprises up to 20 random bases. In some aspects, the adapter comprises one or more unnatural nucleobases, or modified bases such as uracil and inosine. In some aspects, the adapter comprises at least one of a universal forward primer (UFP) and a universal reverse primer (URP). In some aspects, the adapter comprises a unique molecular identifier (UMI). In some aspects, the adapter comprises one or more backbone modifications selected from locked nucleic acid (LNA), peptide nucleic acid (PNA), glycol nucleic acid (GNA), phosphorothioate, 2'-fluoro-ribose, 2'-methoxy-ribose, phosphorodithioate, methylphosphonate, phosphoramidate, guanidinopropyl phosphoramidate, triazole, guanidinium, morpholino, threose nucleic acid (TNA) or hexitol nucleic acid (HNA). In some aspects, the adapter comprises one or more 3' or 5' modification groups, wherein the one or more 3' or 5' modification groups are independently selected from a dideoxyribose, a phosphate, an amine, an inverted base, a linker, or one or more other modifications.

Figure 4:
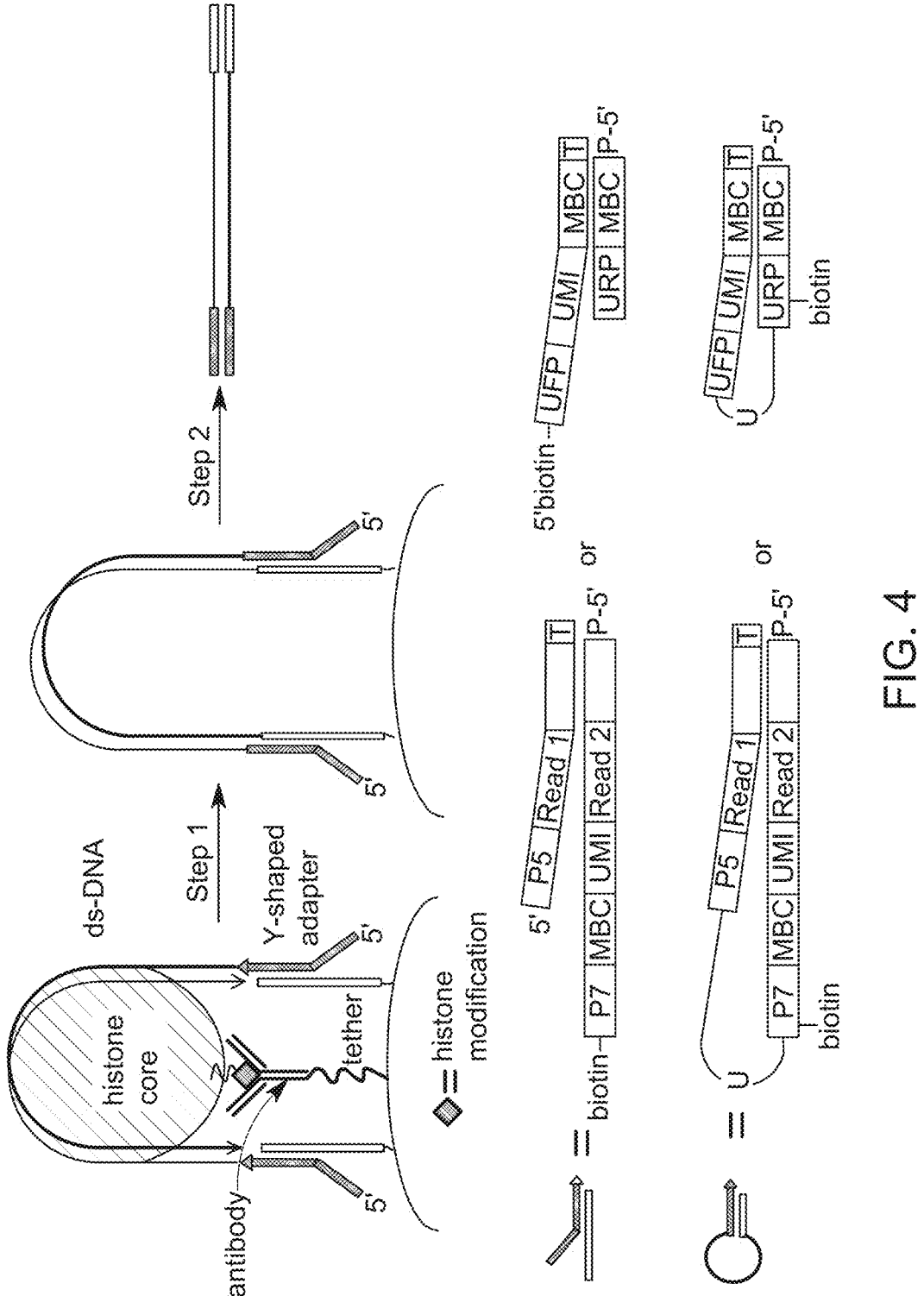
FIG. 4 shows a schematic of barcoding of nucleosomes by two-sided ligation of Y-shaped adapters, or alternatively, a bell-shaped adapter. "UMI" means unique molecular identifier. The adapters on the left recapitulate the Illumina P5 and P7 adapters where the MBC and UMI are sequenced as part of the index read. The adapters on the right introduce the MBC and UMI in frame with sequencing read 1 and the UFP and URP sites can be used to introduce sequences for other sequencing platforms than Illumina.

As shown in FIG. 4 substrate beads may comprise a modification-specific antibody and Y-shaped sequencing adapters. In some embodiments, the adapter is immobilized via a biotin-streptavidin interaction. In some embodiments, the adapter is immobilized via a biotin-avidin interaction or a biotin-neutravidin interaction. In some embodiments, modified nucleosomes or DNA binding proteins are captured by immunoprecipitation, followed by adapter ligation wherein the adapter contains a barcode that identifies the modification barcode (MBC), a unique molecular identifier (UMI), the primer binding sites for a sequencing read primer (Read1, Read2) and a forward (FSA) and reverse sequencing adapter (RSA). In some embodiments, the adapter contains a UMI, an MBC, the universal forward and reverse priming sites (UFP, URP). In some embodiments, the adapter may be additionally, or alternatively, a bell-shaped adapter. For example, to detect multiple histone targets in the same reaction, the corresponding bead types are combined, each exhibiting uniquely barcoded adapters and a modification-specific antibody (see, for example, FIG. 3A). As shown in FIG. 4, the histone core may be removed using a protease or denaturing conditions such as DTT and heat before performing PCR. In some aspects, the bell-shaped adapter may comprise a uracil (U) connecting the sequencing adapter elements of the adapter.

In some aspects, one or more elements, e.g., adapters or binding domains may be immobilized on a substrate using protein G, protein A, biotin, e.g., via avidin, streptavidin, or neutravidin, via a linker, or a recognition element.

The term "amplify", when used in reference to a nucleic acid, means producing copies of that nucleic acid. Nucleic acids may be amplified using, for example, polymerase chain reaction (PCR). Alternative methods for nucleic acid amplification include helicase-dependent amplification (LAMP), recombinase polymerase amplification (RPA), helicase-dependent amplification (HDA), multiple strand displacement amplification (MDA), nucleic acid sequence-based amplification (NASBA), self-sustained sequence replication (3SR), and rolling circle amplification (RCA).

As used herein the term "coupled" may be used to describe two or more components that are associated with one other. For example, a first component coupled to a second component may be bound covalently or non-covalently thereto, or otherwise linked. In some aspects, the binding domain may be coupled to a substrate using a tether.

As used herein the term "tether" means a bifunctional chemical moiety capable of attaching one component to another component. In some embodiments, a first component may be a substrate and a second component may be a binding domain.

As used herein the term "intra-complex adapter transfer" or "intra-complex barcode transfer" refers to transfer of an adapter and/or barcode to a target nucleic acid (i.e., a DNA), while a binding domain is bound thereto. Thus, in this context, the term "complex" refers to a complex formed between the target nucleic acid and its cognate binding domain.

As used herein, the terms "crosstalk", "barcode crosstalk", and similar terms refer to the off-target transfer of a nucleic acid barcode. For example, barcode crosstalk may occur when the barcode of a binding domain is transferred to a nucleic acid that is not bound to the binding domain of the binding domain.

The term "DNA address" refers to a DNA or RNA sequence and/or its complement that is used as a programmable binding element, to facilitate a specific binding event. For example, a nucleosome may be coupled to a nucleic acid sequence (i.e., a first DNA address) that binds to a nucleic acid sequence (e.g., a second DNA address) displayed by a substrate, immobilizing the nucleosome thereto.

The term "restriction sequence" means a sequence that is recognized by restriction enzyme specific to the restriction sequence.

Provided herein are adapters and binding domains, each of which are described in greater detail below.

Adapters

As used herein, the term "adapter" refers to any short nucleic acid sequence that can be coupled to the end of a DNA or RNA molecule and that confers some functionality. For example, in some embodiments, an adapter may facilitate sequencing and/or identification of a DNA or RNA molecule.

In some embodiments, the adapter comprises a 5' phosphate. In some embodiments, the adapter comprises a 3' phosphate. In some embodiments, the adapter comprises a 5' phosphate and a 3' phosphate. In some embodiments, an adapter is single-stranded. In some embodiments, an adapter is double-stranded. In some embodiments, a double-stranded adapter may comprise a single-stranded adapter hybridized to a complementary oligonucleotide.

In some embodiments, the adapter is coupled to the substrate covalently, via an affinity interaction, or a combination thereof. In some embodiments, the adapter comprises a moiety for surface anchoring. In some embodiments, the moiety for surface anchoring is biotin or desthiobiotin. In some embodiments, the moiety for surface anchoring is trans-cyclooctene (TCO), methyl-tetrazine (mTET), Dibenzocyclooctyl (DBCO), an amine, an azido or an alkyne.

In some embodiments, an adapter may be cleavable. For example, the adapter may comprise one or more cleavage sites. The cleavage site may comprise, for example, one or several uracil bases, a sequence recognized by an enzyme (e.g., a restriction enzyme or other nuclease), or a synthetic chemical moiety. In some embodiments, the adapter may be cleavable by an enzyme specific to a uracil, an inosine, an 8-oxoG, or a ribonucleoside of the adapter. For example, the adapter may be cleavable by 8-oxoguanine-DNA glycosylase, or a derivative thereof, a uracil-DNA glycosylase (UDG), endonuclease III, IV, V or VIII, or derivative thereof, or a ribonuclease, or derivative thereof. In some embodiments, the adapter comprises a recognition sequence, or restriction site, that may be cleaved by a restriction enzyme specific to the restriction site.

In some embodiments, an adapter comprises a universal forward primer (UFP). In some embodiments, an adapter comprises a universal reverse primer (URP). In some embodiments, an adapter comprises a UFP and a URP. In some embodiments, an adapter consists of a UFP or a URP. The UFP and URP sequences are DNA sequences that do not occur naturally, and allow for selective amplification of only those sequences that were introduced into a target nucleic acid (or copy thereof). During sequencing, the UFP and/or URP are annealed to the DNA target, to provide an initiation site for the elongation of a new DNA molecule (i.e., a copy thereof). A list of illustrative UFPs and URPs is shown in Table 1.

TABLE 1

| | | | SEQ ID NO. |
|---|---|---|---|
| No | Primer Name | Primer Sequence | |
| 1 | M13 Reverse (−27) | 5'-GGA AAC AGC TAT GAC CAT G-3' | 17 |
| 2 | M13 Forward (−41) | 5'-GGT TTT CCC AGTC ACG AC-3' | 18 |
| 3 | M13 Forward (−20) | 5'-GTA AAA CGA CGG CCA GTG-3' | 19 |
| 4 | M13 Forward (−21) | 5'-TGT AAA ACG ACG GCC AGT-3' | 20 |
| 5 | M13 Reverse (−48) | 5'-AGC GGA TAA CAA TTTC ACA C-3' | 21 |
| 6 | SP6 | 5'-TAC GAT TTA GGT GAC ACT ATA G-3' | 22 |
| 7 | T3 | 5'-CAA TTA ACC CTC ACT AAA GG-3' | 23 |
| 8 | T7 | 5'-TAA TAC GAC TCA CTA TAG GG-3' | 24 |
| 9 | T7 EEV | 5'-ATGTCGTAATAACCCCGCCCCG-3' | 25 |
| 10 | T7 Reverse | 5'-TAGTTATTGCTCAGCGGTGG-3' | 26 |
| 11 | T7 Term | 5'-GCT AGT TAT TGC TCA GCG G-3' | 27 |
| 12 | pBluescript KS | 5'-TCG AGG TCG ACG GTA TC-3' | 28 |
| 13 | pBluescript SK | 5'-CGC TCT AGA ACT AGT GGA TC-3' | 29 |
| 14 | 3'pGEX | 5'-CCG GGA GCT GCA TGT GTC AGA GG-3' | 30 |
| 15 | 5'pGEX | 5'-GGG CTG GCA AGC CAC GTT TGG TG-3' | 31 |
| 16 | GST-Tag | 5'-ACC CAA TGT GCC TGG ATG CG-3' | 32 |
| 17 | pTrcHis-Forward | 5'-GAG GTA TAT ATT AAT GTA TCG-3' | 33 |
| 18 | pTrcHis-Reverse | 5'-GAT TTA ATC TGT ATC AGG-3' | 34 |
| 19 | CMV-Forward | 5'-CGC AAA TGG GCG GTA GGC GTG-3' | 35 |
| 20 | CMV-Reverse | 5'-AGT AGG AAA GTC CCG TAA GG-3' | 36 |
| 21 | EGFP-C | 5'-CAT GGT CCT GCT GGA GTT CGT G-3' | 37 |
| 22 | EGFP-N | 5'-CGT CGC CGT CCA GCT CGA CCA-3' | 38 |
| 23 | BGH-Reverse | 5'-TAG AAG GCA CAG TCG AGG-3' | 39 |
| 24 | pQEproseq | 5'-CCC GAA AAG TGC CAC CTG-3' | 40 |
| 25 | pQErevseq | 5'-GTT CTG AGG TCA TTA CTG G-3' | 41 |
| 26 | Intein Forward | 5'-CCC GCC GCT GCT TTT GCA CGT GAG-3' | 42 |

TABLE 1-continued

UNIVERSAL PRIMER LIST

| No | Primer Name | Primer Sequence | SEQ ID NO. |
|----|-------------|-----------------|------------|
| 27 | 5'-pBabe-Seq | 5'-CTT TAT CCA GCC CTC AC-3' | 43 |
| 28 | 3'-pBabe-Seq | 5'-ACC CTA ACT GAC ACA CATT CC-3' | 44 |
| 29 | -96 g111 Sequencing Primer | 5'-CCC TCA TAG TTA GCG TAA CG-3' | 45 |
| 30 | GAL1 Forward | 5'-AAT ATA CCT CTA TAC TTT AAC GTC-3' | 46 |
| 31 | pBAD Forward | 5'-ATG CCA TAG CAT TTT TAT CC-3' | 47 |
| 32 | pBAD Reverse | 5'-GAT TTA ATC TGT ATC AGG-3' | 48 |
| 33 | pTRE 3' | 5'-CCA CAC CTC CCC CTG AAC-3' | 49 |
| 34 | pTRE 5' | 5'-CGC CTG GAG ACG CCA TCC-3' | 50 |
| 35 | pYESTrp Forward | 5'-GAT GTT AAC GAT ACC AGC C-3' | 51 |
| 36 | pYESTrp Reverse | 5'-GCG TGA ATG TAA GCG TGA C-3' | 52 |
| 37 | RVprimer3 | 5'-CTA GCA AAA TAG GCT GTC CC-3' | 53 |
| 38 | Rvprimer4 | 5'-GAC GAT AGT CAT GCC CCG CG-3' | 54 |
| 39 | G1primer 1 | 5'-TGT ATC TTA TGG TAC TGT AAC TG-3' | 55 |
| 40 | G1primer 2 | 5'-CTT TAT GTT TTT GGC GTC TTC CA-3' | 56 |
| 41 | SeqL-A (ATTL1) | 5'-GCG AGA GTA GGG AAC TGC-3' | 57 |
| 42 | SeqL-B (ATTL2) | 5'-AAC ATC AGA GAT TTT GAG ACA C-3' | 58 |
| 43 | SV40-pArev | 5'-CCT CTA CAA ATG TGG TAT GG-3' | 59 |
| 44 | SV40-Promoter | 5'-GCC CCT AAC TCC GCC CAT CC-3' | 60 |
| 45 | U6 Primer | 5'-GGG CAG GAA GAG GGC CTA T-3' | 61 |
| 46 | Xpress Forward | 5'-TAT GGC TAG CAT GAC TGG T-3' | 62 |
| 47 | EBV-Rev primer | 5'-GTG GTT TGT CCA AAC TCA TC-3' | 63 |
| 48 | hU6-01 | 5'-GAG GGC CTA TTT CCC ATG ATT-3' | 64 |
| 49 | hU6-02 | 5'-TAA TTA GAA TTA ATT TGA CT-3' | 65 |
| 50 | Illumina Truseq Read 1 | 5'-ACACTCTTTCCCTACACGACGCTCTTCCGATCT -3' | 66 |
| 51 | Illumina Truseq Read 2 | 5'-GTGACTGGAGTTCAGACGTGTGCTCTTCCGATCT-3' | 67 |

TABLE 1-continued

UNIVERSAL PRIMER LIST

| No | Primer Name | Primer Sequence | SEQ ID NO. |
|----|-------------|-----------------|------------|
| 52 | Illumina Nextera Read 1 | 5'-TCGTCGGCAGCGTCAGATGTGTATAAGAGACAG-3' | 68 |
| 53 | Illumina Nextera Read 2 | 5'-GTCTCGTGGGCTCGGAGATGTGTATAAGAGACAG-3' | 69 |
| 54 | Element Biosciences Read 1 | 5'-CGTGCTGGATTGGCTCACCAGACACCTTCCGACCAT-3' | 70 |
| 55 | Element Biosciences Read 2 | 5'-AGTTGACAAGCGGTAGCCTGCACACCTTCCGACAT-3' | 71 |
| 56 | Ion Torrent Primer A | 5'-CCATCTCATCCCTGCGTGTCTCCGACTCAG-3' | 72 |
| 57 | Ion Torrent Primer P | 5'-CCTCTCTATGGGCAGTCGGTGAT-3' | 73 |
| 58 | Oxford Nanopore Top strand | 5'-TTTTTTTTTTAATGTACTTCGTTCAGTTACGTATTG CT-3' | 74 |
| 59 | Oxford Nanopore Bottom strand | 5'-GCAATACGTAACTGAACGAAGT-3' | 75 |
| 60 | Pacific Biosciences Smart bell adapter | 5'-pATCTCTCTCTTTTCCTCCTCCTCCGTTGTTGTTGTT GAGAGAGAT-3' | 76 |

In some embodiments, universal primer sequences used in the adapters (and transferred to the target nucleic acid) are compatible with established DNA sequencing platforms and may be used to introduce surface adapters such as Illumina P5 and P7 in downstream PCR reactions.

In some embodiments, an adapter may comprise a barcode, such as a modification encoding barcode (MBC). An MBC is a short, unique nucleic acid sequence. Each MBC is used in connection with a specific epigenetic modification, to help with the identification and/or analysis thereof. For example, an MBC may be used in an adapter that is conjugated to a binding domain that is specific for a particular histone modification. In some embodiments, an adapter may consist of a barcode. In some embodiments, an adapter may consist of an MBC.

A nucleosome-binding conjugate comprises one or more adapter sequences. Each adapter sequence may comprise a universal sequence, a unique molecular identifier, a modification barcode and for spatial applications a spatial barcode. The spatial barcode indicates the spatial location of the nucleosome-binding conjugate on a microarray. For example, a microarray may comprise 10,000 spots, each spot exhibiting a plurality of nucleosome-binding conjugates. The nucleosome-binding conjugates within a spot share a spatial barcode, but may comprise different binding domains, where the modification barcode indicates that target of the binding domain. In some aspects, a spatial barcode is 5, 6, 7, 8, 9, 10, 11, 12, 13, 14, 15, 16, 17, 18. 19, 20, 25, 30, 35, 40 bases long.

In some embodiments, a plurality of nucleosome-binding conjugates with adapters comprising a unique spatial identifier are deposited on a microarray for the spatial analysis of histone modifications. Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array. Alternatively, specific spatial identifiers can be deposited at predetermined locations in an array of features during fabrication such that at each location, only one type of spatial identifier is present so that spatial identifiers are uniquely associated with a single feature of the array. Where necessary, the arrays can be decoded using any of the methods described herein so that spatial identifiers are uniquely associated with array feature locations, and this mapping can be stored as described above.

The present disclosure includes spatial barcoding methods involving labeling target molecules from individual cells or regions within a tissue with spatial barcodes. These barcodes are used to identify the origin of target molecules during sequencing to map histone modification patterns back to specific locations in the tissue. This spatial information is used to understand the functional organization of tissues and the roles of histone organization in various cellular contexts.

In some embodiments, an adapter comprises a universal sequence in addition to the barcode. As used herein "universal sequence" means a sequence that is not specifically associated with a binding domain or histone or nucleosome modification. For example, a universal sequence is a sequence that is antibody independent, including, but not limited to sequence adapters.

In some embodiments, the adapter comprises uracil bases, inosine bases, 8-oxo-G bases or ribonucleosides.

Histones are among the most highly conserved proteins that act as building blocks of the nucleosome, the fundamental structural and functional unit of chromatin. The nucleosome is an octamer, which is wrapped by ~147 bp of DNA, consisting of two copies of four core histone (H) H2A, H2B, H3, and H4 around, tied together by linker histone H1. These five classes of histone proteins, bearing over 60 different residues, constitute the major protein components of the chromatin and provide a tight packing of the DNA. Meanwhile, the histones contain a flexible N-terminus, often named the "histone tail", which can undergo various combinations of post-translational modifications, dynamically allowing regulatory proteins access to the DNA to fine tune almost all chromatin-mediated processes including chromatin condensation, gene transcription, DNA damage repair, and DNA replication. Transcriptionally active and silent chromatin is characterized by distinct post-translational modifications on the histones or their combinations. Histone proteins can undergo post-translational modifications by "writers" and "erasers," a set of enzymes responsible for the deposition and removal of the chemical modifications. Through different combinations and patterns of histone post-translational modifications, they can form the "histone code."

In some embodiments, an adapter may comprise a unique molecular identifier (UMI). A UMI consists of a short, random sequence that has $4^{[UMI\ Length]}$ unique variants. For example, a 10-base long UMI can encode 1,048,576 ($4^{10}$) unique molecules. UMIs are used for the absolute quantification of sequencing reads in order to correct for PCR amplification bias and errors. For example, an RNA sample may contain 100 copies of transcript A and 100 copies of transcript B. After PCR amplification, 1M copies of transcript A and 2M of transcript B may be detected, because transcript B amplifies more efficiently. UMI tagging, however, links 100 unique UMIs to A and 100 unique UMIs to B. When using a UMI for transcript A, 10,000 copies of 100 UMI variants will be detected, and for transcript B 20,000 copies of 100 UMI variants will be detected. Counting the number of UMI variants instead of counting the number of reads provides the absolute number of molecules.

Typically, a UMI length is chosen to avoid UMI collisions, defined as the event of observing two reads with the same sequence and same UMI but originating from two different genomic molecules. UMI collision is a function of the number of UMIs used, the number of unique alleles and the frequency of each allele in the population. The ideal length of UMIs also depends on the error rate of the sequencing platform and on the sequencing depth. Sequencing platforms with higher error rates require longer UMIs because errors in the UMI may cause accidental UMI collision. Targeted sequencing, wherein the sequencing depth for selected loci is greater than in whole genome sequencing, also uses longer UMIs because many alleles from different genomic molecules will share the same sequence. Excessively long UMIs are avoided because they require a greater number of sequencing cycles, thus shortening the read of the actual target sequence. Long UMIs may also cause mispriming in PCR reactions and produce sequencing artifacts. UMIs are typically in the range of about 3 to about 25 nucleotides. In some embodiments, a UMI is about 3 to about 20 nucleotides in length, such as about 3, about 4, about 5, about 6, about 7, about 8, about 9, about 10, about 11, about 12, about 13, about 14, about 15, about 16, about 17, about 18, about 19, or about 20 nucleotides in length. In some embodiments, the UMI may be 8 nucleotides in length. In some embodiments, the UMI may be 10 nucleotides in length.

FIGS. 2A-2B, FIG. 4, FIGS. 7A-7B, and FIG. 8 illustrate exemplary nucleic acid adapter architectures, and the legend provides a description of each element used therein.

Figure 2B:
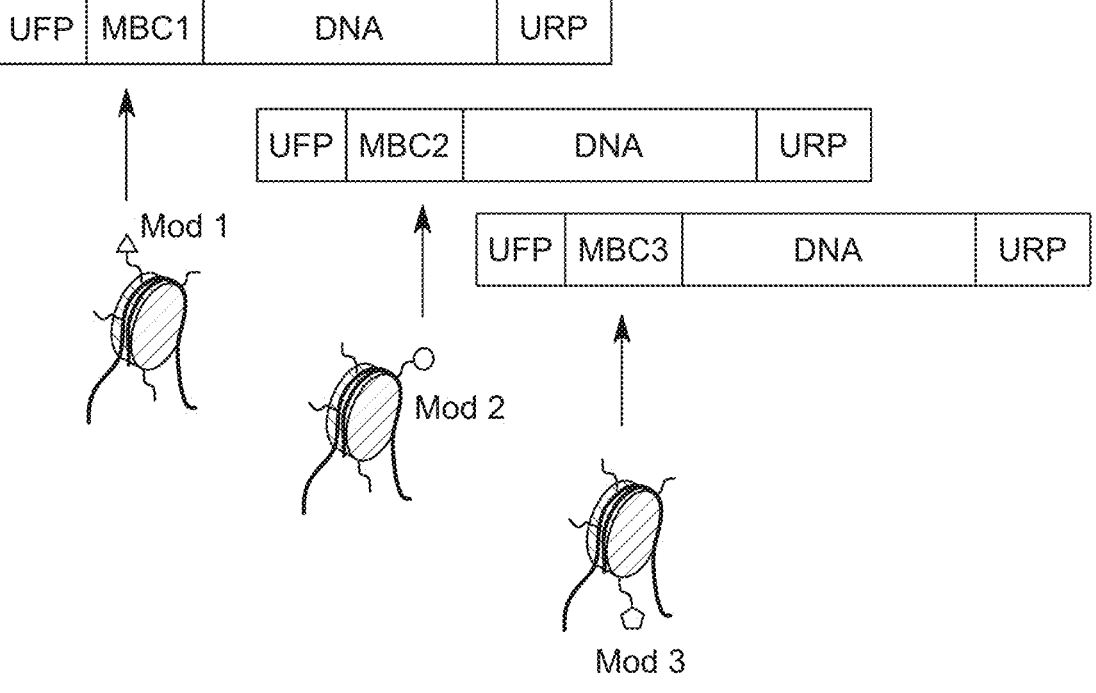

In some embodiments, the adapters shown in FIG. 2A are used in a co-localization assay that translates the presence of histone modifications (e.g. Mod1, Mod2, Mod3) into the corresponding modification barcodes (e.g. MBC1, MBC2, MBC3). The MBCs are enzymatically attached to the nucleosome DNA, together with universal forward (UFP) or reverse primer sites (URP). Sequencing of the resulting NGS library provides the histone modifications that are present in a nucleosome. In FIG. 2B, the targeted modifications are located on different nucleosomes as shown in the example. Each modification barcode (MBC) identifies a different histone modification. Transfer of the MBCs to the nucleosome DNA, together with universal forward (UFP) or reverse primer sites (URP), creates a sequencing library. Sequencing reveals the DNA sequence that is associated with a given histone and the associated histone modifications, as indicated by the modification barcodes.

In some embodiments, an adapter comprises a UFP, a URP, or a UFP and a URP. In some embodiments, an adapter comprises a UFP and/or a URP, and also comprises an MBC. In some embodiments, an adapter comprises a UFP and/or a URP, an MBC, and a UMI. In some embodiments, and adapter comprises a UFP and/or a URP, a MBC, and a UMI. In some embodiments, an adapter comprises a UFP and/or a URP, a MBC, and a UMI. In some embodiments, an adapter comprises a UFP, a URP, a UMI, and an MBC. In some embodiments, an adapter comprises a UFP, a UMI, and an MBC. In some embodiments, an adapter comprises a URP, a UMI, and an MBC. In some embodiments, an adapter comprises an MBC and a UMI. In some embodiments, an adapter comprises any of the configurations depicted in any of the figures.

In some embodiments, an adapter has a Y shape. In some embodiments, an adapter having a Y-shape comprises a UFP, an MBC, and a URP. In some embodiments, the adapter is partially double-stranded forming a Y-shape, where each single-stranded arm may comprise universal sequences, a modification barcode and a unique molecular identifier.

In some embodiments, an adapter has a bell-shape. In some embodiments, the adapter is partially double-stranded forming a bell-shape. In some embodiments, the single-stranded loop may comprise universal sequences, a modification barcode, and a unique molecular identifier.

In some aspects, the adapter according to one or more of the foregoing embodiments, is partially double-stranded with a single-stranded 3' and/or 5' overhang, or the adapter is partially double-stranded with single-stranded 3' and/or 5' overhangs on both sides. The adapter according to the foregoing embodiments, may comprise a double-stranded end that is either a blunt end or has a single 3'-base and/or 5'-base overhang.

The adapters described herein may, in some embodiments, comprise one or more linkers, such as linkers which help link the binding domain to the adapter. The linkers may comprise polyethylene glycol, hydrocarbons, peptides, DNA, or RNA. The linkers may vary in length. Longer linkers may be used in situations where a histone modification or DNA binding protein is located far from the 5' or 3' end of a nucleic acid sequence. Shorter linkers may be used in situations where a histone modification or DNA binding protein is located relatively close to a 5' or a 3' end of a nucleic acid sequence.

In some embodiments, the adapters, or a linker sequence contained therein, are cleavable. For example, the adapters may comprise one or more cleavage sites. The adapter may be chemically, photochemically or enzymatically cleavable. The cleavage sites may comprise, for example, one or several uracil bases, a sequence recognized by an enzyme (e.g., a uracil-DNA glycosylase, restriction enzyme or other nuclease), or a synthetic chemical moiety, for example disulfides, carbonate ester, hydrazones, cis-aconityl, or β-glucuronide.

As described in further detail below, adapters may be fused to a single- or double-stranded target nucleic acid (e.g., a DNA or RNA) using a barcode transfer reaction.

A "universal connector" as used herein means a sequence that can hybridize to a complimentary sequence on any adapter. In some embodiments, a universal connector may be a poly-A oligonucleotide sequence, for example, a sequence that can be created using dATP and the action of a terminal nucleotidyl transferase. In this example, the poly-A universal sequence can be hybridized to an oligo-T sequence included in a connected adapter.

Figure 8:
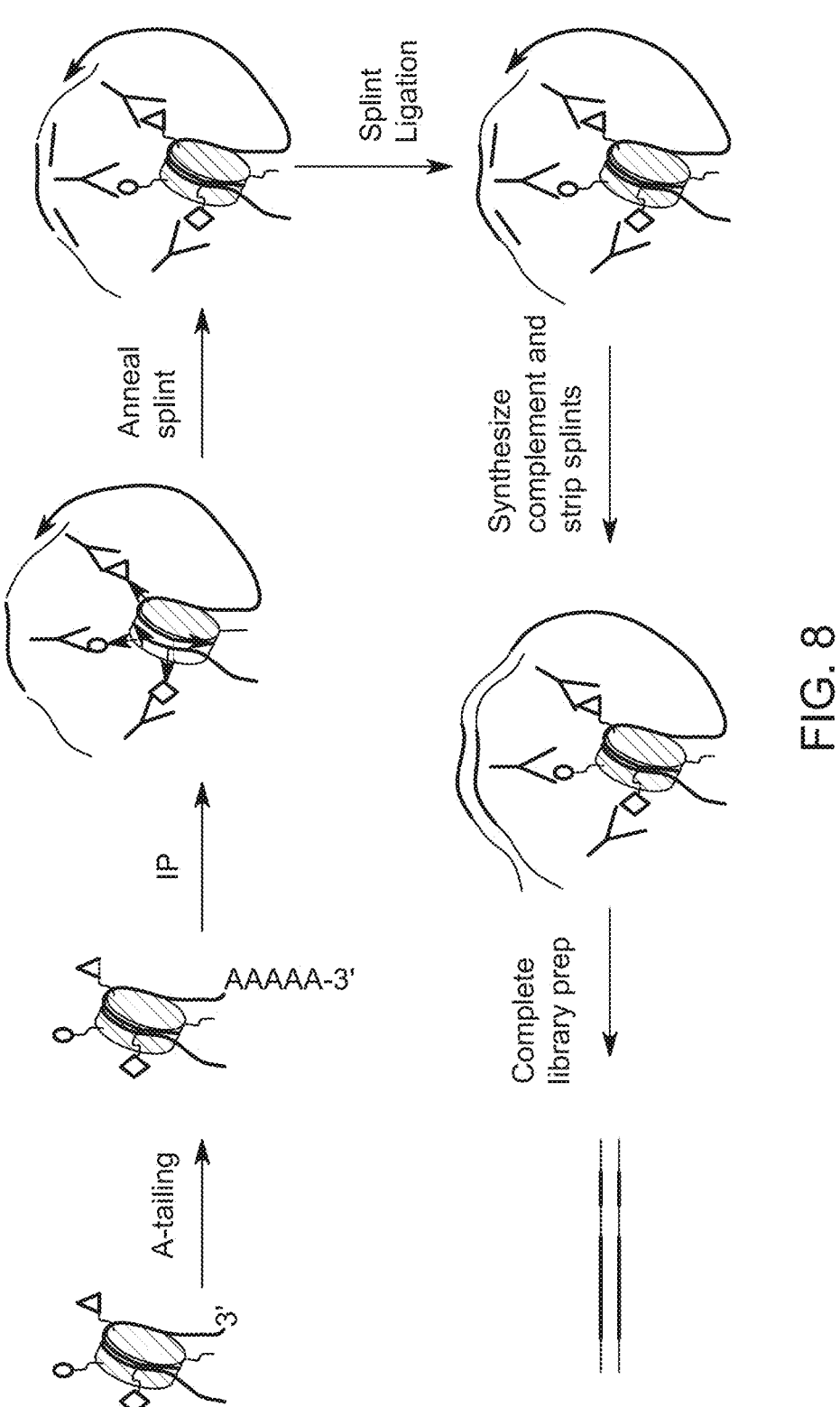
FIG. 8 shows co-localization of histone modifications by proximity ligation. Multiple nucleosome-binding conjugates bind to the same nucleosome. Proximal adapters are connected by splint ligation and appended to the nucleosomal DNA by primer extension.
Figure 8:
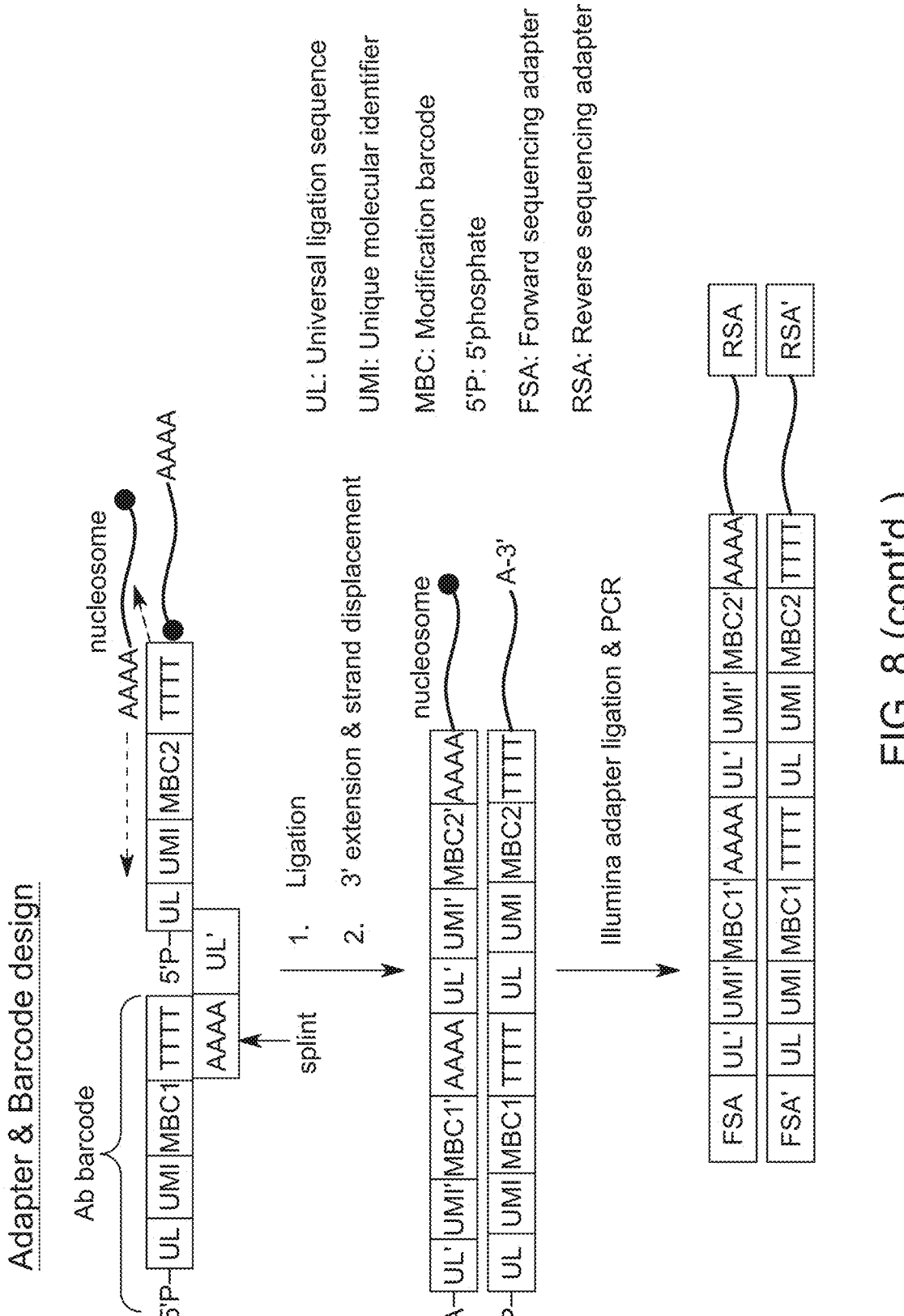

In some embodiments, a 3'poly-A tail is appended to a target as depicted in FIG. 8. The 3'poly-A tail is appended by polyadenylation using any known terminal nucleotidyl transferase (TD). In some embodiments, the length of the 3'poly-A tail is about 5, about 10, about 15, about 20, about 25, about 30, about 35, about 40, about 45, about 50, about 55, or about 60 bases in length.

In some embodiments, primer extension comprises appending a 3'poly-T tail, a 3'poly-G tail, a 3'poly-A tail or a 3'poly-G tail to an DNA target. In some embodiments, the length of the tail is about 5, about 10, about 15, about 20, about 25, about 30, about 35, about 40, about 45, about 50, about 55, or about 60 bases in length.

Binding Domains

As used herein, the term "binding domain" refers to any nucleic acid, polypeptide, or other macromolecule that binds to a histone modification of a target nucleosome or a DNA binding protein. The term "binding domain" may be used interchangeably herein with the terms "binder," "recognition element," "antibody," etc., as will be understood from context by those of skill in the art. In some embodiments, a binding domain binds to a histone modification. In some embodiments, the binding domain does not bind to any nucleic acid features flanking the histone modification. In some embodiments, a binding domain binds to a histone modification or a DNA binding protein. In some embodiments, the binding domain may bind a conserved sequence motif. In some embodiments, the binding domain does not bind to any nucleic acid features flanking the histone modification or flanking the DNA binding protein. In some embodiments, the binding domain binds to a histone modification that is a methylation, citrullination, acetylation, ubiquitination, or a sumoylation of lysine or arginine. In some embodiments, the binding domain binds to a phosphorylation of a tyrosine, serine, or threonine. In some embodiments, the binding domain binds to a DNA binding protein that is a transcription factor, or an RNA polymerase.

The binding domains described herein may be any protein, nucleic acid, or fragment or derivative thereof that is capable of recognizing and binding to a histone modification or a DNA binding protein. For example, in some embodiments, the binding domain comprises an antibody, an aptamer, a reader protein, a writer protein, an eraser protein, an engineered macromolecule scaffold, an engineered protein scaffold, or a selective covalent capture reagent, or a fragment or derivative thereof. In some embodiments, the binding domain comprises an IgG antibody, an antigen-binding fragment (Fab), a single chain variable fragment (scFv), or a heavy or light chain single domain ($V_H$ and $V_L$). In some embodiments, the binding domain comprises a heavy-chain antibody (hcAb) or the $V_HH$ domain of a hcAb (nanobody). In some embodiments, the binding domain is a bivalent binding domain directed at histone modification(s). In some embodiments, the binding domain comprises an engineered protein scaffold such as an adnectin, an affibody, an affilin, an anticalin, an atrimer, an avimer, a bicyclic peptide, a centyrin, a cys-knot, a darpin, a fynomer, a kunitz domain, an obody or a pronectin. In some embodiments, the binding domain comprises a catalytically inactive variant of a DNA or histone writer or eraser protein. In some embodiments, the binding domain is attached to the substrate covalently or via an affinity interaction. Affinity interactions are interactions where two binding partners display a binding affinity towards each other. Examples of affinity interactions, include, but are not limited to, a biotin-avidin interaction or an antibody-protein G interaction.

IgG antibodies are the predominant isotype of immunoglobulins. IgGs comprise two identical heavy chains and two identical light chains that are covalently linked and stabilized through disulfide bonds. IgGs recognize an antigen via the variable N-terminal domains of the heavy ($V_H$) and the light ($V_L$) chain and six complementarity determining regions (CDRs). Antibodies that bind to histone modifications or DNA binding proteins are available commercially, for example from EpigenTek, Abcam, and Active Motif.

Antibodies that bind to histone modifications or DNA binding proteins also can be developed according to methods known and practiced by persons of ordinary skill in the art. In some embodiments, the antibodies may be monoclonal antibodies, polyclonal antibodies, or functional fragments or variants thereof. The term "antibody" as used herein covers any specific binding substance having a binding domain with the required specificity. Thus, this term covers antibody fragments, derivatives, functional equivalents, and homologues of antibodies, including any polypeptide comprising an immunoglobulin binding domain, whether natural or synthetic, monoclonal or polyclonal. Chimeric molecules comprising an immunoglobulin binding domain, or equivalent, fused to another polypeptide are also included.

In some embodiments, the binding domain may comprise a nanobody. Nanobodies comprise a single variable domain ($V_HH$) of heavy chain antibodies, as produced by camelids and several cartilaginous fish. The $V_HH$ domain comprises three CDRs that are enlarged compared to the CDRs of IgG antibodies, and provide a sized antigen-interacting surface that is similar in size compared to that of IgGs (i.e., about 800 Å$^2$). Nanobodies bind antigens with similar affinities as IgG antibodies, and offer several advantages relative thereto: they are smaller (15 kDa), less sensitive to reducing environments due to fewer disulfide bonds, more soluble, and devoid of post-translational glycosylation. Nanobodies can be produced in bacterial expression systems, and they are therefore amenable to affinity and specificity maturation by phage and other display techniques. Other advantages include improved thermal stability and solubility, and straightforward approaches to site-specific labeling. Due to their small size, nanobodies can form convex paratopes making them suitable for binding difficult-to-access antigens. Illustrative methods for producing nanobodies include immunizing the respective animal (e.g., a camel) with the antigen of interest, by further evolving an existing naïve library, or by a combination thereof.

In some embodiments, the binding domain comprises a reader protein, a writer protein or an eraser protein. A "reader protein" is a protein that selectively recognizes and binds specific chemical modifications on histone tail. A "writer protein" is a protein that adds specific chemical modifications to a histone tail. An "eraser protein" is an enzyme which removes specific chemical modifications from a histone tail. In some embodiments, the binding domain comprises a fragment or derivative of a reader protein, a writer protein, or an eraser protein. In some embodiments, the binding domain comprises an engineered form of a reader, writer, or eraser protein, such as a form which has been engineered to retain nucleic acid binding but lacks any enzymatic activity. In some embodiments, the writer protein is a histone acetyltransferase, a CBP/P300 protein, a lysine methyltransferase, an arginine methyltransferase. In some embodiments, the reader comprises a Methyl-CpG-binding domain (MBD), bromodomain adjacent to the zinc finger proteins (BAZ), bromodomain (BRD), malignant brain tumor (MBT), plant homeodomain finger (PHD), chromatin binding (chromo), proline-tryptophan-tryptophan-proline domain (PWWP), tryptophan-aspartic acid dipeptide repeat domain (WD40), Ankyrin repeats, or tudor domain. In some embodiments, the eraser protein is a histone deacetylase, histone lysine demethylase, or histone arginine demethylase. Further, illustrative reader, writer, and eraser proteins that may be used in the binding domains described herein are listed in Table 2. Additional reader, writer, and eraser proteins are listed at the following world wide web address: rnawre.bio2db.com, and are incorporated herein by reference.

TABLE 2

Reader, writer, and eraser proteins

| Type | Family | Specific Protein Examples |
|---|---|---|
| Writer | Methyltransferase | CBP/P300 protein, a lysine methyltransferase, an arginine methyltransferase, a histone acetyltransferase |
| Eraser | Demethylases and deacetylases | A histone deacetylase, histone lysine demethylase, histone arginine demethylase |
| Reader | Chromatin-associated protein domains | MBD, BAZ, BRD, MBT, PHD, chromo, PWWP, WD40, bromo domain or tudor domain |

TABLE 3

Histone Modifications

| Site | Enzyme | Function |
|---|---|---|
| Histone H2A Modifications | | |
| K5ac | Tip60, p300/CBP, Hat1 | Transcriptional activation |
| K9bio | HCS | Acetylation and methylation dependent |
| | Biotinidase | Involved in cell proliferation, gene silencing, and cellular response to DNA damage |
| K7ac | Hat1, Esa1 | Transcriptional activation |
| K13bio | HCS | Acetylation and methylation dependent |
| | Biotinidase | Involved in cell proliferation, gene silencing, and cellular response to DNA damage |
| K13ub | Rnf168 | Part of the DNA damage response to double-stranded DNA breaks |
| K15ub | Rnf168 | Part of the DNA damage response to double-stranded DNA breaks |
| K63ub | Rnf8 | Part of the DNA damage response to double-stranded DNA breaks |
| Q105me | Nop1, fibrillarin: me1 | Ribosomal gene expression |
| K119ub | dRing, RING1B | Polycomb silencing UV damage response |
| S121ph (S122ph) | Mec1 | DNA damage response |
| | PIKK | Telomere silencing |
| | Bub1 | Chromosomal stability |
| T125ph | Mec1 | DNA damage response |
| | PIKK | Telomere silencing |
| K126bio | HCS | Acetylation and methylation dependent |

TABLE 3-continued

| Histone Modifications | | |
| --- | --- | --- |
| Site | Enzyme | Function |
| | Biotinidase | Involved in cell proliferation, gene silencing, and cellular response to DNA damage. |
| K126su | | Transcriptional repression Blocks histone acetylation and histone ubiquitination |
| K127bio | HCS | Acetylation and methylation dependent |
| | Biotinidase | Involved in cell proliferation, gene silencing, and cellular response to DNA damage |
| S128ph | Mec1 | DNA damage response |
| (S129ph) | PIKK | Telomere silencing |
| K130bio | HCS | Acetylation and methylation dependent |
| | Biotinidase | Involved in cell proliferation, gene silencing, and cellular response to DNA damage |
| S1ph | | |
| R3me3 | | |
| K5hib | | |
| K9me1; me2; suc; hib | | |
| R11me1, me2 | | |
| K13me1, ac; suc | | |
| K15ac | | |
| K21suc | | |
| R29me1, me2 | | |
| K36ac, suc; for; hib; cr | | |
| Y39oh | | |
| R42me1 | | |
| R71me1 | | |
| K74ac, me1; hib | | |
| K75me1; hib | | |
| R77me1 | | |
| T79ac | | |
| R88me1 | | |
| K95cr, but, pr, me1, me2; for; ub; suc; hib | | |
| K99me1; me2 | | |
| T101og | | |
| K118for, me1, cr; for; ub, me2; hib | | |
| K119cr; mal | | |
| T120ph | | |
| K125me1, cr; me2, pr; ub | | |
| K127ac | | |
| K129ac | | |
| Histone H2AX Modifications | | |
| K13ub | Rnf168 | Part of the DNA damage response to double-stranded DNA breaks |
| K15ub | Rnf168 | Part of the DNA damage response to double-stranded DNA breaks |
| K63ub | Rnf8 | Part of the DNA damage response to double-stranded DNA breaks |
| S139ph | ATM | DNA repair |
| | DNA-PK | M-phase related |
| | ATR | Also known as γH2AX |
| Y142ph | WSTF | DNA damage |
| K118ub | | |
| K119ub | | |
| Histone H2B Modifications | | |
| K5ac | | Transcriptional activation |
| S10ph | Ste20 | Apoptosis |
| S14ph | Mst1/krs2 kinase | Apoptosis Somatic hypermutation and class switch recombination |
| K16su | | Gene repression |
| K17su | | Gene repression |

TABLE 3-continued

| Histone Modifications | | |
| --- | --- | --- |
| Site | Enzyme | Function |
| S33ph | CTK<br>TAF1 | Transcriptional activation |
| K34ub | MSL2 | Transcriptional activation |
| K120ub | RNF20/40 | Cell-cycle progression in concert with SAGA for transcriptional activation through H3 methylation, DNA damage response, meiosis |
| K123ub | Rad6(E2)<br><br>Bre1(E3); ub1 | Telomeric silencing by lowering histone methylation at H3K4 and H3K79 |
| E2arn | | |
| K5me1; cr; for; hib; suc | | |
| S6ph | | |
| K11ac; cr | | |
| K12me1, cr; me3; hib | | |
| K15ac; me1, cr | | |
| K16ac; cr | | |
| T19ac | | |
| K20me1, cr; hib | | |
| K21but | | |
| K23me1, cr; me2; hib | | |
| K24hib | | |
| K34for; cr; suc; me1; hib | | |
| S36og | | |
| K37me1 | | |
| E38me2 | | |
| Y37oh | | |
| K43me1; for; hib; suc | | |
| K46for; suc; hib | | |
| K57me1; ac; hib | | |
| E64me2 | | |
| S76ph | | |
| K79me1 | | |
| K85ac; me1; suc; hib | | |
| S88ph | | |
| T89ph | | |
| S92ph | | |
| K99me1 | | |
| K108for; cr; ub, ac; hib; suc | | |
| S113ph | | |
| K116for, me1; suc, mal; ac; hib; cr | | |
| K120for; suc; ac, ub; hib | | |
| K125ac | | |
| Histone H3 Modifications | | |
| R2me | CARM1; me1, me2a<br>PRMT5; me1, me2s<br>PRMT6; me1, me2a<br>PRMT7; me1, me2s | Gene expression |
| T3ph | Haspin | Centromere mitotic spindle function |
| K4ac | GCN5, RTT109, Sir2, Hst1 | Transcription activation at some promoters |
| K4me | Set1; me3<br><br>Set-2; me1-3<br>Set1; me2/3<br>SETD1A; me1-3<br><br>SETD1B<br><br>Trx<br>MLL; me1-3<br>MLL2<br>Trr<br>MLL3; me1-3<br>MLL4 | rDNA/telomeric silencing (Sc)<br>Germ cell maintenance<br><br>Transcriptional activation (All)<br><br>Transcriptional activation<br>Trithorax activation<br>Gene activation<br><br>Enhancer function |

TABLE 3-continued

| | Histone Modifications | |
| --- | --- | --- |
| Site | Enzyme | Function |
| | Ash-2; me1-3 | Germ cell specification |
| | Ash1; me3 | Trithorax activation |
| | ASH1L; me1/3 | Gene activation |
| | SETD7; me1 | Transcriptional activation |
| | SMYD3; me2/3 | Transcriptional activation |
| | Meisetz; me3 | Meiotic prophase progression |
| T6ph | PKCβ | Inhibits AR-dependent transcription |
| R8me | PRMT5; me1, me2s | Transcriptional repression |
| K9ac | SAGA | Transcriptional activation |
| | GCN5 | |
| | SRC1 | Nuclear receptor coactivator Transcriptional activation |
| K9me | Clr4; me1, me2 | Centromeric and mating-type silencing |
| | Dim5; me3 | DNA methylation |
| | Met-2; me3 | Germ cells |
| | Mes-2; me3 | |
| | Su(var)3-9; me2/3 | Dominant PEV modifier |
| | KRYPTONITE; me2 | DNA methylation |
| | Suv39h1; me2/3 | Pericentric heterochromatin |
| | Suv39h2; me2/3 | |
| | SUV39H1; me3 | Rb-mediated silencing |
| | ESET; me2/me3 (SETDB1) | Transcriptional repression |
| | G9a; me1/me2 | Transcriptional repression Imprinting |
| | EHMT1/GLP; me1/me2 | Transcriptional repression |
| | PRDM2/RIZ1; me2 | Tumor suppression and response to female sex hormones |
| S10ph | Snf1 | Transcriptional activation |
| | Jil-1 | Transcriptional up-regulation of male X-chromosome |
| | Rsk2 | Transcriptional activation of immediate early genes (in concert with H3-K14 acetylation) |
| | Msk1 | |
| | Msk2 | |
| | IKKα | Transcriptional up-regulation |
| | Ip11/AuroraB | Mitotic chromosome condensation |
| | NIMA | Mitotic chromosome condensation |
| | Fyn kinase | UVB-induced MAP kinase pathway |
| T11ph | Dlk/ZIP | Mitosis-specific phosphorylation |
| K14ac | Gcn5 | Transcriptional activation |
| | $TAF_{II}230$ | Transcriptional activation |
| | $TAF_{II}250$ | |
| | p300 | Transcriptional activation |
| | PCAF | Transcriptional activation |
| | SRC1 | Nuclear receptor coactivator |
| R17me | CARM1; me1, me2a | Transcriptional activation (in concert with H3-K18/23 acetylation) |
| K18ac | SAGA | Transcriptional activation |
| | Ada | |
| | GCN5 | |
| | p300 | Transcriptional activation |
| | CBP | Transcriptional activation (in concert with H3-R17 methylation) |
| K23ac | SAGA | Transcriptional activation |
| | CBP | Transcriptional activation (in concert with H3-R17 methylation) |

TABLE 3-continued

| Histone Modifications | | |
|---|---|---|
| Site | Enzyme | Function |
| R26me | CARM1; me1, me2a | In vitro methylation site |
| K27ac | CBP, P300, GCN5 | Enhancer function, gene expression |
| K27me | E(z)/EZH2; me3 | Polycomb repression Early B-cell development X-chromosome inactivation |
| S28ph | Aurora-B | Mitotic chromosome condensation |
| | MSK1 | UVB-induced phosphorylation |
| K36me | Set2; me2 | Gene repression |
| | Set2; me2 | Transcription activation |
| | Set2; me2 | Transcription elongation |
| | MES-4; me2 | Dosage compensation in germline |
| | MET-1; me3 | Meiosis |
| | MES4; me3 | Transcription elongation |
| | SET2; me3 | |
| | SETD2; me1-3 | Transcription activation |
| | NSD1-3; me1, me2 | |
| K36ac | GCN5 | Promoter mark on active genes |
| P38iso | Fpr4 | Gene expression |
| Y41ph | JAK2 | Gene expression |
| R43me | CARM1, PRMT6; me2a | Transcriptional activation |
| T45ph | Cdc7, PKC | DNA replication; apoptosis |
| K56ac | SPT10 | Transcriptional activation; DNA damage |
| K56me | G9a; me1 | DNA replication |
| | Suv39h; me3 | Heterochromatin |
| K64ac | p300 | Nucleosome dynamics and transcription |
| K64me | me3 | Pericentric heterochromatin |
| K79me | Dot1/DOT1L; me1-3 | Telomeric silencing, pachytene checkpoint DNA damage response |
| T80ph | | Mitosis |
| K4cr; hib; ac | | |
| T6ac | | |
| K9cr; hib | | |
| S10ac; og | | |
| K14suc; but; hib | | |
| K18cr; for; me1; hib | | |
| T22ac | | |
| K23cr; for; pr; hib; suc | | |
| K27cr; but; hib; suc | | |
| S28ac | | |
| T32og | | |
| K36hib | | |
| R52me1 | | |
| R53me1 | | |
| Y54ac | | |
| K56cr, for; suc, mal; pr; ub; hib | | |
| E59me2 | | |
| R63me1 | | |
| K64for; hib; ac, me1 | | |
| K79suc; for; cr; ub; hib; ac | | |
| T80ac | | |
| R83me1, me2 | | |
| S86ph | | |
| T107ph | | |
| C110gt | | |
| K115ac; but | | |
| T118ph | | |
| R128me1 | | |
| K122suc; for; me2; hib; cr | | |
| K134me1 | | |
| Histone H3.3 Modifications | | |
| K4me | me1, me2, me3 | Transcriptional activation |
| K9me | me1, me2 | Transcriptional repression |
| K9ac | | Transcriptional activation |
| K14me | me1, me2 | |

TABLE 3-continued

| Histone Modifications | | |
| --- | --- | --- |
| Site | Enzyme | Function |
| K14ac | | Transcriptional activation |
| K18ac | | Transcriptional activation |
| K23ac | | Transcriptional activation |
| K27me | me1, me2, me3 | Transcriptional repression |
| S31ph | | Mitosis-specific phosphorylation |
| K36me | me1, me2, me3 | Transcriptional activation |
| K37me | me1, me2 | |
| K79me | me1, me2 | Transcriptional activation |
| Histone CEN-H3/CENP-A Modifications | | |
| G1me3 | RCC1 | Mitosis |
| S7ph | | Mitosis |
| S16ph | | Chromosome segregation during mitosis |
| S18ph | | Chromosome segregation during mitosis |
| Histone H4 Modifications | | |
| S1ph | Casein kinase II | DNA damage response |
| R3me | PRMT1; me1, me2a | Transcriptional activation |
| | PRMT5; me1, me2s | |
| | PRMT6; me1, me2a | |
| | PRMT7; me1, me2s | |
| K5ac | Hat1 | Histone deposition |
| | Esa1/NuA4 | Cell-cycle progression |
| | ATF2 | Sequence-specific transcription factor |
| | p300 | Transcriptional activation |
| K5me | Smyd3; me1 | Contributes to cancer phenotype |
| K8ac | Y-ATF2 | Excluded from Xi Sequence-specific transcription factor |
| | PCAF/p300 | Transcriptional activation |
| K8me | SET5; me1 | Stress response |
| K12ac | Hat1 | Excluded from Xi Histone deposition |
| | NuA4 | Mitotic and meiotic progression |
| K12me | SET5; me1 | Stress response |
| K12bio | HCS | Decrease in response to DNA double-strand breaks |
| | Biotinidase | Effects on cell proliferation |
| K16ac | | Excluded from Xi Cell-cycle-dependent acetylation |
| | MOF | Transcriptional up-regulation of male X chromosome |
| | ATF2 | Sequence-specific transcription factor |
| K20me | Suv4-20h1; me2, me3 | Gene silencing |
| | Suv4-20h2; me2, me3 | |
| | SETD8/Pr-SET7; me1 | Transcriptional silencing Mitotic condensation |
| | Ash1; me2 | Trithorax activation in concert with H3K4 and H3K9 methylation |
| K59me | | Silent chromatin formation |
| K59su | SUMO-1 | Transcriptional repression |
| | SUMO-3 | |
| R3me3 | | |
| K5cr; me3; pr, but; hib | | |
| K8cr; pr, but; hib | | |
| K12cr; for; suc; pr, but; hib | | |
| K16cr, me1; pr; pr, but; hib | | |
| R17me1, me2 | | |
| R17me1, me2, me3 | | |
| K20ac | | |
| K31for; suc; hib; me1; pr | | |
| R23me3 | | |
| R35me1 | | |
| K44pr; hib | | |
| S47og; ph | | |
| Y51oh | | |

TABLE 3-continued

| Histone Modifications | | |
|---|---|---|
| Site | Enzyme | Function |
| R55me1 | | |
| K59mel, for; hib | | |
| R67me1 | | |
| K77me1; suc; for; hib; ac; pr; cr | | |
| K79for; suc, ac; hib; pr | | |
| Y88ox; ph | | |
| K91ac; for; suc; cr; hib; pr | | |
| R92me1 | | |
| Histone H1 Modifications | | |
| E2arn | PARP-1; ar1 | Involved in neurotrophic activity |
| T10ph | | Mitosis specific Transcriptional activation H1b |
| E14arn | PARP-1; ar1 | Involved in neurotrophic activity |
| S17ph | | Interphase specific Transcriptional activation H1b |
| K26me | EZH2; me2 | Mediates HP1 binding |
| S27ph | EZH2; me2 | Blocks HP1 binding |
| R54cit | PADI4 | Cellular reprogramming/nucleosome binding |
| T137ph | | Mitosis specific Transcriptional activation H1b |
| T154ph | | Mitosis specific Transcriptional activation H1b |
| S172ph | | Interphase specific Transcriptional activation H1b |
| S188ph | | Interphase specific Transcriptional activation H1b |
| K213ar | PARP-1; ar1 | Involved in neurotrophic activity |
| S1ph | | |
| E2arn | | |
| T3ph | | |
| K12me1 | | |
| E14arn | | |
| K16ac; me1, me2; for | | |
| T17ph | | |
| K21ac; me1 | | |
| K22hib | | |
| K25hib | | |
| K26hib | | |
| S30ph | | |
| K33ac; me2, for; cr; ub; hib | | |
| S35ph; ac | | |
| K45ac, ub; hib; for; suc | | |
| K48ac | | |
| S50ac | | |
| K51ac; me1; hib | | |
| K54me1 | | |
| K62ac; for; hib; suc | | |
| K63ac; me1; for; cr; hib | | |
| K64ac | | |
| K66for | | |
| S72ph | | |
| Y73oh | | |
| K74for; hib | | |
| K80hib | | |
| K81me1 | | |
| K83for | | |
| K84for; cr; hib | | |
| K85ac | | |
| S87ph[a] | | |
| K87for[a] | | |
| K89ac, for; cr; suc; hib | | |
| K92me1 | | |
| K96ac; me1; me2; for; cr; hib; suc | | |

TABLE 3-continued

| Histone Modifications | | |
| --- | --- | --- |
| Site | Enzyme | Function |
| K101me1 | | |
| K105me1; suc | | |
| K107me1 | | |
| K109me2; for; hib | | |
| S112ac | | |
| K118me1 | | |
| K120hib; suc | | |
| K128hib | | |
| K131me1 | | |
| K135hib | | |
| K140for | | |
| T145ph | | |
| T146ph | | |
| K147me1; hib | | |
| K150me1 | | |
| K158cr; hib | | |
| K159for | | |
| T164ph | | |
| K167cr; hib | | |
| T179ph | | |
| K187me1 | | |
| K201me1 | | |
| K212hib | | |
| K226me1 | | |
| Histone H2A.Z Modifications | | |
| 4ac; me1 | | |
| K7ac; me1 | | |
| K11ac | | |
| K13ac | | |
| K120ub | | |
| K121ub | | |
| K125ub | | |
| Histone macroH2A Modifications | | |
| K17me1 | | |
| K115ub | | |
| K122me2 | | |
| T128ph | | |
| K238me1 | | |
| K238me2 | | |

Binding domains may be selected and/or engineered to bind to any histone modification or DNA binding protein. For example, the histone modification may be an acetylation, a methylation, a citrullination, a phosphorylation, a ubiquitylation (also referred to as ubiquitination), a sumoylation, an ADP ribosylation, a deamination, or a proline isomerization. In some embodiments, the histone modification is sumoylation of lysine or arginine. In some embodiments, the histone modification is a phosphorylation of tyrosine, serine, and threonine. In some embodiments, the DNA binding protein is a transcription factor, histone-protein complex or one or more histone subunits, or a transcriptional repressor. Binding domains may be selected and/or engineered to bind to any modification, e.g., an acetylation, a methylation, a citrullination, a phosphorylation, a ubiquitylation (also referred to as ubiquitination), a sumoylation, an ADP ribosylation, a deamination, or a proline isomerization, or a DNA binding protein of a nucleosome.

Target DNA

As used herein, the term "target DNA" refers to nucleic acid sequences associated with a histone modification or a DNA binding protein of interest. In some embodiments, the target DNA may be DNA of the nucleosome comprising a histone modification. In some embodiments, the target DNA comprises nucleosome ends. In some embodiments, the methods according to one or more embodiments comprises end-repairing and/or A-tailing the nucleosome ends.

DNA Binding Protein

As used herein, the term "DNA binding protein" refers to proteins that have a general or specific affinity for single- or double-stranded DNA. In some embodiments, a DNA binding protein may be a protein associated with a nucleosome. For example, a DNA binding protein may be a protein that binds to the DNA between or associated with a nucleosome. In some embodiments, the DNA binding protein is a transcription factor. In some embodiments, the DNA binding protein is RNA polymerase II. In some embodiments, the DNA binding protein is a transcriptional activator or a transcriptional repressor.

Adapter/Barcode Transfer Reactions

The binding domains described herein may be used to transfer an adapter to a target nucleic acid, such as an adapter comprising a barcode. Thus, in some embodiments, the binding domains described herein may be used to transfer a barcode to a target nucleic acid. The barcode may be a MBC, i.e., a barcode that is unique to the histone modification and is conjugated to target DNA of the nucleosome comprising the histone modification or DNA binding protein. A target nucleic acid to which an adapter has been transferred is referred to herein as a "labeled target nucleic acid," a "labeled target" or similar terms. A target nucleic acid to which a barcode has been transferred is referred to herein as a "barcoded target nucleic acid," a "barcoded target" or similar terms. A reaction in which an adapter is transferred to a target nucleic acid is referred to herein as an "adapter transfer reaction." Similarly, a reaction in which a barcode is transferred to a target nucleic acid is referred to herein as a "barcode transfer reaction."

In some aspects, a barcode is transferred to the target nucleic acid by enzymatic transfer, e.g., enzymatically by single stranded ligation, splint ligation, primer extension, or double-stranded blunt-end or sticky-end ligation. In some aspects, the present disclosure includes ligating a universal nucleic acid sequence to the 3' or 5' end or both ends of the target DNA. In some aspects, the present disclosure includes tailing the 3' end of the target DNA enzymatically with a plurality of a single type of nucleotide. In some aspects, enzymatic tailing is performed with a terminal nucleotidyl transferase. In some aspects, the 3' end of the adapter hybridizes to the 3' end of the target DNA. In some aspects, a modification specific barcode is introduced wherein one or both of the 3' ends are extended by a DNA polymerase. In some aspects, an adapter with 3' degenerate bases primes the target DNA randomly and a modification specific barcode is introduced wherein one or both of the 3' ends are extended by a DNA polymerase.

The goal of adapter/barcode transfer is covalent attachment of the adapter/barcode to a target nucleic acid molecule. For example, in some embodiments, a barcode is transferred to the target nucleic acid by covalently coupling the barcode to the 5' or 3' end of the target nucleic acid. In some embodiments, a barcode is transferred to the target nucleic acid by covalently coupling the barcode or its complement to the 5' or 3' end of the target nucleic acid. The labeled/barcoded nucleic acid molecule may, in some embodiments, be sequenced in downstream steps. In some embodiments, a copy of the labeled target nucleic acid may be sequenced. FIGS. 4, 7A-7B, and 8 provide examples of adapter/barcode transfer reactions.

Adapter/barcode transfer to a target DNA may be performed using one or more DNA ligases, such as T4 DNA ligase, CircLigase, T3 DNA ligase, T7 DNA ligase, 9° N DNA Ligase, Taq DNA Ligase or *E. coli* DNA ligase. A 9° N DNA Ligase is a DNA ligase that catalyzes the formation of a phosphodiester bond between juxtaposed 5' phosphate and 3' hydroxyl termini of two adjacent oligonucleotides which are hybridized to a complementary target DNA.

Splint ligation may also be used to transfer an adapter/barcode to a target nucleic acid. In splint ligation, a bridging DNA is used to bring two nucleic acids together, which may be joined by one or more enzymes. Splinted DNA ligation may be performed using enzymes like T4 DNA ligase, T3 DNA ligase, T7 DNA ligase or *E. coli* DNA ligase.

Additionally, double-stranded ligation may also be used to transfer an adapter/barcode to a target nucleic acid. In some embodiments, the target nucleic acid molecule may be double-stranded DNA, and may have either a blunt or a sticky end. Blunt and sticky end ligation of double-stranded DNA may be catalyzed by T4, T3, T7 or *E. coli* ligase.

In some embodiments, chemical ligation may be used to transfer an adapter/barcode to a target nucleic acid.

Methods for Preventing or Reducing Inter-Complex Adapter/Barcode Transfer by Spatial Separation Intra-complex adapter/barcode transfer may be favored by spatial separation of the molecules involved in the reaction. Specifically, by separating complexes that comprise target nucleic acids, binding domains, and adapters, the transfer of barcodes between complexes, i.e., inter-complex adapter/barcode transfer, becomes unfavorable. This assay configuration increases the fidelity of barcoding.

Barcode Transfer

Each binding domain binds specifically to a target bringing the adapter of the nucleic acid in close proximity to either the 3' or the 5' end of the target nucleic acid. The adapter (e.g., an adapter comprising or consisting of a barcode) may then by transferred to the target nucleic acid. In some embodiments, the transferring occurs in an environment that substantially prevents off-target generation of barcoded nucleic acids. Such an environment may be, for example, an environment wherein the target nucleic acids cannot interact with one another (i.e., only one binding domain may interact with each target nucleic acid). This may be achieved, for example, by performing the barcode transfer reaction in a very dilute solution, or by immobilizing either the target nucleic acid or the binding domain on a substrate to achieve spatial separation thereof. In some embodiments, the transferring is performed by copying the target nucleic acid, to generate a labeled/barcoded copy of the target nucleic acid. For example, if a barcode is transferred to a target nucleic acid, or is brought into close proximity to a target nucleic acid, primer extension may be used to generate a barcoded copy of the target nucleic acid. In some embodiments, barcode transfer may occur in an environment wherein generation of off-target barcoded DNA is less than 20% of the total barcoded target DNA. In some embodiments, generation of off-target barcoded DNA is less than 19%, 18%, 17%, 16%, 15%, 14%, 13%, 12%, 11%, 10%, 9%, 8%, 7%, 6%, 5%, 4%, 3%, 2%, or 1% of the total barcoded target DNA. In some embodiments, an environment wherein generation of off-target barcoded DNA is less than any of the preceding percent ranges, relative to the total barcoded target DNA, is an environment that allows for spatial separation. In some embodiments, as detailed further below, one or more of the target nucleic acids, binding domains, adapters, and the transfer of barcodes are coupled to a substrate to provide an environment wherein generation of off-target barcoded DNA is less than any of the preceding percent ranges, relative to the total barcoded target DNA. In some embodiments, an environment wherein generation of off-target barcoded DNA is less than any of the preceding percent ranges, relative to the total barcoded target DNA, is an environment wherein multiple copies of an adapter are coupled to a substrate at a specific density, or density range, as described further below.

Barcode transfer reactions and spatial separation are described above, and in FIGS. 7A-7B.

Barcode transfer may be performed in several different environments that allow for spatial separation. Spatial separation can be achieved, for example, by high dilution of the complexes comprising binding domains bound to a target in solution. The solution must be dilute enough to allow for spatial separation of any complexes comprising binding domains bound to target nucleic acids present therein. Such spatial separation promotes intra-complex barcode transfer, and substantially prevents barcode transfer between binding domain complexes. In some embodiments, the concentration of the complexes in the dilute solution is less than 1000 nM, less than 500 nM, less than 100 nM, less than 10 nM, less than 1 nM, less than 0.1 nM, less than 0.01 nM, or less than 0.001 nM.

In some embodiments, spatial separation can be achieved by substrate immobilization. For example, the binding domains described herein may be immobilized by being coupled to a substrate. Each substrate may comprise only one type of binding domain, or may comprise at least two, at least three, at least four, at least five, or more types of binding domain. Each "type" of binding domain binds to a different histone modification or DNA binding protein and/or comprises a different barcode. In some embodiments, a first binding domain is spatially separated from a second binding domain on a surface of the substrate. Surface binding capacity and format may be tailored to enable absolute or relative quantification of target molecules and modifications.

Exemplary substrates to which the binding domains, adapters, and intermediate proteins, linkers, and tethers may be coupled include, for example, beads, chips, plates, slides, dishes, or 3-dimensional matrices. In some embodiments, the substrate is a resin, a membrane, a fiber, or a polymer. In some embodiments, the substrate is a bead, such as a bead comprising sepharose, agarose, cellulose, polystyrene, polymethacrylate, and/or polyacrylamide. In some embodiments, the substrate is a magnetic bead. In some embodiments, the support is a polymer, such as a synthetic polymer. A non-limiting list of synthetic polymers includes: polystyrene, poly(ethylene)glycol, polyisocyanopeptide polymers, polylactic-co-glycolic acid, poly($\varepsilon$-caprolactone) (PCL), polylactic acid, poly(3-hydroxybutyrate-co-3-hydroxyvalerate) (PHBV), chitosan and cellulose.

The binding domain may be coupled directly to the surface of substrate. For example, molecules may be coupled directly to the substrate by one or more covalent or non-covalent bonds. In embodiments wherein the substrate is a 3D matrix or other 3D structure, the binding domain may be coupled to multiple surfaces of the substrate.

In some embodiments, the binding domain may be coupled indirectly to the surface of the substrate. For example, the binding domain may be coupled to the surface of the substrate indirectly via a capture molecule, wherein the capture molecule is coupled directly to the substrate. The capture molecule may be any nucleic acid, protein, sugar, chemical linker, etc., that can bind or be linked to both the substrate and the binding domain and/or the target nucleic acid. In some embodiments, a capture molecule binds to a binding domain. In some embodiments, a capture molecule binds to a binding domain or to an adapter (e.g., to the linker of an adapter) of the binding domain. In some embodiments, a capture molecule binds to a target nucleic acid. For example, in some embodiments, a capture molecule may bind to a polyA tail of the target nucleic acid or to a specific nucleic acid sequence.

In some embodiments, the target nucleic acid may be coupled directly to the surface of the substrate via a reactive chemical group. For example, the nucleic acid target may be modified with azido groups that undergo Cu-catalyzed click chemistry with alkyne decorated beads. Other examples: trans-cyclooctene (TCO)/methyl-tetrazine, DBCO/azido.

In some embodiments, a first binding domain is separated from a second binding domain on the surface of a substrate, so as to ensure that each binding domain can only interact with one target nucleic acid. In some embodiments, a first binding domain is separated from a second binding domain by at least 50 nm. For example the first and second binding domain may be separated by about 50 nm to about 500 nm, such as about 50 nm to about 100 nm, about 100 nm to about 150 nm, about 150 nm to about 200 nm, about 200 nm to about 250 nm, about 250 nm to about 300 nm, about 300 nm to about 350 nm, about 350 nm to about 400 nm, about 400 nm to about 450 nm, or about 450 nm to about 500 nm. In some embodiments, the first and second binding domain may be separated by more than about 500 nm.

In some embodiments, multiple copies of an adapter are coupled to a substrate, at a density of approximately 1 adapter/5 nm$^2$ to about 1 adapter/50 nm$^2$, such as 1 adapter/20 nm$^2$. In some embodiments, multiple copies of a binding domain are coupled to a substrate, at a density of approximately 1 binding domain per 1000 nm$^2$ to about 1 binding domain per 15000 nm$^2$, such as 1 binding domain per 8000 nm$^2$.

In general, the goal of coupling a binding domain (or the target nucleic acid) to a substrate is to ensure intra-complex transfer of an adapter and/or a barcode. Substrates comprising two or more spatially-separated binding domains may be produced using methods known to those of skill in the art. The disclosures of the following publications are incorporated herein by reference in their entireties for all purposes: US20210237022A1, US20220010367A1, US20220364163A1, US20220298560, U.S. Pat. No. 11,519,033, US20210010070.

Coupling of a Binding Domain to a Substrate

In some embodiments, a binding domain is coupled directly or indirectly to a substrate. In some embodiments, a plurality of binding domains are immobilized on a substrate using site-specific chemistry. For example, in some embodiments, the binding domain comprises a site that allows it to be immobilized on a substrate. Coupling of a binding domain to the surface of a substrate may be facilitated by fusing self-catalyzing protein tags to the terminus of the binding domain (e.g., SpyCatcher, sortase A, SNAP-tag®, HaloTag® and CLIP-tag™). These protein tags on the binding domain may then be covalently reacted with their cognate reactive moieties on the surface of the substrate. For example, the SpyCatcher protein may be engineered into a binding domain. SpyTag forms a covalent linkage with a SpyTag protein (a 13aa peptide). If SpyTag is coupled to the surface of a substrate, a reaction between a SpyCatcher-linked binding domain and SpyTag will serve to covalently link the binding domain to the substrate. Similarly, a binding domain may be fused with a Sortase A tag, which could be used to react with pentaglycine coupled to a substrate surface. As another example, a binding domain may be fused with a SNAP-tag®, which could be used to react with O$^6$-benzylguanine that is coupled to a substrate surface. In some embodiments, a binding domain may be fused with a CLIP-tag™, which could be used to react with 02-benzyl-cytosine that is coupled to a substrate surface. In some embodiments, a binding domain may be fused with a HaloTag® (a modified haloalkane dehalogenase enzyme), which could be used to react with an alkyl halide present on a substrate surface.

In some embodiments, the binding domain may comprise a biotin moiety. Such binding molecules may be immobilized on a substrate surface by a capture molecule that binds biotin (e.g., avidin, streptavidin, or neutravidin).

Figure 5A:
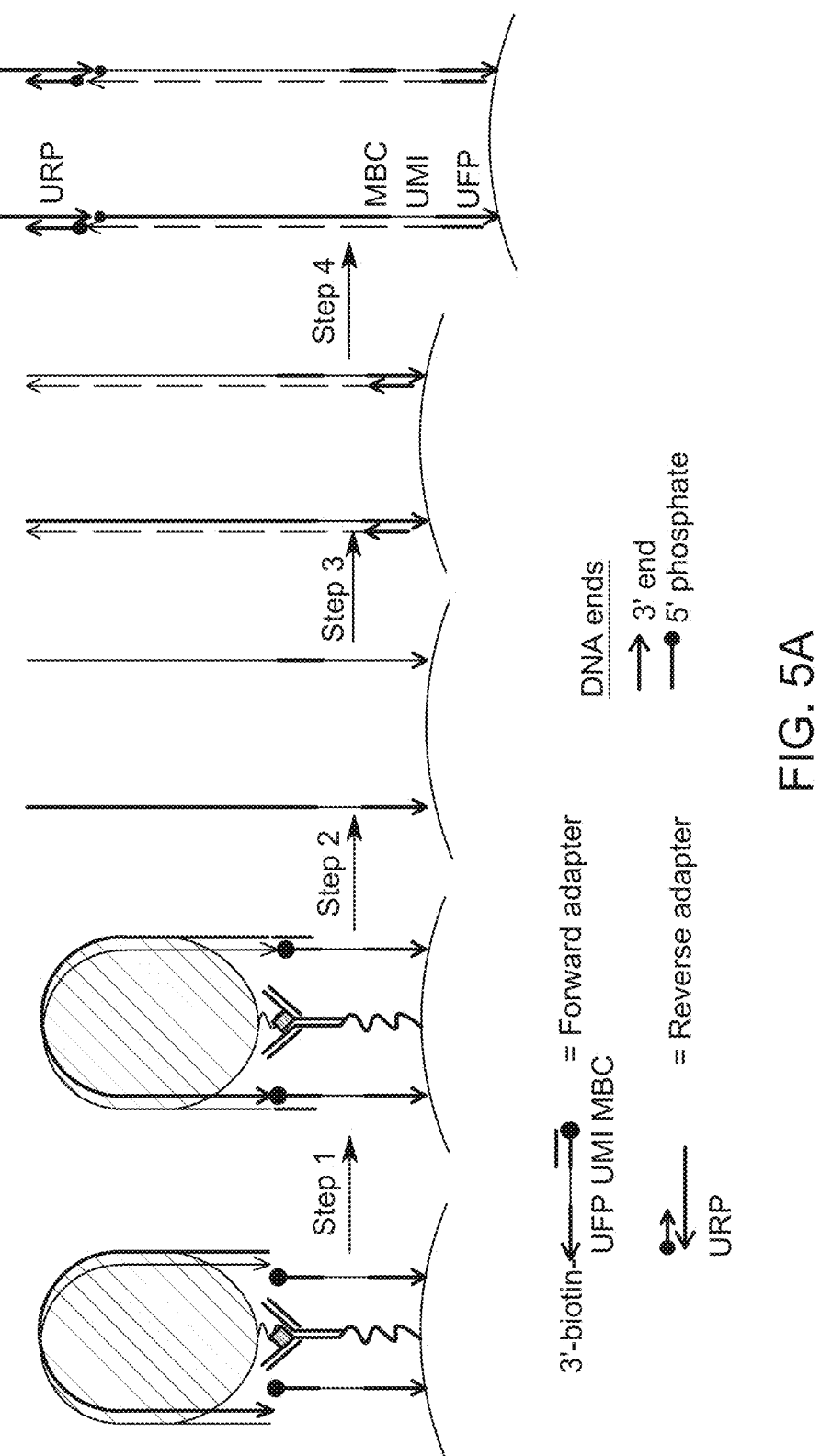
FIGS. 5A-5B show detection of a single histone (FIG. 5A) or multiple histone modifications (FIG. 5B) using immobilized adapters. To detect a single histone modification per nucleosome (FIG. 5A), the nucleosomes are first immunoprecipitated with a pool of bead substrates. Next, the forward adapter is ligated (step1) and the histone core removed by denaturation (step 2). The complementary DNA strand is initiated by priming the UFP region and extending the primer with a DNA polymerase (step 3). Last, the double-stranded DNA is ligated to the reverse adapter (step 4) resulting in a DNA library ready for sequencing. To detect multiple histone modifications per nucleosome (FIG. 5B), the workflow employs beads with cleavable adapters. After the first barcoding step by ligation (step 1), the adapters are released from the surface by cleavage at the uracil base (U) (step 2). The barcoded nucleosomes are collected, recombined with the supernatant and exposed to a bead pool with different binding domains.

FIG. 5A shows a binding domain coupled to a substrate or surface via a tether. In some embodiments, a plurality of binding domains may be directly or indirectly immobilized on a substrate using site-specific chemistry. For example, in some embodiments, the binding domain of a binding domain may comprise a site that allows it to be immobilized on a substrate, and a site for tethering the DNA adapter. Conjugation of a binding domain to the surface of a substrate may be facilitated by fusing self-catalyzing protein tags to the terminus of the binding domain (e.g., SpyCatcher, sortase A, SNAP-tag®, HaloTag® and CLIP-tag™). SNAP-tag® is a self-labeling protein derived from human O$^6$-alkylguanine-DNA-alkyltransferase. SNAP-tag® reacts with covalently with O$^6$-benzylguanine derivatives, for example fluorescent dyes conjugated to guanine or chloropyrimidine. CLIP-tag™ is a modified version of SNAP-tag®. It is also a self-labeling protein derived from human O$^6$-alkylguanine-DNA-alkyltransferase. Instead of benzylguanine derivatives, CLIP-tag™ is engineered to react with benzylcytosine derivatives. These protein tags on the binding domain may then be covalently reacted with their cognate reactive moieties on the surface of the substrate. For example, the SpyCatcher protein may be engineered into a binding domain. SpyTag forms a covalent linkage with a SpyTag protein (a 13aa peptide). If SpyTag is coupled to the surface of a substrate, a reaction between a SpyCatcher-linked binding domain and SpyTag will serve to covalently link the binding domain to the substrate. Similarly, a binding domain may be fused with a Sortase A tag, which could be used to react with pentaglycine coupled to a substrate surface. As another example, a binding domain may be fused with a SNAP-tag®, which could be used to react with O$^6$-benzylguanine that is coupled to a substrate surface. In some embodiments, a binding domain may be fused with a CLIP-tag™, which could be used to react with 02-benzylcytosine that is coupled to a substrate surface. In some embodiments, a binding domain may be fused with a HaloTag®, which could be used to react with an alkyl halide present on a substrate surface.

In some embodiments, the binding molecule may comprise a biotin moiety. Such binding molecules may be immobilized on a substrate surface by a capture molecule that binds biotin (e.g., avidin, streptavidin, or neutravidin).

Coupling a Target Nucleic Acid or an Adapter to a Substrate

In some embodiments, the compositions herein comprise one substrate. In some embodiments, the compositions herein comprise two or more substrates. In some embodiments, a composition comprises a plurality of substrates wherein each substrate is formed from the same material. In some embodiments, a composition comprises a plurality of substrates wherein each substrate is formed from a different material. In some embodiments, the substrate is a bead, chip, plate, tube, slide, dish, gel, or 3-dimensional polymer matrix. Substrates may be formed from a variety of materials. In some embodiments, the substrate is a resin, a membrane, a fiber, or a polymer. In some embodiments, the substrate comprises sepharose, agarose, cellulose, polystyrene, polymethacrylate, and/or polyacrylamide. In some embodiments, the substrate comprises a polymer, such as a synthetic polymer. A non-limiting list of synthetic polymers includes: poly(ethylene)glycol, polyisocyanopeptide polymers, polylactic-co-glycolic acid, poly(ε-caprolactone) (PCL), polylactic acid, poly(3-hydroxybutyrate-co-3-hydroxyvalerate) (PHBV), chitosan and cellulose.

In some embodiments a substrate may be decorated with oligonucleotide capture molecules that hybridize to a feature of a target nucleic acid. For example, a poly-dA tail added to the DNA of a nucleosome using a terminal nucleotidyl transferase may be captured by hybridization to a capture molecule that comprises poly-dT oligonucleotides or gene-specific sequences. In some embodiments, the capture molecules are present at a low substrate density to physically isolate the binding domains. Barcode transfer from the nucleosome or protein-binding-conjugate to the target nucleic acid may, in some embodiments, occur in the substrate-bound state (i.e., when the target nucleic acid is coupled to the substrate).

Beads for target nucleic acid capture by hybridization can be prepared by direct conjugation of 5'-amino-modified oligonucleotides to substrate-activated beads. The substrate-activated beads may exhibit epoxy, tosyl, carboxylic acid or amine groups for covalent linkage. Carboxy beads typically need to be allowed or induced to react with carbodiimide to facilitate peptide bond formation, and amine beads typically require a bifunctional NHS-linker. In some embodiments, the surface of the bead is passivated to prevent non-specific binding. Passivation can be achieved, in some embodiments, by co-grafting poly-ethylene glycol (PEG) molecules with the same linkage chemistry. For example, 5'-amino-modified oligonucleotides and amino-terminated polyethylene glycol (PEG) is used such that, on average, most substrate sites will be occupied by PEG molecules that will serve to spatially distribute the oligonucleotides. If an excess of PEG is used, the oligonucleotides will be, on average, spatially separated from one another. The surface density of capture molecules can be adjusted by altering the ratio of oligonucleotide to PEG molecules.

In some embodiments, the beads are Sepharose beads made with mTet (tetrazine) and carboxy-PEG. A reduced ratio of mTet to carboxy-PEG reduces crosstalk between target nucleic acids. In some embodiments, the mTet:carboxy-PEG ratio is 1:500, 1:600, 1:700, 1:800, 1:900, 1:1000, 1:1100, 1:1200, 1:1300, 1:1400, 1:500, 1:1000, 1:2000, 1:3000, 1:4000, 1:5000, 1:6000, 1:7000, 1:8000, 1:9000, or 1:10000. In some embodiments, the mTet:carboxy-PEG ratio is 1:1000.

In some embodiments, a substrate comprises a plurality of the same or different binding domains. In some embodiments, a substrate comprises a plurality of the same or different adapters.

Nucleosome-Binding Conjugates

Also provided herein are nucleosome-binding conjugates comprising a binding domain coupled to an adapter. In some embodiments, 1, 2, 3, 4, 5, 6, 7, 8, 9, 10, 11, 12, 13, 14, or 15 adapters are conjugated to the binding domain. In some embodiments, the binding domain and the adapter comprises any of the binding domains or adapters described in any of the preceding paragraphs.

Nucleic Acid Analysis Methods

The nucleosome-binding conjugates described herein, which are capable of intra-complex barcode transfer as described above, may be used in various methods of analyzing nucleic acids, specifically for recognizing histone modifications or a DNA binding protein. This disclosure thus provides methods for analyzing histone modifications, including methods for profiling of multiple modifications of histones and nucleosomes, and DNA binding proteins. In these methods, histone modifications or DNA binding proteins may be recognized by a binding domain. The adapter or part thereof (e.g., a barcode) is then transferred from the binding domain to the target nucleic acid (i.e., to generate a labeled/barcoded target nucleic acid). Because the barcode is unique to the particular histone modification(s), this step serves to write the information from the recognition event into the nucleic acid sequence of the target nucleic acid. The resultant barcoded target nucleic acid is then converted into a sequencing library, and read by nucleic acid sequencing methods. This step reveals the sequence of the barcode, which is correlated with the histone modification or DNA binding proteins. Sequencing may also allow for localization of the histone modifications or binding sites of the DNA binding proteins. The high throughput profiling methods described herein allow for identification of the nature and location of several or all nucleosome modifications and DNA binding proteins in parallel.

The methods described herein and depicted in the figures comprise a series of steps, as described below. As will be understood by those skilled in the art, in some embodiments, various steps may be omitted and/or performed in a different order.

Contacting the Binding Domains and the Target Nucleic Acids

In some embodiments, the methods described herein comprise a step of contacting one or more binding domains with a target, e.g., one or more target nucleic acids or one or more histone modifications and DNA binding proteins. The target nucleic acids may be, for example, chromatin or nucleosome nucleic acids isolated from a cell or tissue of an organism. In some embodiments, the binding domain contacts a DNA binding protein as described herein.

Contacting the binding domain(s) with the target may occur in solution. For example, a composition comprising one or more target nucleic acids or DNA binding proteins may be contacted with a composition comprising one or more binding domains. In some embodiments, the contacting may occur in a dilute solution, so that only one binding domain may interact with each target.

In some embodiments, the contacting occurs on a substrate/surface. For example, one or more targets may be coupled to a substrate/surface, and one or more binding domains may be contacted with the target nucleic acids coupled to the substrate/surface. In some embodiments, one or more binding domains may be coupled to a substrate/surface, and one or more targets may be contacted with the binding domains coupled to the substrate/surface.

The target nucleic acids or DNA binding proteins may be contacted with only one type of binding domain protein (i.e., to detect only one type of histone modification or one DNA binding protein), or in some embodiments, the target nucleic acids may be contacted with more than one type of binding domain, to detect multiple histone modifications. For example, the target nucleic acids may be contacted with at least one, at least two, at least three, at least four, at least five, at least six, at least seven, at least eight, at least nine, at least ten, or more different types of binding domains.

In some embodiments, the targets are contacted with a first pool of binding domains, and then later contacted with a second pool of binding domains. In some embodiments, the pools may comprise different types of binding domains (i.e., recognizing different types of modifications or proteins). In some embodiments, the pools may each comprise 1-5, 5-10, 10-25, 25-50, 50-100, 100-150, 150-175, 175-200, 250, 300, 350, 400, or more different types of binding domains.

Barcode Transfer

Each binding domain binds specifically to a target bringing the adapter in close proximity to either the 3' or the 5' end of the target nucleic acid. The adapter (e.g., an adapter comprising or consisting of a barcode) may then be transferred to the target nucleic acid. In some embodiments, the transferring occurs in an environment that substantially prevents off-target generation of barcoded nucleic acids. Such an environment may be, for example, an environment wherein the target nucleic acids cannot interact with one another (i.e., only one binding domain may interact with each target nucleic acid). This may be achieved, for example, by performing the barcode transfer reaction in a very dilute solution, or by immobilizing either the target nucleic acid or the binding domain on a substrate to achieve spatial separation thereof. In some embodiments, the transferring is performed by copying the target nucleic acid, to generate a labeled/barcoded copy of the target nucleic acid. For example, if a barcode is transferred to a target nucleic acid, polymerase chain reaction (PCR) may be used to generate a barcoded copy of the target nucleic acid.

Barcode transfer reactions and spatial separation are described above, and in FIGS. 7A-7B.

Amplification and Sequencing

After a target nucleic acid has been barcoded, it may be amplified and then sequenced. This step reveals the sequence of the barcode, which is correlated with the histone modifications originally bound by the binding domain in the target nucleic acid(s). Sequencing reveals the sequence and the length of the DNA fragment, which allows for localization of the histone modifications. Sequencing may also reveal a mutation near the histone modification, from which the location of the histone modifications can be derived informatically.

Thus, in some embodiments, the method described herein may comprise a step of sequencing the barcoded target nucleic acids, or copies thereof. The sequencing step may be performed using any suitable method known in the art. For example, the sequencing may be performed using a next-generation sequencing (NGS) method, a massively parallel sequencing method, or a deep sequencing method. There are a number of NGS platforms that may be used with the methods of the instant disclosure. For example, Illumina® (Solexa©) sequencing works by sequencing by synthesis where blocked fluorescent nucleotides are incorporated, imaged and deblocked before the next fluorescent nucleotide insertion. Roche® 454 sequencing is based on pyrosequencing, a technique which detects pyrophosphate release using fluorescence, after nucleotides are incorporated by a polymerase to a new strand of DNA. Ion Torrent® (Proton/PGM sequencing) measures the direct release of protons (H+) from the incorporation of individual nucleotides by DNA polymerase. Oxford® Nanopore sequencing measures the change in current as a nucleic acid thread through a pore base by base. Pacific Biosciences® Single Molecule Real Time (SMRT) sequencing measures the residence time of a fluorescently labeled nucleotide while it is incorporated into DNA by a DNA polymerase molecule that is immobilized at the bottom of a zero-mode waveguide.

In some embodiments, sequencing is not required to detect a target nucleic acid. For, example, the target nucleic acid may be detected using PCR. For example, PCR may be used to detect whether a target nucleic acid (e.g., a barcode) is present. In some embodiments, a target nucleic acid is detected using a fluorescent probe (e.g., a fluorescently-labeled hybridization probe). In some embodiments a target nucleic acid is detected using a microarray or other nucleic acid array. Methods for analyzing sequencing results or data from any of the methods for detecting target nucleic acids described herein are known to those of skill in the art. For example, standard bioinformatics methods are used to analyze sequencing results.

In some embodiments, sequencing is not required to detect the addition of a barcode by a reaction mediated by the binding domain. For example, the presence of a histone modification may be confirmed by detecting the associated barcode using nucleic acid electrophoresis, a fluorescent hybridization probe, PCR or any other nucleic acid amplification method that can be triggered by the barcode.

Illustrative Methods for Identification, and or Localization of Histone Modifications In some embodiments, assay beads display a modification-specific antibody and forward adapters comprising 3' end, blocked 3' end, and 5' phosphate (FIG. 5A). In some embodiments, the target DNA of the nucleosome may be end-repaired prior to immunoprecipitation. In some embodiments, the histone modification is identified by ligating the forward adapter to the target DNA during or after immuno-precipitation. In an exemplary embodiment, in FIG. 5A, only the immobilized strand of the adapter is ligated due to the presence of a 3' blocking group on the other forward adapter strand, or the lack of a 5'-phosphorylation on the target DNA. Next, the barcoded DNA is primed and copied by a DNA polymerase. The last step illustrated in FIG. 5A is the ligation of a reverse adapter. In some embodiments, multiple histone targets may be detected in the same reaction using multiple bead types that are combined, each exhibiting uniquely barcoded adapters and a modification-specific anti-body (see, for example, FIGS. 3A-3B). Also shown in FIG. 5A, two forward adapters may be attached to the substrate. The forward adapters may comprises a UFP, UMI, and MBC and are then ligated to the target DNA of the nucleosome comprising the histone modification. After ligation, a dena-turing step is performed to remove the chromatin core, followed by reverse strand synthesis of the ligated target DNA to form forward and reverse strands. A reverse adapter is then ligated to the forward and reverse strands of target DNA. The barcoded target DNA is amplified and analyzed by sequences.

Figure 5B:
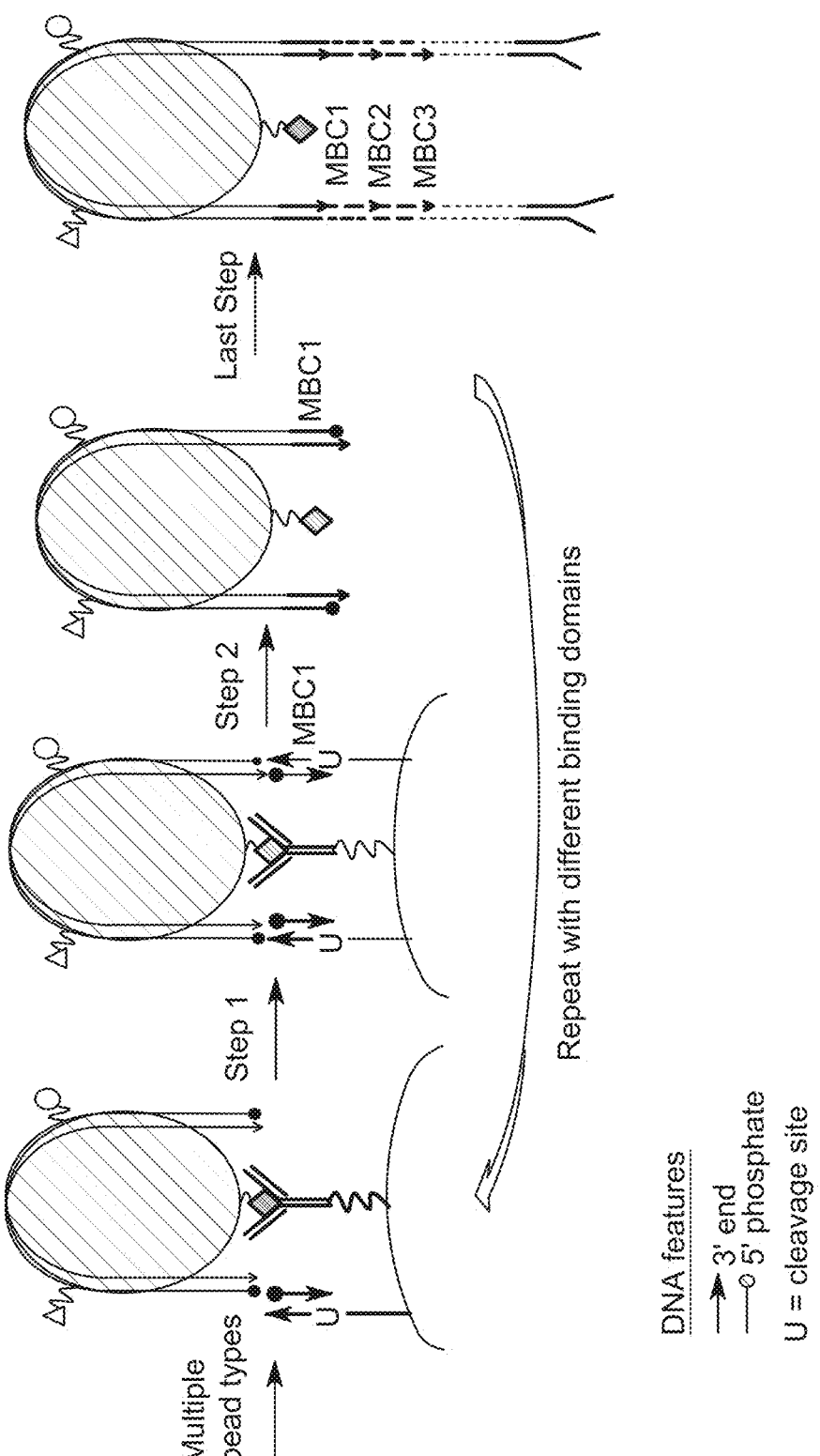

In some embodiments, assay beads display a modifica-tion-specific antibody and surface adapters comprising an MBC along and uracil recognizable by UdG/endonuclease. As illustrated in FIG. 5B, the target DNA of the nucleosome has been end-repaired and 5'-phosphorylated prior to immu-noprecipitation. The first histone modification is identified by ligating the forward adapter to the target DNA during or after immunoprecipitation, thereby appending a first MBC. Afterwards, the barcoded nucleosome is released by cleav-ing the adapter at the position of the uracil with an enzyme mix comprising UdG and an endonuclease, for example, but not limited to endonuclease VIII. The second histone modi-fication is detected by repeating the steps above, this time using a different set of binding domains and introducing a second MBC. The last step is the ligation of Y-shaped sequencing adapters. The reaction scheme illustrated in FIG. 5B allows for using multiple bead types with their associated barcodes in each cycle of encoding. In some embodiments, the releasing step comprises adding a buffer selected from an antigen elution buffer, a histone or antibody replacement mixture, an acidic buffer with a pH of 6.5 or below, or an alkaline buffer with a pH of 8.5 or above. An elution buffer may comprise a high-salt solution for effectively dissociat-ing affinity interactions while preserving both antibody and antigen activities. A histone replacement mixture may com-prise histone or peptide bearing specific modifications in excess amount. An antibody replacement mixture may also comprise excess amount of synthetic modified histone pep-tide as a competitor to dissociate the binding domain from nucleosome. A buffer may comprise a reducing agent (DTT and/or TCEP) to cleave disulfide bonds of an antibody, an enzyme that specifically digests antibodies (papain and/or pepsin), a surfactant (SDS, Sodium Deoxycholate), an acidic buffer with a pH of 6.5 (typically glycine•HCl, pH 2.5-3.0) or below, or an alkaline buffer with a pH of 8.5 or above.

Figure 6:
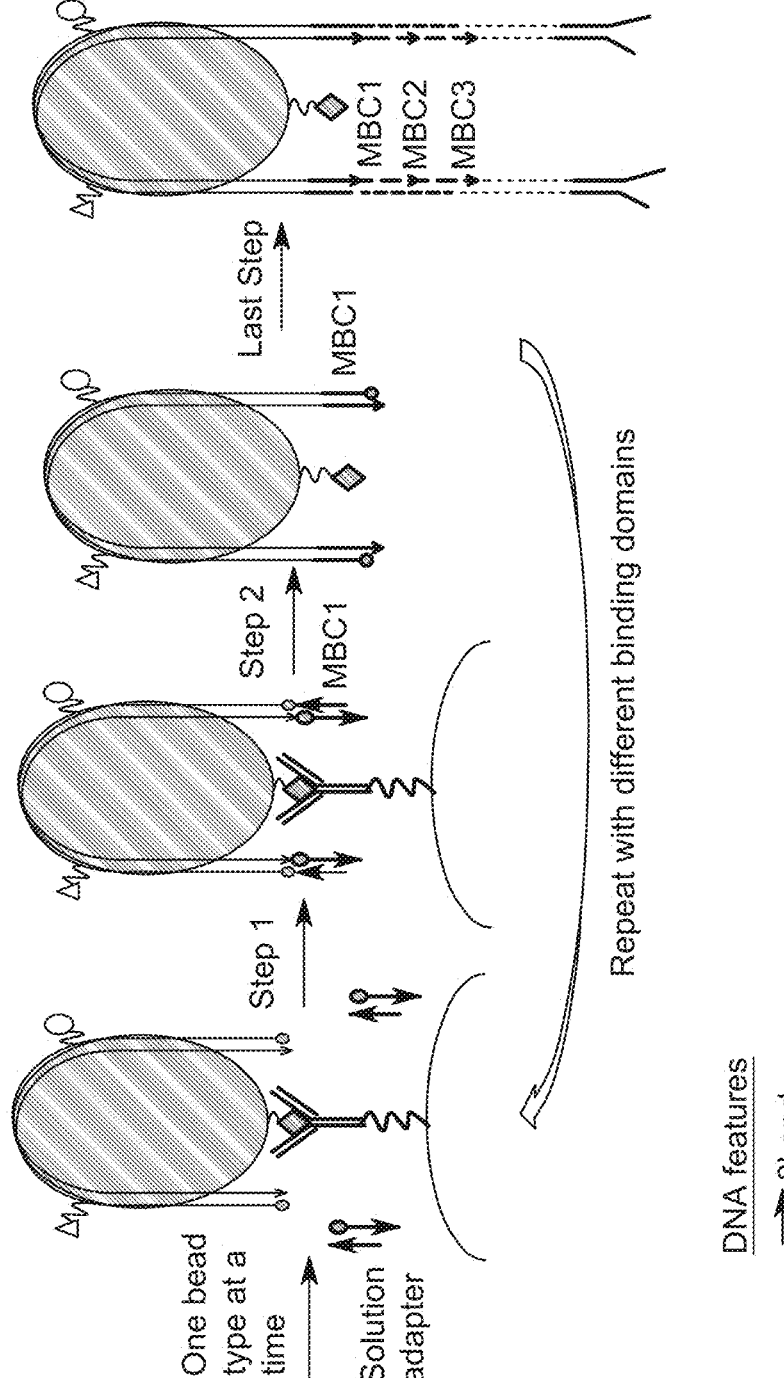
FIG. 6 shows co-localization of histone modifications by serial encoding with adapters in solution. Because the adapters are not localized to the binding domains, each barcoding cycle is performed with a single bead type.
Figure 9:
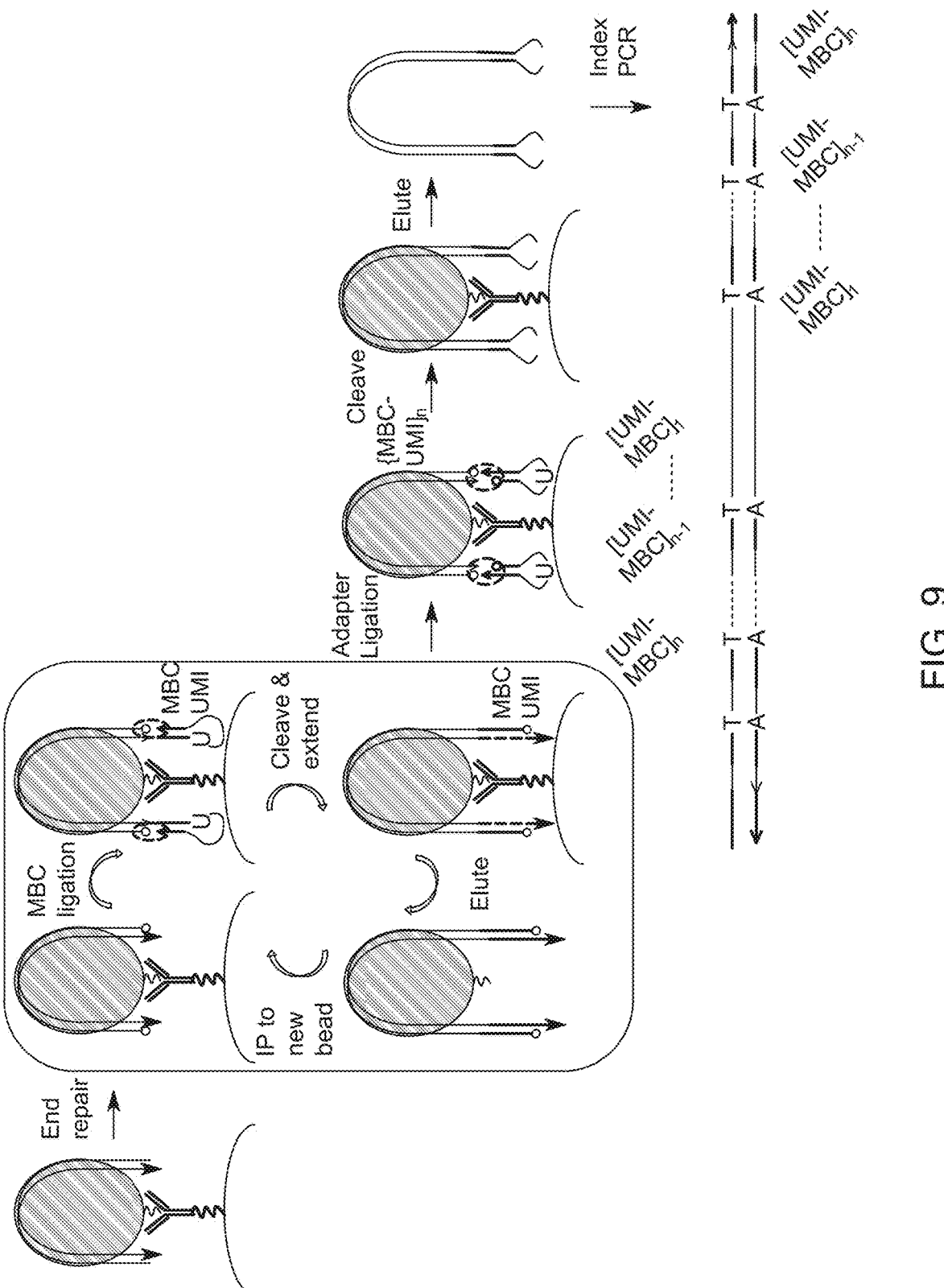
FIG. 9 shows co-localization of histone modifications by serial encoding with adapters in solution similar to FIG. 6, with the difference that the adapter architecture allows for the addition of a UMI adjacent to the MBC in each barcoding cycle.

FIG. 6 and FIG. 9 illustrate co-localization of histone modifications by serial encoding with solution barcodes. In some embodiments, repeated cycles of IP and barcoding may be used to identify several histone modifications on the same nucleosome. In some embodiments, MBCs are unteth-ered from a surface or substrate. In some examples, the MBC is connected to a cleavable loop region comprising a unique molecular identifier (UMI), as depicted in FIG. 9. This configuration allows for the attachment of an MBC adjacent to a UMI with each cycle of barcoding. Because a single bead species is present in each IP cycle, the MBCs do not need to be tethered to a substrate. In some embodiments, UMIs are attached to MBCs. In each cycle, nucleosomes are immunoprecipitated, washed and barcoded by ligating MBCs in solution. For the next cycle of encoding, the nucleosomes are detached from the substrate, combined with the supernatant of previous IP cycles and subjected to the next cycle of encoding. Sequencing adapters are ligated to both ends of the nucleosome in the concluding steps to generate a sequencing library. In some embodiments, the sequencing adapters are Y-shaped, or bell-shaped. In some embodiments, the sequencing adapters include UMIs. This method generates a tail of MBCs at the nucleosome's ends, which are indicative of the histone modifications.

Figure 7A:
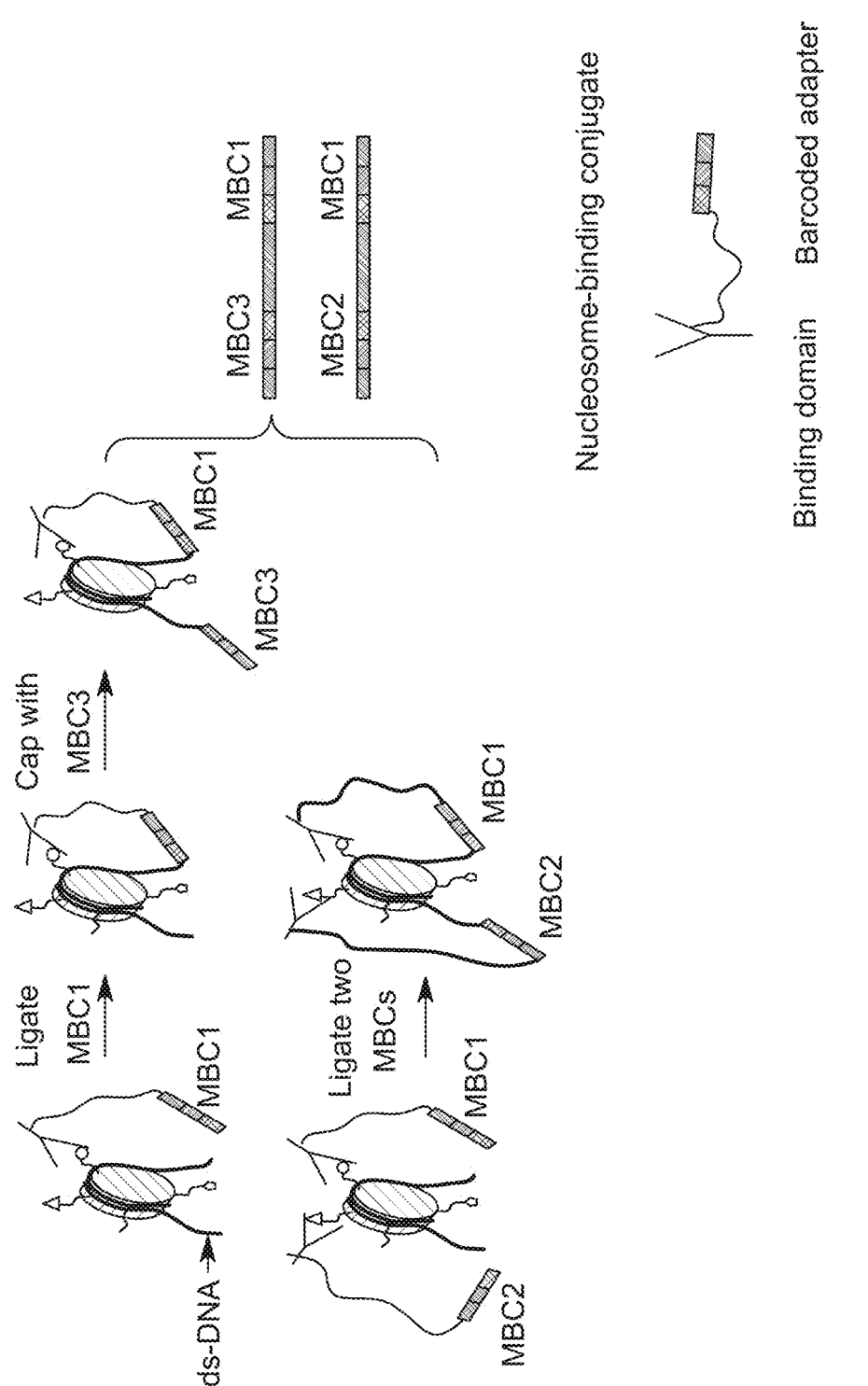
FIGS. 7A-7B show detection of one or two histone modifications by barcoding of both nucleosome ends by nucleosome-binding conjugates comprising a binding domain and a tethered adapter (FIG. 7A) and co-localization of histone modifications by serial barcoding of a nucleosome that is attached to a substrate (FIG. 7B).

In some embodiments, detection of multiple histone modifications may comprise barcoding both nucleic acid ends of a nucleosome. As illustrated in FIG. 7A, after end-repairing and adenylating the nucleosomes, they are incubated with a plurality of nucleosome binding conju-gates, each comprising a binding domain and a modification barcode (MBC). The presence of ligase enzyme initiates an encoding reaction, transferring either one or two MBCs to the target DNA. If only one adapter has been transferred during the encoding step, an additional capping step with free adapter is used to obtain an amplifiable library.

Figure 7B:
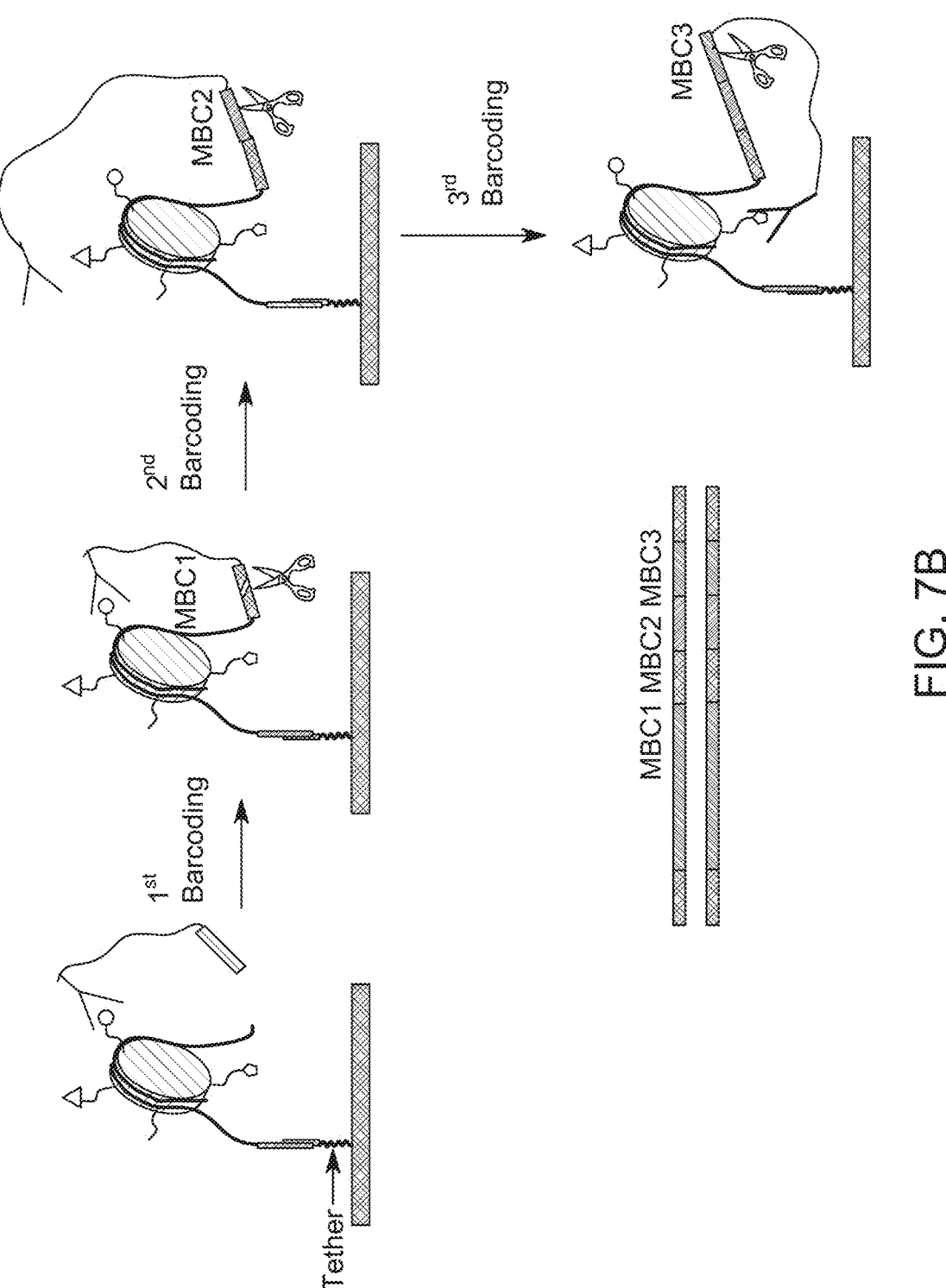
Figure 7B:
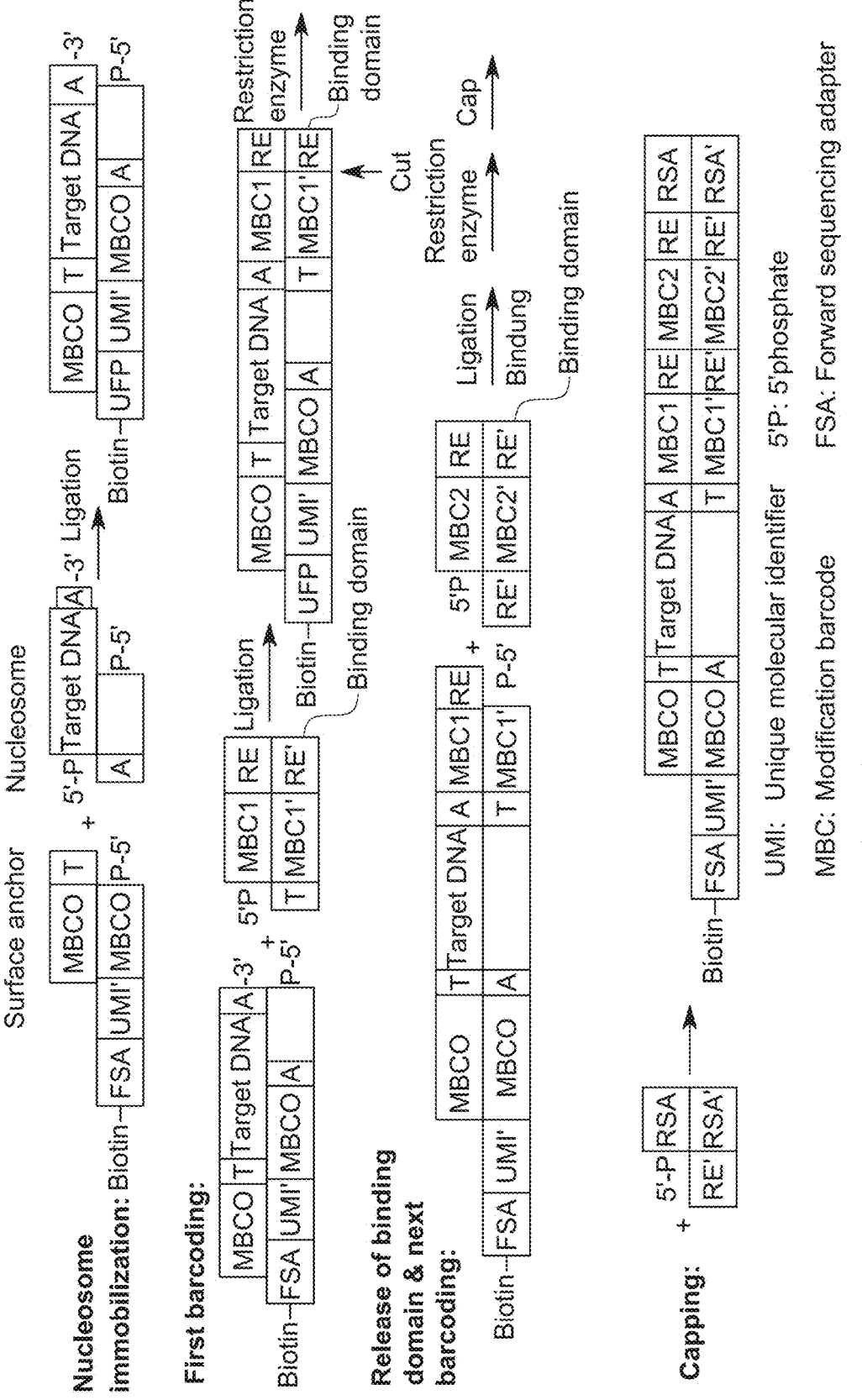

In some embodiments, multiple histone modifications are detected by a serial barcoding reaction of a nucleosome attached to a substrate. As illustrated in FIG. 7B, in the first step, nucleosomes are anchored on a substrate at single molecule spacing to prevent neighboring nucleosomes from interacting. To identify the first histone modification a barcode-labeled antibody is introduced. After washing, liga-tion reagents are added, and the antibody barcode is attached to the free end of the nucleosome. Cleavage of the barcode with a restriction enzyme releases the antibody and gener-ates a cohesive barcode end for the next round of encoding. The steps can be repeated any number of times, always adding a single barcode-antibody conjugate. The capping step in the end introduces the reverse sequencing adapter and is antibody independent. The result is a nucleosome comprising a string of barcodes, each indicating one of the modifications.

In some embodiments, co-localization of histone modifi-cations may be determined by proximity ligation. In some embodiments, proximally localized barcodes are annealed to bridge splint oligos followed by ligation of the proximally localized barcodes. In some embodiments, a nucleosome may be A-tailed to hybridize with poly-T end of a barcode. As shown in FIG. 8, A-tailed nucleosomes are incubated with a mixture of barcode-antibody conjugates. As the antibodies bind to their targets, neighboring barcodes are bridged by splint oligos and ligated. The A-tail of the nucleosome primes the concatenated barcodes and adding a DNA polymerase produces a copy. This process results in a nucleosome attached to a string of barcodes, each identify-ing a modification.

In some embodiments, histone modifications in a tissue may be analyzed by immobilizing nucleosome-binding con-jugates comprising a spatial identifier on a microarray slide and layering the microarray with a tissue. The tissue may be a fresh frozen tissue section or formalin-fixed paraffin embedded (FFPE) tissue. The cells are permeabilized with surfactants (e.g. digitonin, TritonX or NP40), followed by enzymatic shearing of the chromatin and releasing the nucleosomes (e.g. with micrococcal nuclease (MNase) or DNAse). The nucleosomes are allowed to diffuse out of the cells and captured by the immobilized binding domains. The last step is transferring the spatial identifiers to the nucleosomes by ligation (FIGS. 15A-15B) resulting in nucleosomes that are labeled with a modification barcodes and spatial identifiers.

The methods described herein may be used to diagnose a disease, disorder, or condition. For example, in some embodiments, the methods may be used to diagnose cancer in a subject in need thereof. In some embodiments, the kits may be used to monitor a disease, disorder, or condition over time, such as in response to one or more treatments. For example, the kits may be used to monitor epigenetic changes over time in a subject undergoing treatment for cancer (i.e., chemotherapy, radiation, etc.) In some embodiments, the methods may be used to analyze a cell or tissue from a subject in need thereof. For example, the methods may be used to detect histone modifications in a cell or tissue isolated from a blood sample, a biopsy sample, an autopsy sample, etc.

In some embodiments, nucleosomes may be obtained as cell free circulating nucleosomes. For example, cell free circulating nucleosomes may be obtained from the blood of a patient or from an extracellular tumor environment or microenvironment.

In some embodiments, nucleosomes may be obtained from single cells. In some embodiments, nucleosomes may be obtained from a single isolated cell. In some embodiments, nucleosomes may be obtained from a plurality of clonal cells derived from a single cell.

In some embodiments, the disclosure provides a method for diagnosing a cancer or cancer sub-type associated with one or more types of histone modifications, comprising analyzing a plurality of nucleosomes according to any of the numbered aspects. In some embodiments, the disclosure provides a method of monitoring the progression or treatment response of a cancer, comprising analyzing a plurality of nucleosomes according to any of the numbered aspects. In some embodiments, the plurality of nucleosomes are analyzed from a patient blood sample. In some embodiments, the plurality of nucleosomes are analyzed from a patient tissue biopsy sample. In some embodiments, the disclosure provides a kit for monitoring epigenetic changes over time in a subject undergoing treatment for cancer, comprising any composition or nucleosome binding conjugate disclosed herein.

Because histone modifications of cell-free nucleosomes inform on DNA-related activities within the cells of origin, the present disclosure includes methods of using histone modifications of cell-free nucleosomes as biomarkers in liquid biopsy of blood plasma. The present disclosure includes use of multiplexed detection of histone modifications in low sample input scenarios, such as the analysis of cell-free nucleosomes in blood plasma, which contains only 20 to 60 ng of nucleosomes per mL.

In some embodiments, the methods may be used to detect and/or monitor epigenetic changes in cells used commercially for production of one or more products, such as cells used for industrial fermentation. In some embodiments, the methods may be used to detect and/or monitor epigenetic changes in a plant cell or tissue.

Compositions Comprising Binding Domains

Also provided herein are compositions comprising one or more binding domains of the disclosure. In some embodiments, a composition comprises one or more types of binding domains. For example, the composition may comprise a first binding domain that binds to a first histone modification or first DNA binding protein, and a second binding domain that binds to a second histone modification or second DNA binding protein. In some embodiments, the composition may comprise 1, 2, 3, 4, 5, 6, 7, 8, 9, 10, 11, 12, 13, 14, 15, 16, 17, 18, 19, 20, 21, 22, 23, 24, or 25, or more different types of binding domains.

Also provided herein are compositions comprising one or more complexes, wherein each complex comprises a binding domain bound to a target nucleic acid.

In some embodiments, the compositions described herein comprise one or more carriers, excipients, buffers, etc. The compositions may have a pH of about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, or about 14.0. In some aspects, the compositions may have a pH of 2-12, 3-11, 4-10, 5-9, 6-8, or 6.5 to 7.5, or any range within these ranges. In some embodiments, the compositions are pharmaceutical compositions. In some embodiments, the compositions are diagnostic compositions.

Kits for Analyzing Histone Modifications

The binding domains described herein can be provided in a kit (e.g., as a component of a kit). For example, the kit may comprise a binding domain, or one or more components thereof, and informational material. The kit may also include any of the reagents and materials needed to perform the assay as described in this disclosure including the examples. These reagents and materials can include adapters, substrates (beads), and enzymes (ligases, polymerases). The informational material can be, for example, explanatory material, instructional material, sales material, or other material regarding the methods described herein and/or the use of the binding domain. The informational material of the kit is not limited in form. In some embodiments, the informational material may include information regarding the production of the binding domain, molecular weight, concentration, expiration date, batch or production site information, and the like. In some embodiments, the information material may comprise a list of disorders and/or conditions that may be diagnosed or evaluated using the kit.

In some embodiments, the binding domain may be provided in a suitable manner (e.g., in an easy-to-use tube, at a suitable concentration, etc.) for use in the methods described herein. In some embodiments, the kit may require some preparation or manipulation of the binding domain before use. In some embodiments, the binding domain is provided in a liquid, dried, or lyophilized form. In some embodiments, the binding domain is provided in an aqueous solution. In some embodiments, the binding domain is provided in a sterile, nuclease-free solution. In some embodiments, the binding domain is provided in a composition that is substantially free from any nucleic acids besides those that may comprise the molecule itself.

In some embodiments, the kit may comprise one or more syringes, tubes, ampoules, foil packages, or blister packs. The container of the kit can be airtight, waterproof (i.e., to prevent changes in moisture or evaporation), and/or comprise light shielding.

In some embodiments, the kit may be used to perform one or more of the methods described herein, such a method for analyzing a population of target nucleic acids. In some embodiments, the kit may be used to diagnose a disease, disorder, or condition. For example, in some embodiments, the kit may be used to diagnose cancer. In some embodiments, the kit may be used to monitor a disease, disorder, or condition over time, such as in response to one or more treatments. For example, the kit may be used to monitor epigenetic changes over time in a subject undergoing treatment for cancer.

Examples

The following non-limiting examples further illustrate embodiments of the compositions and methods of the instant disclosure.

Example 1: Preparation of Bead Substrates for Modification-Specific Barcoding of Nucleosomes Magnetic beads are convenient substrates for library preparation workflows as they facilitate buffer exchanges and purification steps. This example describes co-loading of magnetic beads with antibodies (Abs) and adapters comprising a modification barcode (MBC). Each bead type was loaded with one type of antibody and one type of adapter at an optimized ratio. Multiple bead types may be combined into a bead pool to detect any number of histone modifications (FIG. 3A). The described beads are intended for the analysis of the histone modifications in a plurality of nucleosomes using the workflow depicted in FIG. 5A. The bead loading protocol can be easily adopted for the workflows shown in FIG. 4 and FIG. 5B by using different adapter sequences. A total of two bead types were prepared, one targeting the H3K4me3 modification, the other targeting the H3K4me2 modification. Two bead loading mixes were prepared, each containing 3'biotinylated adapters, biotinylated protein G and the antibody for the target histone modification at a molar ratio of 3:6:4, in HBST300 buffer (10 mM HEPES pH 7.6, 300 mM NaCl, 0.1 mM EDTA, 0.05% Tween 20) mixed with biotinylated of small molecule PEG. The loading mix for the first bead type comprised protein G, Ab42 (histone H3K4me3 antibody, EpiCypher, cat #13-0041) and rcMBC101 /5Phos/GT-GATCGNNNNNCTGTCTCTTATACACATCTGACUT-TTTT(SEQ ID NO: 1)/3BioTEG/. The loading mix for the second bead type comprised protein G, Ab70 (histone H3K4me2 antibody, Thermo Fisher Scientific, cat #MA5-33383) and rcMBC103 (/5Phos/CCGCATTNNNNN CTGTCTCTTATACACATCTGACUTTTTT (SEQ ID NO: 2)/3BioTEG/. For input controls, the loading mix comprised protein G, Ab67 (histone H3 antibody, Thermo Fisher Cat #39064), and rcMBC103. The rcMBCs comprised a 7base MBC (italics), a 5b UMI (N), a 22b Illumina P5 adapter, 1 uracil for cleavage and 5 Ts for added flexibility). The bead loading mixes were incubated at room temperature for 5 minutes to allow protein G to bind to the Fc region of the antibodies. In the meantime, streptavidin coated magnetic beads were washed and combined with the bead loading mixes. Binding of the biotinylated components was complete after 30 min of incubation with gentle agitation.

The loading yields of antibody were examined by eluting the antibody from protein G at pH 2 and inspecting the eluate by SDS gel electrophoresis. Immobilized protein G and adapters were quantitated by eluting both in 95% formamide at 95° C. for 5 minutes followed by separating the components on a TBE gel. The washed beads were stored individually at 4° C. and combined for multiplexed barcoding assays.

Example 2: Digestion of Chromatin to Mononucleosomes

To package genomic DNA into a more compact, dense structure eukaryotic cells organize DNA as "chromatin".

Chromatin comprises DNA and histone proteins that are organized as octamers comprising two copies of Histone H2A, Histone H2B, Histone H3, and Histone H4. Each histone octamer is wrapped by a stretch of DNA about 140 bp in length. The unit of DNA and histone octamer is referred to as nucleosome. Nucleosomes organize into higher order structures, the 30 nm chromatin fiber. The methods for modification profiling described herein use single nucleosomes ("mononucleosomes") as an input. This example provides a protocol for extracting chromatin from yeast cells, followed by digestion of the chromatin into mononucleosomes and/or DNA-protein binding complexes.

Yeast cells are grown to an $A_{600}$OD of 0.8 at 28° C. At this stage, DNA binding protein, such as transcription factors, and histone octamers may be chemically crosslinked to DNA by treatment with formaldehyde. To this end, cells are incubated in 1% formaldehyde at room temperature for 1-25 minutes depending on the desired degree of crosslinking. After quenching the reaction in 2.5M glycine the cells are ready for harvesting by centrifugation.

Cells are resuspended in a lysis buffer (1M sorbitol, 50 mM Tris-HCl pH 7.4, 10 mM beta-mercapto ethanol, 10 mg/mL zymolyase) and are incubated at room temperature until the cell walls are mostly digested. The spheroblasts are isolated and resuspended in digestion buffer (0.5M spermidine, 1 mM beta-mercapto ethanol, 0.075% NP-40, 50 mM NaCl, 10 mM Tris-HCl pH 7.4, 5 mM MgCl2, 1 mM $CaCl_2$)). Next, micrococcal nuclease is added to a final concentration of 0.07 units/uL. Incubating the reaction for 25 minutes at 37° C. digests the chromatin into mononucleosomes. The reaction is stopped by adding an excess of EDTA and nucleosomes are further purified using anion-exchange midi columns (Epoch Life Sciences). Loading of the nucleosomes is accomplished in buffer A at moderate salt concentration (25 mM MES pH 6, 10% sucrose, 10% glycerol, 400 mM NaCl). After three washes with buffer A, the nucleosomes are eluted with buffer B (25 mM MES pH 6, 10% sucrose, 10% glycerol, 750 mM NaCl, 1 mM EDTA). The nucleosomes can be diluted and stored at −80° C. in buffer C (10 mM Tris-HCl pH 7.5, 1 mM EDTA, 25 mM NaCl, 2 mM DTT, 20% glycerol). The foregoing protocol typically produces >80% of mononucleosomes.

Example 3: Methods for End-Repair of Nucleosomal DNA

Mechanical and enzymatic shearing of chromatin produces nucleosomes with non-uniform DNA ends. For example, the 3'ends may be degraded and a mixture of 3' and 5' phosphorylated ends may be present. The barcoding methods described below employed different ligations methods, which require 5' phosphorylation and 3' dephosphorylation, and either blunt ends ("blunt end ligation") or a single 3'dA overhang ("sticky end ligation") This example illustrated repairing nucleosomal DNA to be compatible with these barcoding chemistries.

Blunt end ligation. Nucleosomal DNA was dephosphorylated by incubating in buffer 1 (50 mM Potassium Acetate, 20 mM Tris-acetate, 10 mM Magnesium Acetate, 100 µg/ml Recombinant Albumin pH 7.9® 25° C.) and 1 unit of recombinant shrimp alkaline phosphatase (rSAP) for 30 min at 37° C. The reaction was stopped by adding excess EDTA and used as an input for immunoprecipitation (IP) using a pool of the two bead types prepared according to Example 1. Blunting of the nucleosome DNA was performed with T4 DNA polymerase. This enzyme exhibits a strong 3'-5' exonuclease activity, which prevents the formation of 3'overhangs in the gap fill reaction. After immunoprecipitation, beads were resuspended in blunting buffer (50 mM NaCl, 10 mM Tris-HCl, 10 mM MgCl2, 100 µg/ml Recombinant Albumin pH 7.9® 25° C.). 0.5 units of T4 DNA polymerase was added to the DNA in the presence of 0.1 mM dNTPs and incubated for 15 minutes at room temperature. The reaction was stopped by addition of EDTA.

Sticky end ligation. Nucleosomal DNA was dephosphorylated as described above and used as an input for immunoprecipitation. Blunt ending was performed as described above after immunoprecipitation, followed by washing the beads with HBST300 buffer. A single base 3'dA-overhang was installed by incubating with 5 units of Klenow Fragment 3'->5' exo- in adenylation buffer (50 mM NaCl, 10 mM Tris-HCl, 10 mM MgCl2, 1 mM DTT, pH 7.9® 25° C.), supplemented with 0.1 mM dATP. The reaction was stopped by addition of EDTA.

Example 4: Detection of Histone Modifications H3K4Me3 and H3K4Me2 by Bead-Based Barcoding This example describes the protocol for the identification of one or more histone modifications concurrently using the library preparation workflow depicted in FIG. 5A. The protocol steps include barcoding by ligation after the immunoprecipitation of nucleosomes and end-repair, to identify the modification state, removal of the histone core to improve DNA accessibility, reverse strand synthesis, ligation of the second adapter and PCR amplification.

1 µg of HeLa mononucleosome (EpiCypher Cat #16-0002) was combined with 0.25 µL of SNAP-ChIP® K-Met-Stat Panel (EpiCypher Cat #19-1001) and 0.5 µL SNAP-ChIP® K-AcylStat Panel (EpiCypher Cat #19-3001). The SNAP-CHIP® panels are commercial pools of synthetic mononucleosomes with known modification state. For example, the SNAP-ChIP® K-MetStat Panel contains distinctly modified mononucleosomes assembled from recombinant human histones expressed in *E. coli* wrapped by 147 base pairs of barcoded Widom 601 positioning sequence DNA. The panel is comprised of a pool of 1 unmodified plus 12 histone H3 post-translational modifications: H3K4me1, H3K4me2, H3K4me3, H3K9me1, H3K9me2, H3K9me3, H3K27me1, H3K27me2, H3K27me3, H3K36me1, H3K36me2, H3K36me3. Each distinctly modified nucleosome is distinguishable by a unique sequence of DNA ("barcode") at the 3' end that can be deciphered by next-generation sequencing. Each of the 16 nucleosomes in the pool is wrapped by 2 distinct DNA species, each containing a distinct barcode ("A" and "B") allowing for an internal technical replicate. The SNAP-ChIP® K-AcylStat Panel is manufactured from the same building blocks comprising a pool of 1 unmodified plus 15 H3 histone modifications: H3K4ac, H3K9ac, H3K14ac, H3K18ac, H3K23ac, H3K27ac, H3K36ac, H3K9bu, H3K9cr, H3K18bu, H3K18cr, H3K27bu, H3K27cr, H3K27acS28phos, H3K4,9, 14,18ac. This 2-plex experiment is expected to produce positive signals for H3K4me3 and H3K4me2, and negative signals for the unmodified or differently modified nucleosomes.

Nucleosomes were dephosphorylated according to Example 3, and diluted in HBST300 buffer. 10% of the dephosphorylated nucleosomes were transferred to a new tube for processing in parallel as the input control. For IP sample, nucleosomes were immunoprecipitated using a pool of the H3K4me3 and H3K4me2 bead types prepared according to Example 1. Nucleosomes for the input control were immunoprecipitated using a single bead type prepared with generic histone H3 binding domain and rcMBC adapter. While the IP reaction enriches the nucleosomes that exhibit the modifications targeted by the binding domains, the intent of the input control is to capture all nucleosomes with an H3 histone core, regardless of modification state. This kind of input normalization is necessary to control for unevenness in the genome representation of the input. To identify regions with histone modifications the read coverage obtained for the IP is divided by the reads observed for the input sample.

The immunoprecipitation was allowed to proceed for one hour at room temperature and excess nucleosomes were removed by washing with RIPA buffer (50 mM Tris HCl, 300 mM NaCl, 1.0% (v/v) NP-40, 0.5% (w/v) Sodium Deoxycholate, 1.0 mM EDTA, 0.1% (w/v) SDS) and HBST300 buffer. DNA from immunoprecipitated nucleosomes were blunt ended according to Example 3. Adapter ligation was induced by suspending the bead bound nucleosomes in ligation buffer (50 mM Tris-HCl pH 7.5, 150 mM NaCl, 10 mM MgCl2, 1 mM ATP, 10% PEG-8K, 0.05% Tween20, and 400 U T4 DNA ligase), supplemented with 0.5 uM of each MBC101 (/5deoxyI//ideoxyI//ideoxyI/CGATCAC) and MBC103 (/5deoxyI//ideoxyI//ideoxyI/AATGCGG). The purpose of the MBC oligos is to provide a double-stranded ligation junction, however, deliberately only the adapter strand that was coupled to the beads was ligated because the 5'end of the nucleosomes was not phosphorylated. This way the MBC was only introduced to one end of the DNA.

Following barcoding, histones and antibodies were removed by incubating beads in removal buffer (5 mM DTT, 10 mM HEPES pH 7.5, 50 mM NaCl, 0.05% Tween 20). Complementary DNA strands were synthesized in a standard primer extension reaction with 8 units of Bst 3.0 DNA Polymerase in extension buffer (1 mM of each dNTP, 20 mM Tris-HCl, 10 mM (NH4)2SO4, 50 mM KCl, 2 mM MgSO4, 0.1% Tween® 20, pH 8.8® 25° C., 0.5 uM extension primer (GTCAGATGTGTATAAGAGACAG; SEQ ID NO: 3) using the following thermocycler program: 72° C. 2 min-55° C. 5 min-65° C. 15 min-72° C. 5 min-80° C. 5 min-16° C. hold. The second sequencing adapter was introduced by repeating the same ligation step that was used for introducing the MBC adapters in the presence of 100 units T4 DNA ligase and 10 units T4 Polynucleotide Kinase to phosphorylate the 5'ends of bead strands. The second adapter is universal and comprises only the Illumina P7 adapter (AGACGTGTGCTCTTCCGATCT; SEQ ID NO: 4) and its complement (GATCGGAAGAGC; SEQ ID NO: 5). Adapter ligated DNA was treated in 0.1 N NaOH to remove the complementary DNA strand that was not coupled to the beads. The DNA coupled to the beads was PCR amplified using Illumina index primers and the NEBNext Ultra II Q5 master mix (NEB) following the manufacturer's protocol. Indexed libraries were purified with AMPure beads, inspected on a 4% agarose gel, quantified by Qubit (Thermo Fisher) and sequenced.

Figure 10:
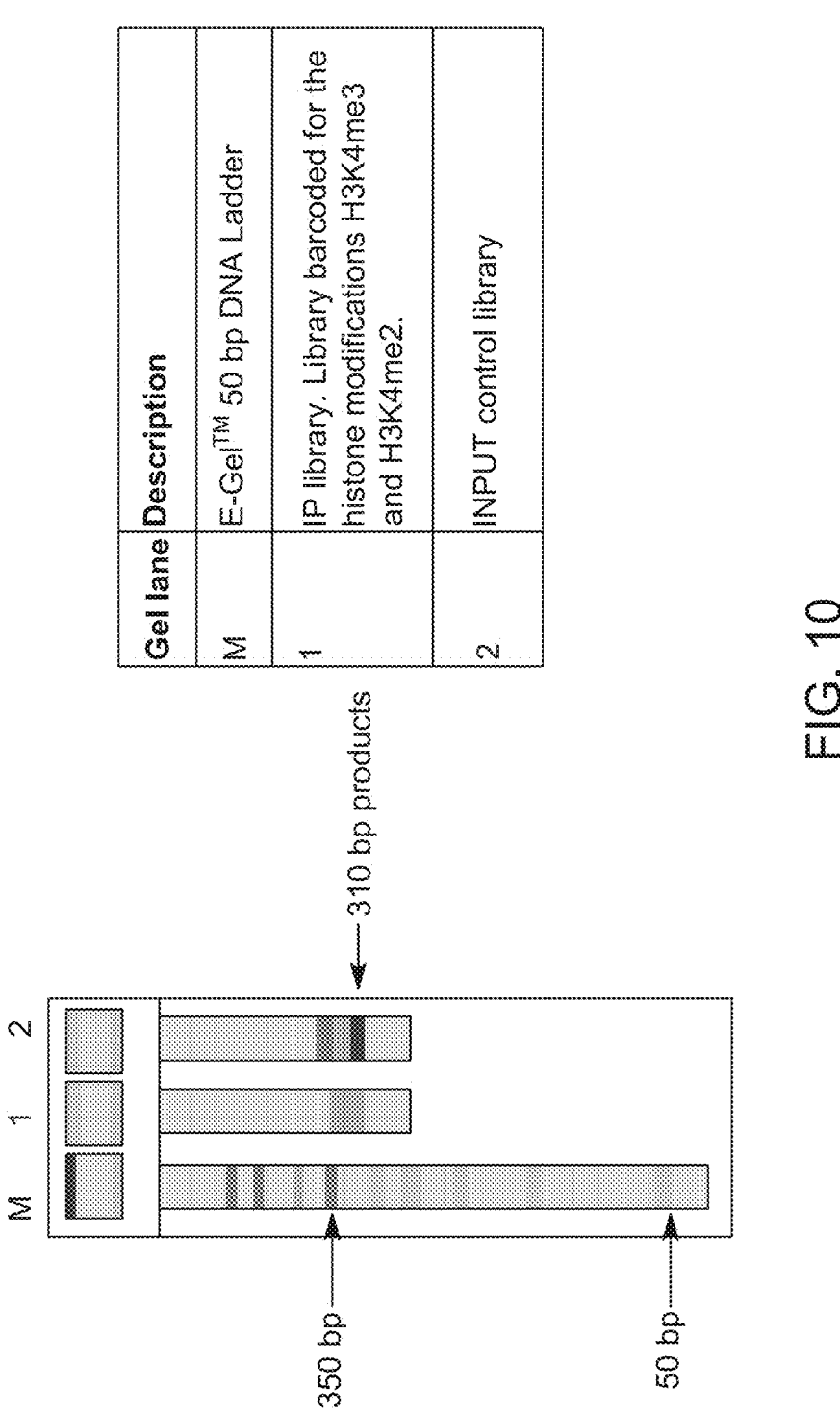
FIG. 10 depicts an agarose gel showing the DNA libraries obtained for the multiplexed detection of the histone modifications H3K4me3 and H3K4me2 in HeLa nucleosomes using the workflow FIG. 5A as described in example 4.
Figure 11A:
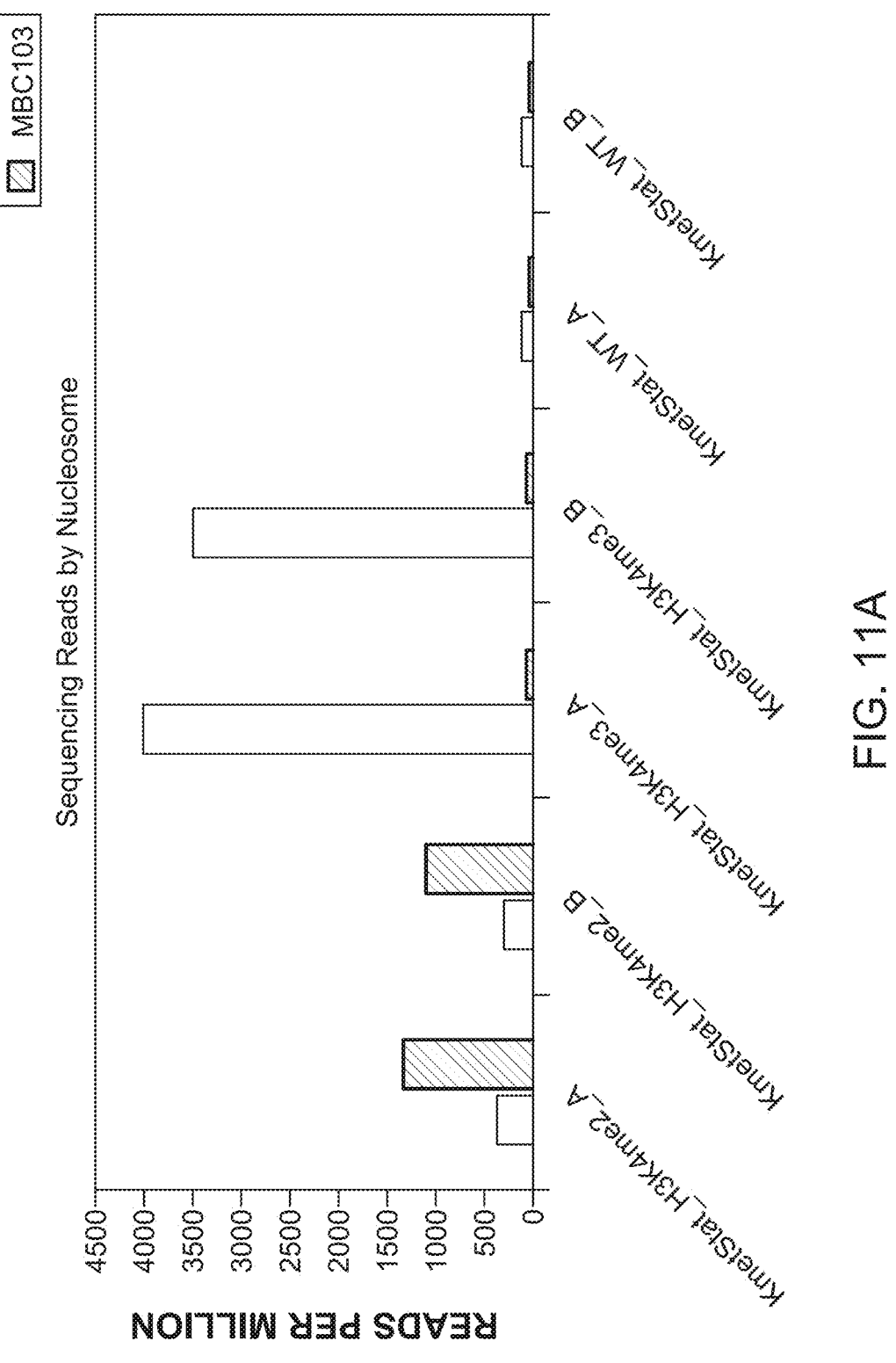
FIGS. 11A-11F show sequencing results obtained for a bead-based 2-plex barcoding assay using HeLa sample spiked with a synthetic nucleosome control panel to serve as positive and negative controls.
Figure 11B:
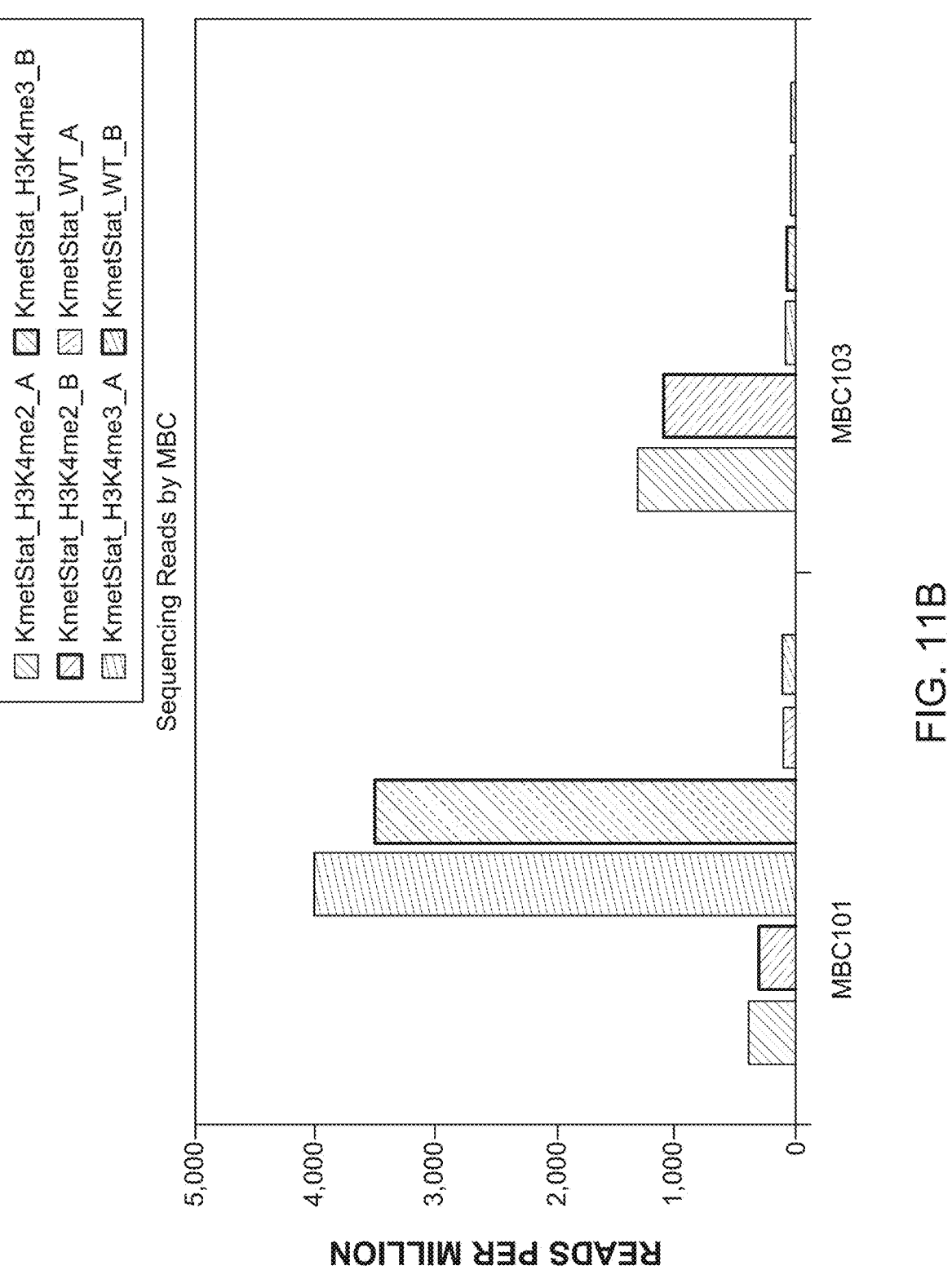
Figure 11C:
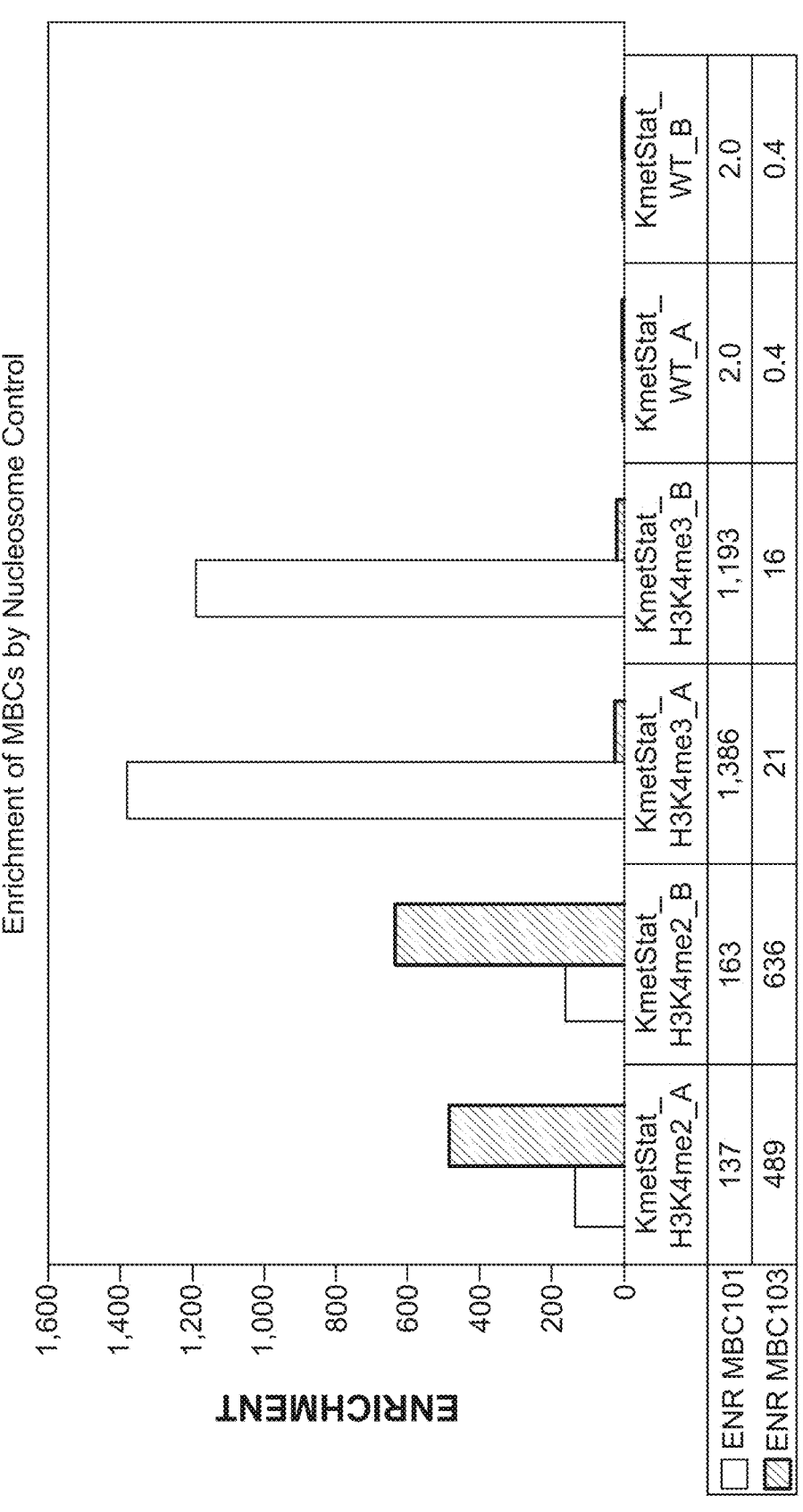
Figure 11D:
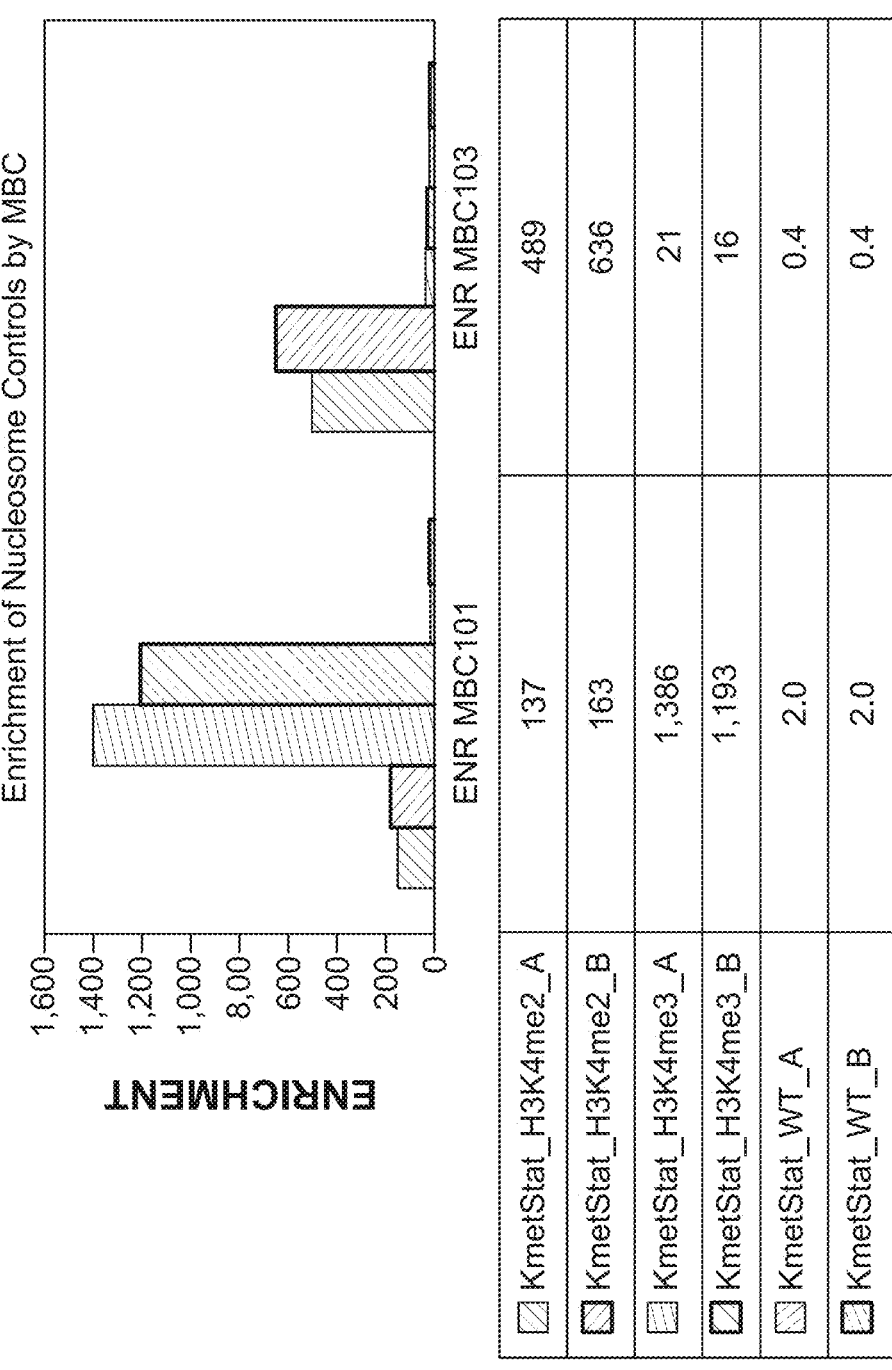
Figure 11E:
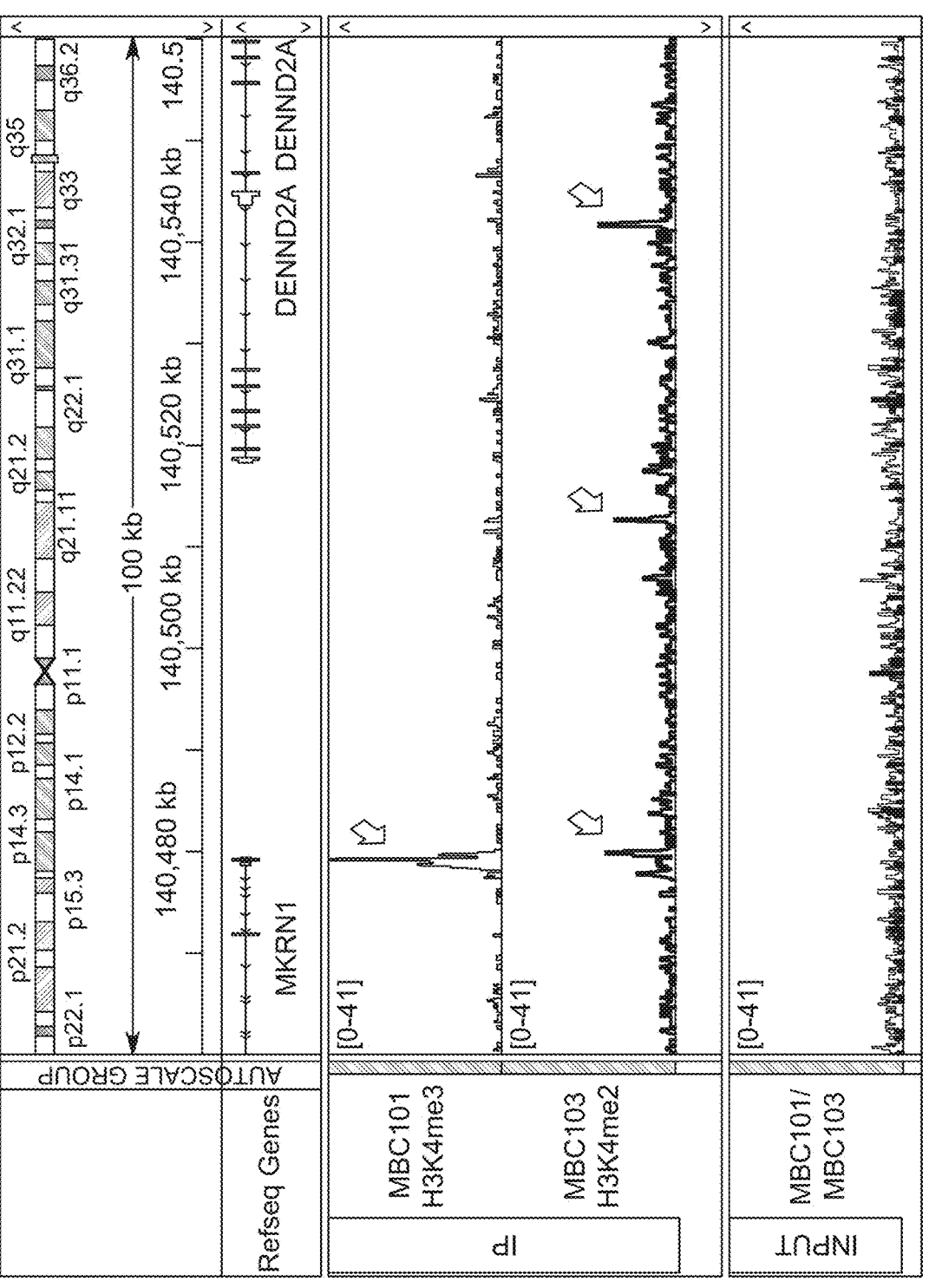
Figure 11F:
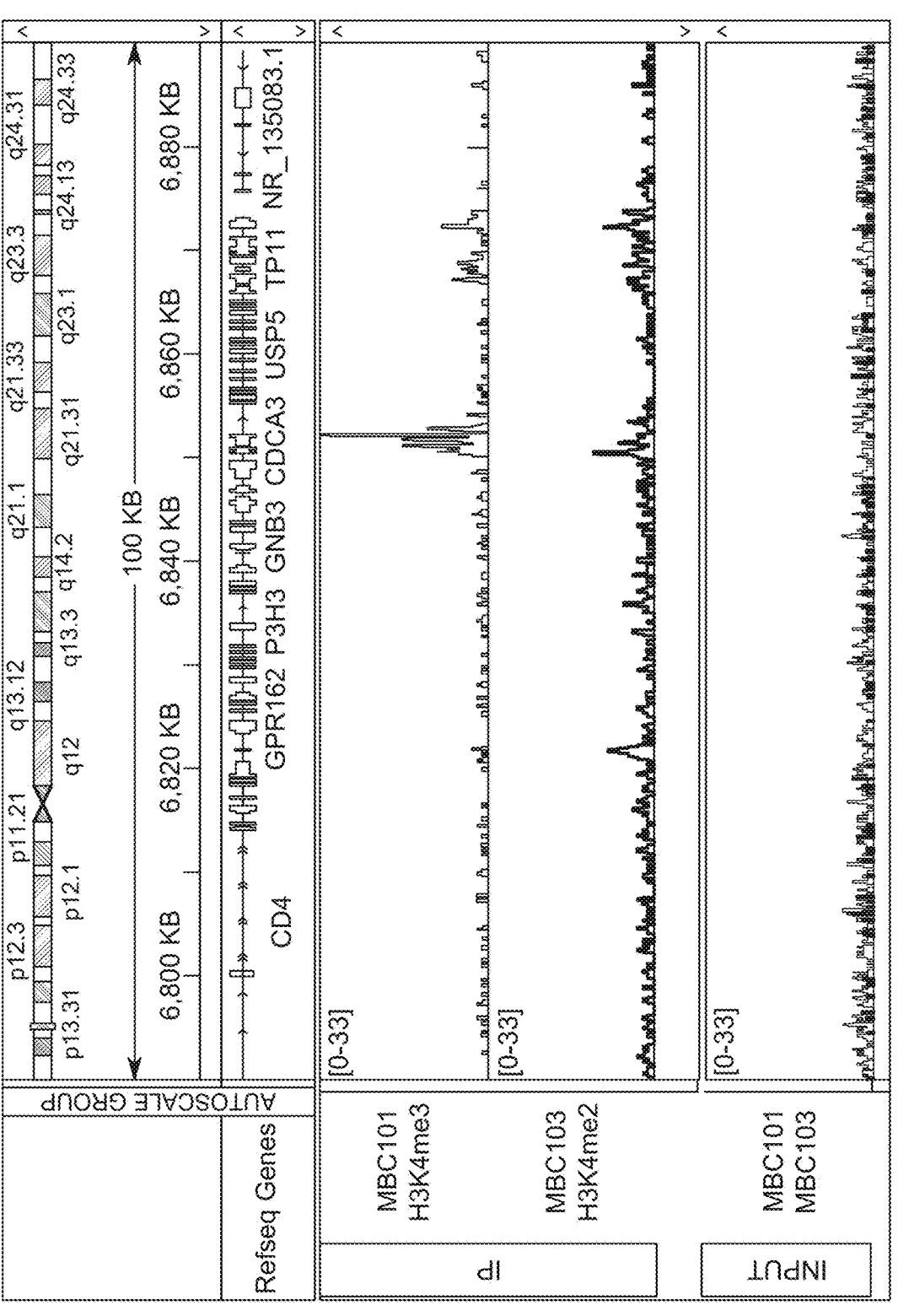

FIG. 10 shows the library QC gel. Sharp bands of the expected size of ~310 bp are visible for the IP and input libraries with few side products. After sequencing, the raw reads were aligned against the human genome (for the HeLa sample) and the SNAP-CHIP sequence reference. Each SNAP-Chip nucleosome was identified based on its Widom 601 barcode. The reads with MBCs introduced by our barcoding assay were located, deduplicated based on their UMIs, and normalized to Reads per Million (RPM) to account for sequencing depth variability. FIG. 11A shows the MBC distribution for a set of SNAP-CHIP spike-in controls. In agreement with the bead design, which associated H3K4me3 with the MBC101 adapter, the KmetStat_H3K4me3 fragments are enriched for MBC101. Similarly, KmetStat_H3K4me2 fragments are accurately enriched in MBC103. The KmetStat_WT unmodified fragments have very few reads in either MBC101 or MBC102 relative to the H3K4me3 and H3K4me2 fragments, suggesting very low nonspecific background. FIG. 11B shows the SNAP-CHIP spike-in control representation for each MBC. For MBC101, the KmetStat_H3K4me3 fragments are the most represented fragments. For MBC103, KmetStat_H3K4me2 fragments are the most represented fragments. FIGS. 11C and 11D show the corresponding enrichment analysis. Enrichment values are a measure of signal noise and are calculated by dividing RPM(IP) by the RPM(INPUT). Crosstalk is determined by the fraction of enrichment of off-target MBC relative to enrichment on on-target MBC. Crosstalk of KmetStat_H3K4me2 and KmetStat_H3K4me3 fragments are 25-28%, and 1.3-1.5%, respectively, indicating that the H3K4me2 antibody is less specific than the H3K4me3 antibody. FIGS. 11E and 11F provide examples of genomic regions with histone modifications for the HeLa sample. Shown are the raw reads along the genome coordinate for IP sequencing reads exhibiting either MBC101 (top track) or MBC103 (middle track). While the input sample (bottom track) shows even read coverage along the genome coordinate, the MBC tracks exhibit spikes that indicate read enrichment in genomic regions with histone modifications.

In summary, this example demonstrated the identification of two histone modifications (H3K4me2 and H3K4me2) in HeLa and in synthetic control nucleosomes using a bead-based barcoding format that employs a pool of different bead types. Each bead type displays one binding domain and one barcoded adapter to interrogate one type of histone modification. The binding domain pulls the targeted nucleosomes on the bead surface where they are barcoded with the barcoded surface adapters.

Example 5: Preparation of Nucleosome Binding Molecules

Nucleosome binding molecules are generated by site-specifically labeling antibodies using a SiteClick Antibody Azido Modification Kit (Thermo Fisher, cat. no. 520026). SiteClick labeling uses enzymes to specifically attach an azido moiety to the heavy chains of an IgG antibody, ensuring that the antigen binding domains remain unaltered for binding to the antigen target. This site selectivity is achieved by targeting the carbohydrate domains present on essentially all IgG antibodies regardless of isotype and host species. Beta-galactosidase catalyzes the hydrolysis of a 0-1,4 linked D-galactopyranosyl residue followed by the attachment of an azido-galactopyranosyl using an engineered β-1,4-galactosyltransferase. Once azido-modified, a DBCO (Dibenzocyclooctyl) labeled ds-MBC adapter is conjugated to the Fc region. In the first barcoding cycle the ligation junction on the nucleosome side exhibits a single 3' A-overhang, which is why the DBCO oligo ends in a single 3'T: e.g. DBCO/TTAAT/TAAGCATCGATCAC*T (SEQ ID NO: 6) and 5Phos/GTGATCGATGCTTAAT/TAA (SEQ ID NO: 7). The first cycle DBCO labeled oligo comprises a PacI restriction site (underlined and italicized, the slash indicates the cleavage site), a short 4b filler sequence, a 7b MBC (bold italics), a phosphorothioate (*) and a 3'T overhang. In the second and higher barcoding cycles, after releasing the first adapter by PacI treatment, the ligation junction on the nucleosome side exhibits a 3' TA-overhang, which is why the DBCO oligo must end in 5'AT: DBCO/TTAAT/TAATGCATTC*A*T (SEQ ID NO: 8) and 5Phos/GAAT-TGCTTAAT/TAA (SEQ ID NO: 9). Pac I is selected as a restriction enzyme because its recognition motif is extremely rare in the human genome. Uncoupled MBC adapter is removed using a size-exclusion column. Site-Click™ labeling results in antibodies that exhibited one or two adapters, as can be deduced by gel electrophoresis.

Example 6: Co-Localization of Histone Modifications H3K4Me3 and H3K9Ac on the Same Nucleosome by Serial Barcoding This example employs nucleosome binding molecules, comprising an antibody tethered to an MBC adapter, for the identification of histone modification. The method may be used to detect a single modification per nucleosome, or multiple modifications, depending on the number of barcoding cycles that are performed.

The first step is the preparation of a surface that displays P7 Illumina adapters at single molecule spacing. In a second step, nucleosomal DNA is ligated to the P7 adapter, which generates a substrate with immobilized nucleosomes that are spatially segregated and cannot interact with their nearest neighbors. This is achieved by suspending streptavidin beads in a mixture comprising 3'biotinylated, double-stranded Illumina P7 adapter (5Phos/GATCG-GAAGAGCACACGTCTCTTTTTT (SEQ ID NO: 10)/3BioTEG/ and AGACGTGTGCTCTTCCGATC*T (SEQ ID NO: 11)) and a 100,000 molar excess of biotinylated PEG (Broadpharm, cat #BP-23759) in 1×PBST buffer. The biotinylated PEG provides a lateral diluent and passivates the surface to reduce non-specific binding.

A plurality of nucleosomes are prepared for sticky end ligation according to Example 3, above, and are ligated to the P7 adapter using T4 DNA ligase (50 mM Tris-HCl pH 7.5, 150 mM NaCl, 10 mM MgCl$_2$, 1 mM ATP, 10% PEG-8K, 0.05% Tween20, 400 U T4 DNA ligase). After washing with RIPA buffer, the bead substrates are suspended in a solution comprising a single or multiple nucleosome binding molecules that exhibit the adapter architecture designed for the first barcoding cycle. The antibody-adapter conjugates are allowed to bind, and the first MBC adapter is ligated to the free end of the nucleosome by T4 DNA ligase, as described above. To release the antibody, the adapter is cleaved by treating with PacI restriction enzyme in Cut-Smart buffer (50 mM Potassium Acetate, 20 mM Tris-acetate, 10 mM Magnesium Acetate, 100 μg/ml BSA). A second barcoding cycle is initiated by repeating the binding step with a single or a pool of multiple nucleosome binding molecules with the adapter architecture designed for the second barcoding cycle. After cleavage with restriction enzyme, this process may be repeated any number of times, using nucleosome binding molecules in each cycle that exhibit an MBC that is specific to the cycle number and binding domain. To complete the library the nucleosomal DNA is ligated to a double stranded cap that comprises the P5 Illumina adapter (CTACACGACGCTCTTCCGATCT*A*T (SEQ ID NO: 12) and 5Phos/AGATCGGAAGAGCGTCGTGTAG (SEQ ID NO: 13)) and subjected to index PCR with NEBNext Ultra II Q5 master mix (NEB), as described in example 4.

The described barcoding format is compatible with planar or bead surfaces as long as the immobilized nucleosomes are spaced out at a distance that eliminates nearest neighbor interactions. Each barcoding step may employ a single type of nucleosome binding conjugate or a pool of different conjugates. The assay attaches a string of MBCs indicative of the identified modifications to the nucleosome DNA, providing the first assay for co-localizing histone modifications with single molecule resolution.

Example 7: Cyclic Encoding of Immunoprecipitated Nucleosomes on Bead Substrates This example employs multiple barcoding cycles, each cycle in the presence of a single binding domain, and adapters in solution to attach MBCs to the DNA ends of immunoprecipitated nucleosomes in a modification-specific manner. The protocol describes steps for immunoprecipitation, end repair, barcoding, gap fill, elution, and a final capping step to add sequencing adapters as applicable to the workflows shown in FIGS. 6 and 9. This example uses a hairpin (HP) adapter that allows for the introduction of a UMI adjacent to the MBC in accordance with FIG. 9. Despite the importance of UMIs for PCR error correction and the deduplication of sequencing reads, it is non-trivial to introduce them via a double-stranded ligation because the complement of the UMI needs to be synthesized in situ.

Bead substrates were prepared by loading a histone H3 or modification specific antibody to magnetic protein G beads following the manufacturer's protocol. For IP sample, Ab42 (histone H3K4me3 antibody, Epicypher, cat #13-0041) was loaded to Protein G beads. For INPUT control, Ab67 (histone H3 antibody, Thermo Fisher, Cat #39064) was loaded to protein G beads in a separate loading reaction.

1 μg of HeLa mononucleosome (EpiCypher Cat #16-0002) was combined with 0.25 μL of SNAP-ChIP® K-Met-Stat Panel (EpiCypher Cat #19-1001) and 0.5 μL SNAP-ChIP® K-AcylStat Panel (EpiCypher Cat #19-3001). The nucleosome mix was diluted in HBST300 buffer and split into two reactions such that 90% and 10% of the nucleosome mix was used as input for immunoprecipitation on Ab42 loaded beads and Ab67 loaded beads, respectively. Immunoprecipitation was allowed to proceed at room temperature for one hour with gentle agitation.

The initial end repair comprised blunting, 5'phosphorylation and 3'dA-tailing steps. Blunting and 5'phosphorylation of the DNA on the immunoprecipitated nucleosomes were performed with T4 DNA polymerase and T4 Polynucleotide Kinase in one reaction. After immunoprecipitation, beads were resuspended in 1×NEB r2.1 buffer. 0.5 units of T4 DNA polymerase and 5 units of T4 Polynucleotide Kinase are added to the beads in the presence of 0.1 mM dNTPs, 1 mM ATP, 2 mM DTT and incubated for 15 minutes at 16° C.-15 minutes at 23° C. The reaction was stopped by addition of EDTA, followed by HBST300 wash. The beads were resuspended in 1×NEB r2.1 buffer. A single base 3'A-tail was installed to nucleosome DNA ends by incubating for 15 minutes at 37° C. with 2.5 units of Klenow Fragment 3'→5' exo- in 1×NEB r2.1 buffer, supplemented with 0.1 mM dATP. The reaction was stopped by addition of EDTA, followed by washing with HBST300 buffer.

Barcoding was performed by ligating an HP-MBC adapter to nucleosome DNA ends. The HP-MBC adapter comprises a double stranded MBC ligation junction with a single base 3'dT overhang. The other end of the double stranded MBC region is linked by a single stranded loop segment consisting of an uracil and an UMI sequence. To focus the experiment on testing the cyclic barcoding chemistries, the elution and re-immunoprecipitation steps were omitted in this example. Instead, H3K4me3 was detected by MBC107 in cycle 1 and by MBC109 in cycle 2 without eluting the nucleosome.

Barcoding was induced by suspending the bead bound nucleosomes in ligation buffer (50 mM Tris-HCl pH 7.5, 150 mM NaCl, 10 mM MgCl2, 1 mM ATP, 10% PEG-8K, 0.05% Tween20, and 400 U T4 DNA ligase), supplemented with 0.5 uM of HP-MBC107 (CGGTAGTUNNNNNAC-TACCGT, SEQ ID NO: 14). The purpose of the HP-MBC adapter was to provide a double-stranded sticky end ligation junction, however, deliberately only the 3'dT end was coupled to the nucleosome DNA ends because the 5'end of the HP-MBC adapter was not phosphorylated. The barcoding reaction was incubated for 15 minutes at 20° C.-15 minutes at 25° C., then stopped by addition of EDTA and washing by HBST300 buffer.

Following MBC107 ligation, the barcoded nucleosome DNA ends were cleaved at the uracil sites to prepare for subsequent gap filling. Cleavage reaction was performed by incubating the beads with 0.5 units of USER enzyme in 1×NEB rCutSmart buffer for 15 minutes at 37° C. The reaction was washed by HBST300 buffer to expose single stranded 5'overhang consisting of MBC and UMI.

The 5'overhang was gap filled and 3'dA tailed by incubating for 15 minutes at 37° C. with 2.5 units of Klenow Fragment 3'→5' exo- in 1×NEB r2.1 buffer, supplemented with 0.2 mM dNTP. The reaction was stopped by addition of EDTA, followed by washing with HBST300 buffer. This completes the first cycle of barcoding.

Because the barcoded nucleosome DNA ends are not tethered to the bead surface, the nucleosomes may be eluted from the bead surface, and used as the input for subsequent immunoprecipitation and barcoding cycles. This allows for serial barcoding of histone modifications that coexist on the same nucleosome. The nucleosomes may be eluted by various methods as illustrated in Example 8. As mentioned above, nucleosome elution was skipped in this example and we proceeded to ligation of MBC109 after ligating MBC107.

Beads with bound nucleosomes that were barcoded by HP-MBC107 in the previous step were subjected to a new cycle of barcoding ligation with HP-MBC109 (ACGAGAGUNNNNNCTCTCGTT, SEQ ID NO: 15), cleavage by USER enzyme, and gap filling and 3'dA tailing.

Following the last barcoding cycle, the nucleosome underwent a capping cycle where universal sequencing adapter was attached to DNA ends for library amplification by PCR. The ligation reaction was induced by suspending the bead bound nucleosomes in ligation buffer (50 mM Tris-HCl pH 7.5, 150 mM NaCl, 10 mM MgCl2, 1 mM ATP, 10% PEG-8K, 0.05% Tween20, and 400 U T4 DNA ligase), supplemented with 0.5 uM of HP-U adapter (/5Phos/GATCGGAAGAGCACACGTCTUTACACGACGCTCTTCCGATCT, SEQ ID NO: 16).

The HP-U adapter provided a bell-shaped conformation with a double-stranded sticky end ligation junction as well as priming sites for library amplification. The adapter ligation reaction was incubated for 15 minutes at 20° C.-15 minutes at 25° C., then stopped by addition of EDTA and washing by HBST300 buffer. After the adapter ligation, the loop ends were separated to Y-shaped ends by cleavage with USER enzyme. Cleavage reaction was performed by incubating the beads with 0.5 units of USER enzyme in IX NEB rCutSmart buffer for 15 minutes at 37° C. The reaction was washed by HBST300 buffer.

Adapter ligated nucleosome DNA were subsequently eluted by incubating 0.12 units of thermolabile Proteinase K (New England Biolabs, Cat #P8111S) in a reaction mix consisting of RIPA buffer, supplement with 0.4% SDS and 5 mM DTT. The DNA elution reaction was allowed to proceed for one hour at 37° C., then for 10 minutes at 65° C. The elution was further purified by AMPure beads. The DNA was PCR amplified using Illumina index primers and the NEBNext Ultra II Q5 master mix (NEB) following the manufacturer's protocol. Indexed libraries were purified with AMPure beads, assessed on an agarose gel, quantified by Qubit (Thermo Fisher) and sequenced.

Figure 12:
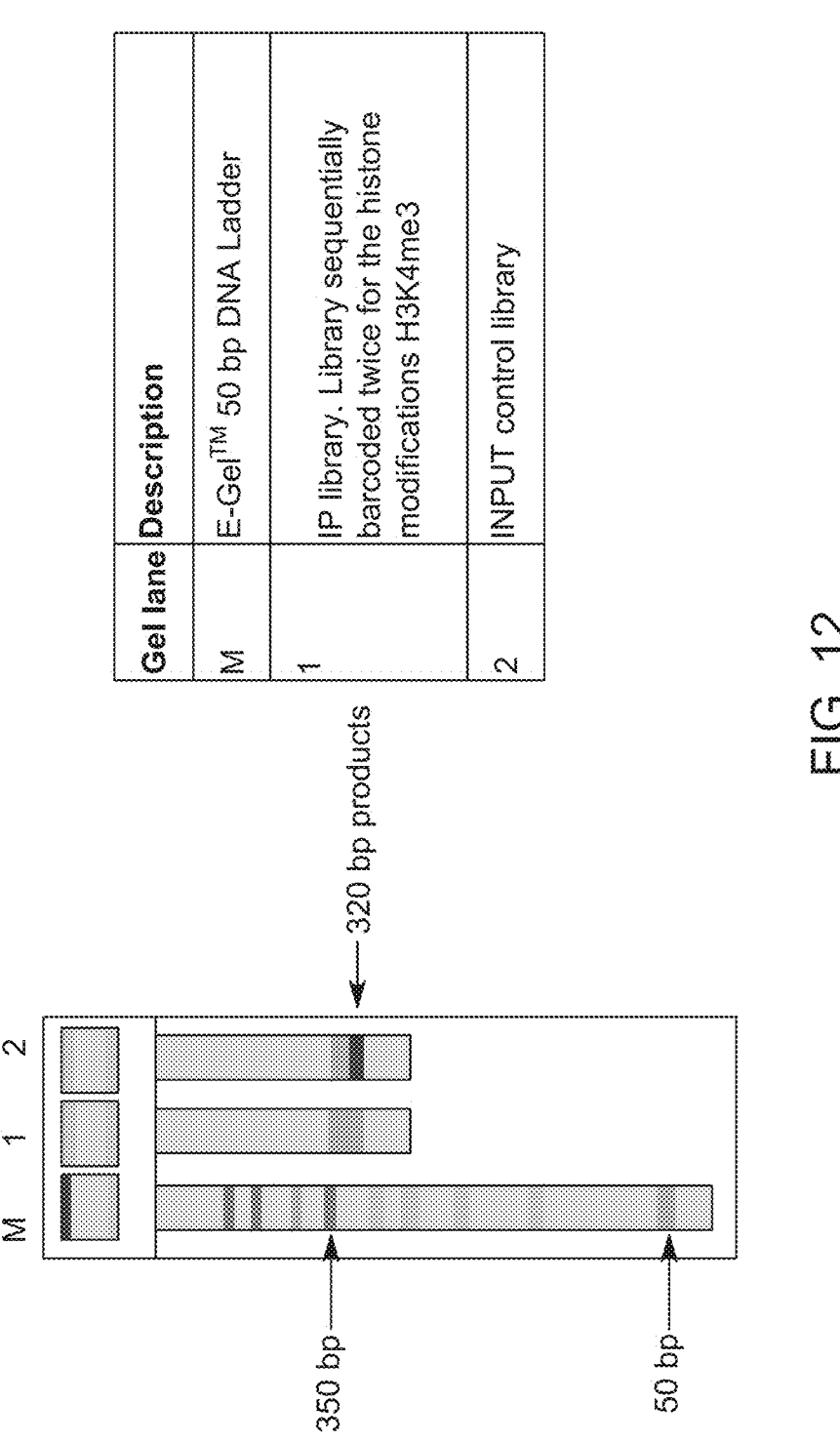
FIG. 12 depicts an agarose gel showing the DNA libraries obtained with the histone modification co-localization workflow shown in FIG. 9 and described in example 7.
Figure 13A:
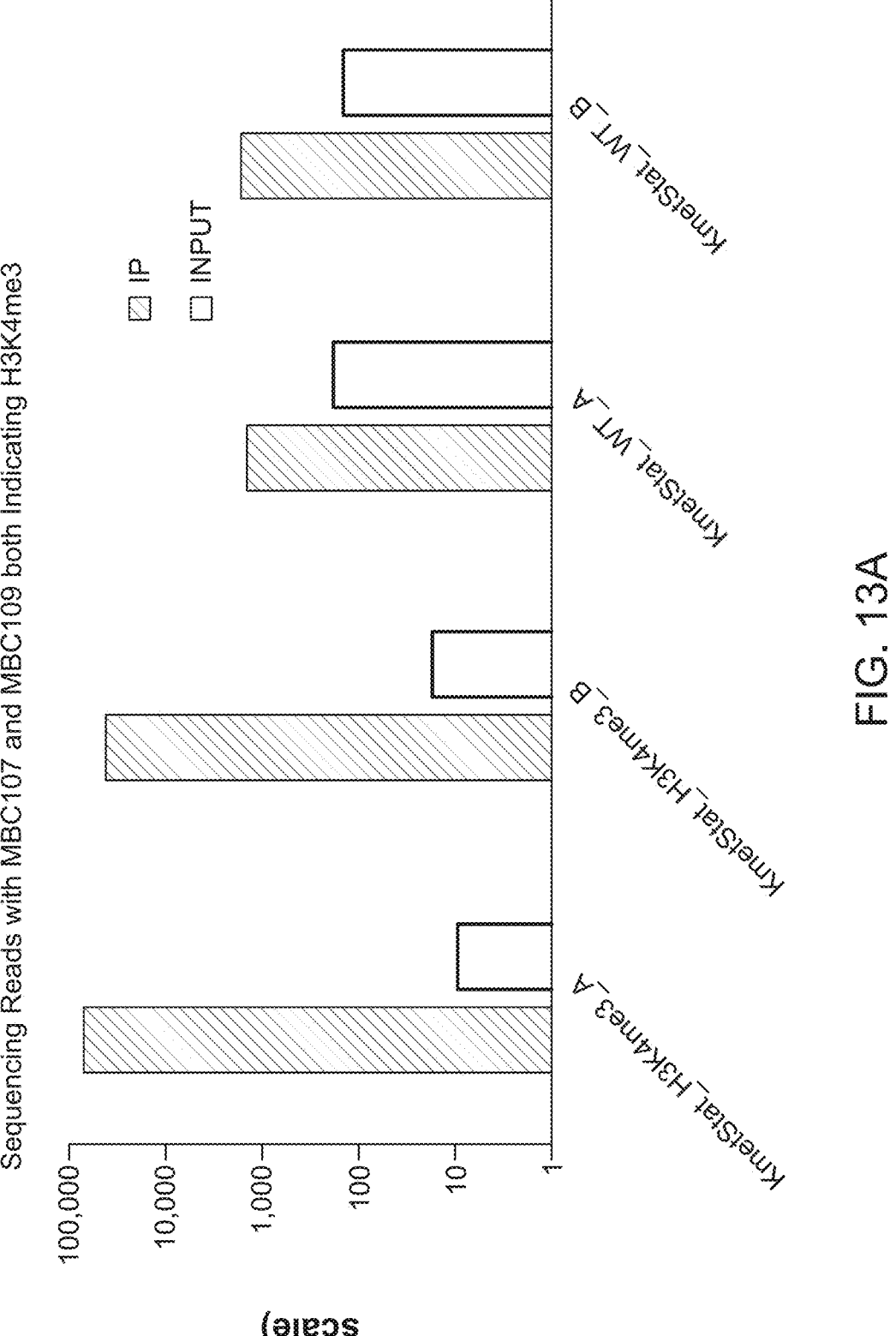
FIGS. 13A-13B show results for the co-localization workflow described in FIG. 9 using HeLa sample spiked with a synthetic nucleosome control panel to serve as positive and negative controls. In this example, we tested the ability to barcode sequentially, without eluting the nucleosome. In the first cycle H3K4me3 was identified by attaching MBC107. In the second cycle, H3K4me3 was identified again, this time by attaching MBC109.

FIG. 12 shows an agarose gels with the IP and input libraries produced with the protocol above. The gel shows clean libraries roughly ~320 bp in size as theoretically predicted. FIG. 13A shows the number of SNAP-Chip fragments that contained MBC107 and MBC109 after IP and barcoding relative to the input controls. The KmetStat_H3K4me3 fragments were clearly enriched for MBC109, in agreement with the experimental design.

Figure 13B:
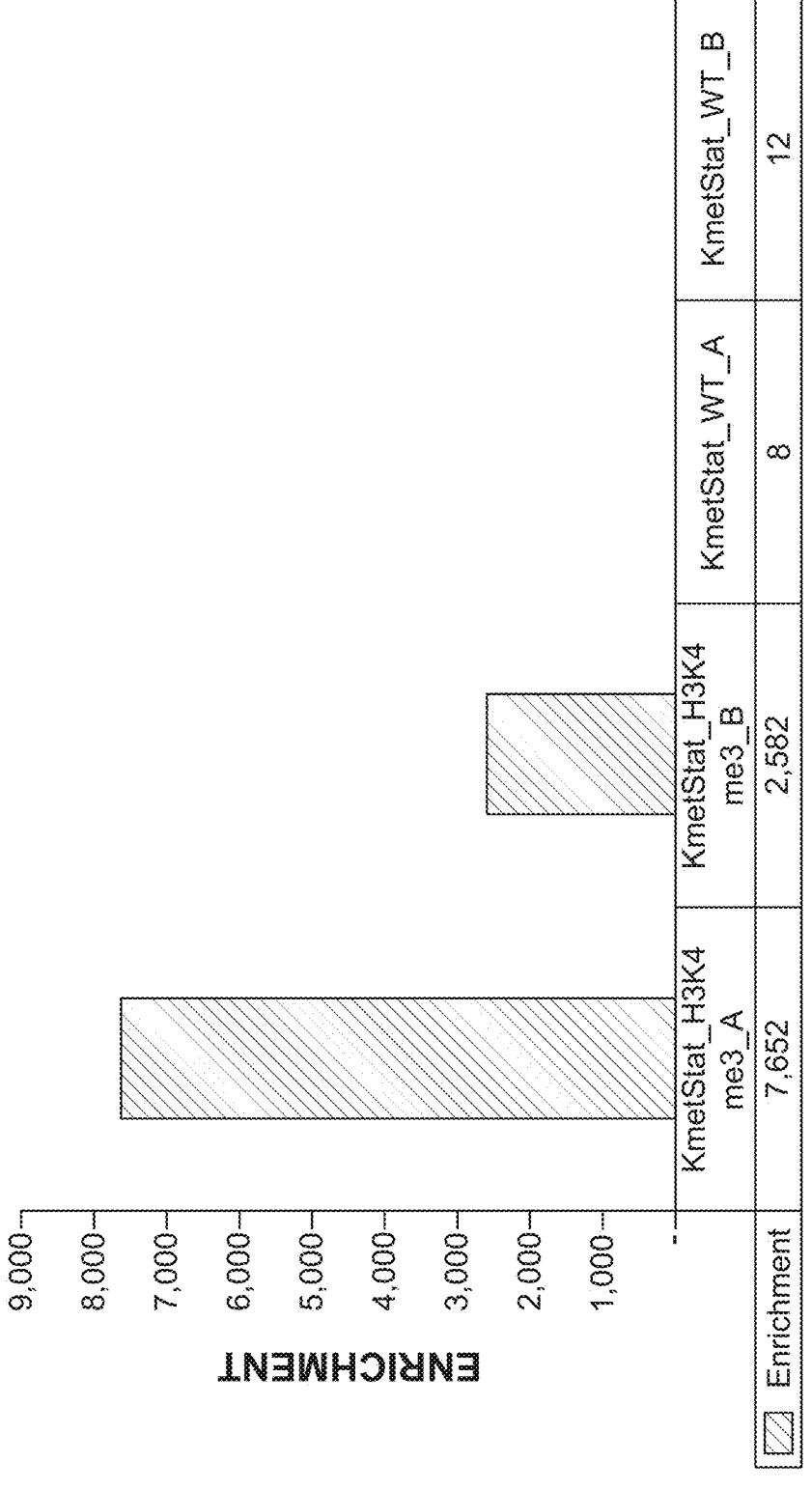
Figure 15A:
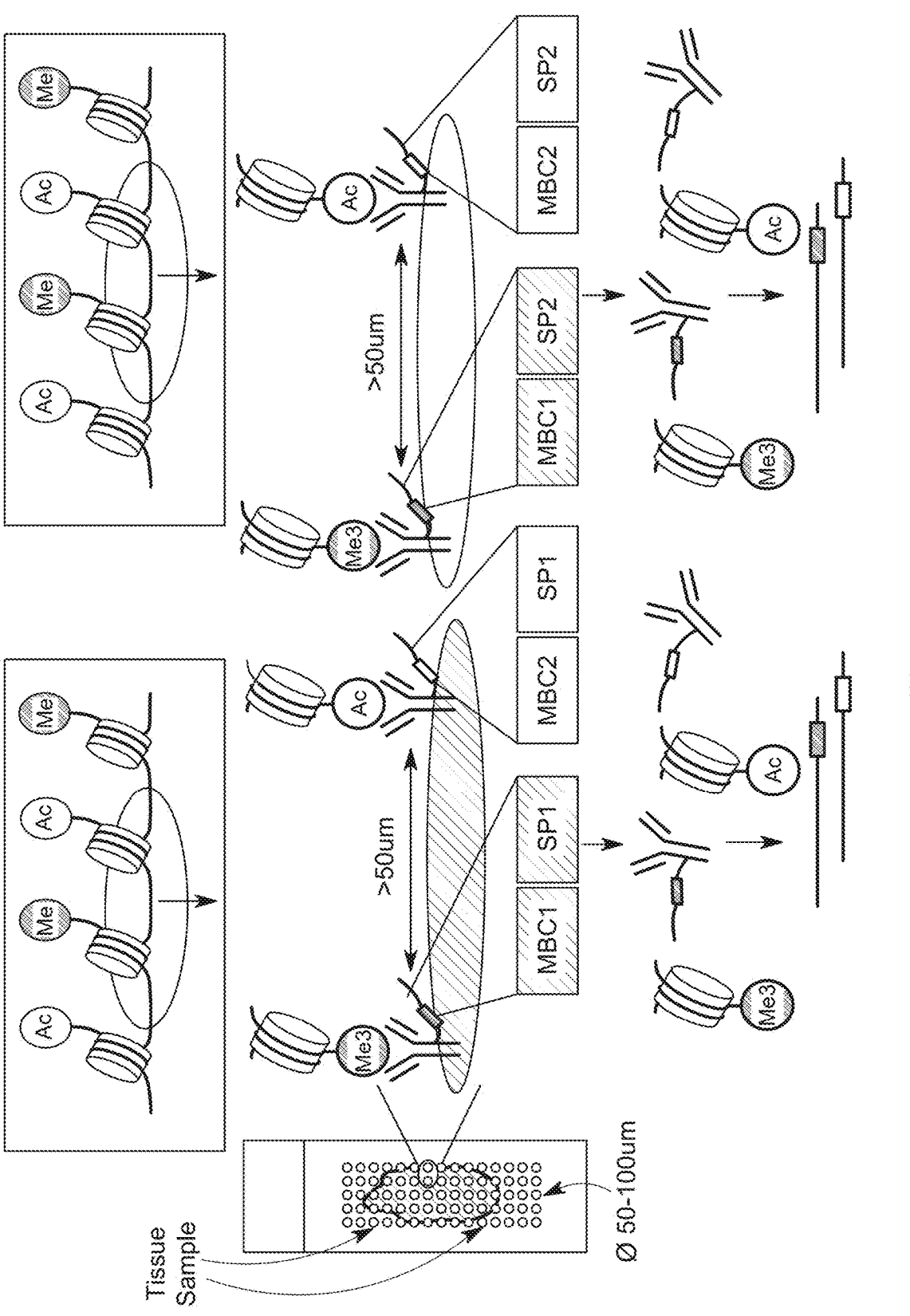
FIGS. 15A-15B shows the spatial analysis of histone modifications of the cells in a tissue. Nucleosome-binding conjugates comprising an adapter with a modification barcode and a spatial identifier sequence are spotted on a microarray slide. Transferring the adapter to the nucleosomes that are released from the tissue identifies the location of the nucleosome's origin cell of the tissue relative to the microarray. SP1 and SP2 are the spatial identifiers for spot 1 and spot 2 (FIG. 15A). Permeabilization of the cells in the tissue section is followed by chromatin digestion as shown in FIG. 15B.
Figure 15B:
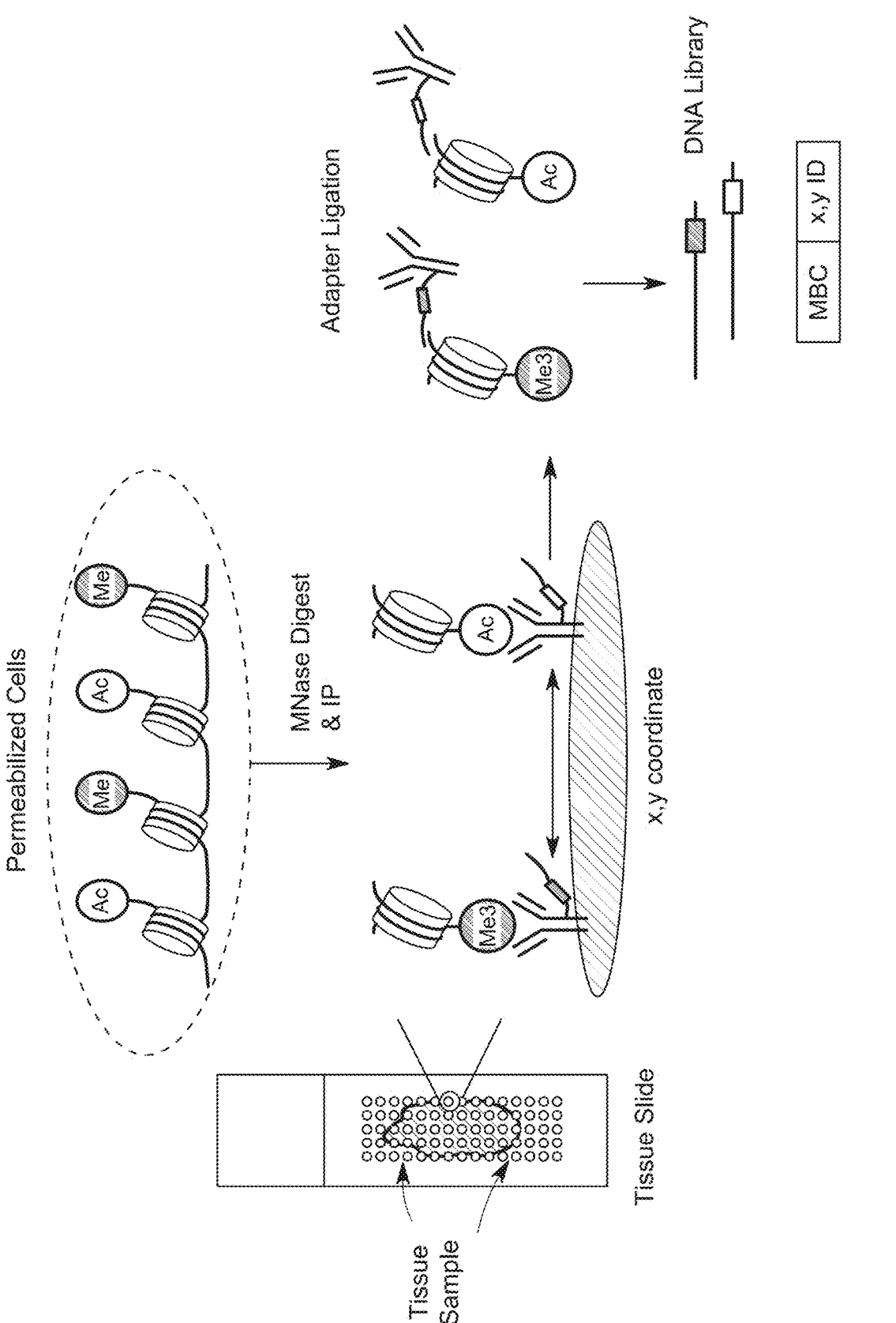

FIG. 13B depicts the associated enrichment values. FIG. 13C shows examples of sequencing reads indicative of two serial barcoding cycles. In summary, the data presented above validate the barcoding chemistry for serial barcoding cycles.

Example 8: Methods for Elution of Immunoprecipitated Nucleosomes from Bead Surface This example describes methods for eluting initially immunoprecipitated nucleosomes and associated DNA from bead surface. The elution of nucleosomes in an intact form where the associated DNA remained wrapped around histone octamers is essential to allow subsequent immunoprecipitation and barcoding of additional histone modifications that coexist within the same nucleosome. In this example, we tested the effectiveness of nucleosome elution by three approaches: a) competitive displacement of the nucleosome with modified histone peptide, b) competitive displacement of the antibody with protein G and c) elution with a high salt buffer.

Protein G magnetic beads were loaded with Ab43 (histone H3K9ac antibody, Active Motif, Cat #91103) or Ab67 (histone H3 antibody, Thermo Fisher, Cat #39064) following the manufacturer's protocol.

HeLa mononucleosome (EpiCypher Cat #16-0002) was spiked in with SNAP-ChIP® K-MetStat Panel (EpiCypher Cat #19-1001), SNAP-ChIP® K-AcylStat Panel (EpiCypher Cat #19-3001), and recombinant mononucleosomes H3K9ac (EPL, Active Motif, Cat #81075). The nucleosome mix was diluted with HBST300 and applied to Ab43 loaded protein G beads for immunoprecipitation at room temperature for one hour.

Immunoprecipitated nucleosomes were 5'phosphorylated by T4 Polynucleotide Kinase and 3'blunt-ended by T4 DNA polymerase, then 3'dA tailed by Klenow Fragment 3'->5' exo- as described in Example 7.

After end repair, immunoprecipitated nucleosomes were subjected to an excess amount of Histone Acetyl H3K9ac Peptide, Biotinylated (EpiGenTek, Cat #R-1010-100), and incubated at room temperature for 30 minutes to replace nucleosomes from antibody binding sites by competition. The supernatant containing the released nucleosomes was transferred to magnetic streptavidin beads and allowed to incubate for 15 minutes at room temperature to purify nucleosomes from excess biotinylated H3K9ac peptide. The supernatant was collected and ready for repeated immunoprecipitation on an Ab67 loaded protein A bead (H3 targeting).

In a separate reaction, immunoprecipitated nucleosomes were subjected to an excess amount of protein G molecules to displace the nucleosome and antibody complexes from the protein G beads. After 30 minutes incubation at room temperature, the supernatant containing the released nucleosome-antibody complexes was transferred to an Ab67 loaded protein A bead for repeated immunoprecipitation.

In a third reaction, immunoprecipitated nucleosomes were eluted by incubating in Gentle Ag/Ab Elution Buffer (Thermo Fisher, Cat #21027) at room temperature for 30 min. The supernatant containing the eluted nucleosome was diluted by 10 mM HEPES buffer, pH 7.5 before applying to an Ab67 loaded protein A bead for repeated immunoprecipitation.

A no elution control reaction was performed in parallel where Ab43 (targeting H3K9ac) immunoprecipitated nucleosomes were kept on protein G beads without eluting.

The no elution control bead and the remaining protein G beads after each nucleosome elution reaction from above were washed with HBST300 buffer and used as the input for capping step to ligate library adapters to nucleosome DNA.

The second immunoprecipitation reactions were allowed to proceed on Ab67 loaded protein A beads for one hour at room temperature, and washed with HBST300 buffer.

All beads prepared above underwent a capping step where universal sequencing adapter was attached to DNA ends for library amplification by PCR. The ligation reaction was induced by suspending the bead bound nucleosomes in ligation buffer (50 mM Tris-HCl pH 7.5, 150 mM NaCl, 10 mM MgCl2, 1 mM ATP, 10% PEG-8K, 0.05% Tween20, and 400 U T4 DNA ligase), supplemented with 0.5 uM of HP-U adapter, as described in Example 7. The adapter ligation reaction was incubated for 15 minutes at 20° C.-15 minutes at 25° C., then stopped by addition of EDTA and washing with HBST300 buffer. After the adapter ligation, the loop ends were separated to Y-shaped ends by cleavage with USER enzyme. Cleavage reaction was performed by incubating the beads with 0.5 units of USER enzyme in 1×NEB rCutSmart buffer for 15 minutes at 37° C. The reaction was washed by HBST300 buffer.

Library adapter ligated nucleosome DNA were subsequently eluted by incubating 0.12 units of thermolabile Proteinase K (New England Biolabs, Cat #P8111S) in a reaction mix consisting of RIPA buffer, supplement with 0.4% SDS and 5 mM DTT. The DNA elution reaction was allowed to proceed for one hour at 37° C., then for 10 minutes at 65° C. The elution was further purified by AMPure beads. The DNA was PCR amplified using Illumina index primers and the NEBNext Ultra II Q5 master mix (NEB) following the manufacturer's protocol. Indexed libraries were purified with AMPure beads, quantified by Qubit (Thermo Fisher). 2 μL of amplified libraries were accessed on 4% E-Gel™ EX Agarose Gel (Thermo Fisher, Cat #G401004) to examine efficiencies of nucleosome elution strategies (FIG. 14). Nucleosome elution was most efficient with gentle elution buffer (lanes 6 & 7), followed by elution with protein G (lanes 4 & 5) and elution with H3K9ac peptide was least efficient (lanes 2 & 3).

This example identifies gentle elution buffer as the best option for removing the nucleosome from a binding domain after a cycle of barcoding. The next step will be to integrate this step into the workflow described in example 7.

Example 9: A Method for Identifying the Spatial Distribution of a Histone Modification in a Tissue Sample This example describes the preparation of a microarray with spatially encoded nucleosome-binding conjugates and an end-to-end workflow for identifying H3K4me3 in a spatially resolved fashion.

An array with 96 spots is prepared wherein each spot features a nucleosome-binding conjugate with a unique spatial identifier and a modification barcode for H3K4me3. The nucleosome-binding conjugate is prepared using the SiteClick Antibody Azido Modification Kit (Thermo Fisher, cat. No. 520026) and Ab42 (histone H3K4me3 antibody, EpiCypher, cat #13-0041) and rcMBC101 /5Phos/GT-GATCGNNNNNCTGTCTCTTATACACATCTGACUT-TTTT (SEQ ID NO: 1)/DBCO, as described in Example 5. The array is a protein G-coated slide and each spot is prepared by the spontaneous immobilization of nucleosome-binding conjugate through the protein G-antibody interaction. Each spot has a unique spatial identifier determined by the barcode included in the conjugate spotted at that position on the slide.

A tissue section is prepared by cryosectioning in a cryostat and securely mounted on the microarray slide. The thickness of the tissue section may be 10-40 μm. To prevent dissociation of DNA binding proteins and nucleosome disassembly, the tissue section is brought to room temperature and is fixed with 0.2% formaldehyde for 5 minutes and quenched with 1.25 M glycine for 5 min at room temperature. The tissue is washed with a protease inhibitor-containing wash buffer, rinsed with DI water and then with isopropanol and air dried. To record the orientation of the tissue section relative to the microarray, standard haematoxylin and eosin (H&E) staining is performed. The hematoxylin stains cell nuclei a purplish blue, and eosin stains the extracellular matrix and cytoplasm pink, with other structures taking on different shades, hues, and combinations of these colors. The microarray with the H&E stained tissue section is imaged by light microscopy before proceeding to cell permeabilization.

The tissue section is then permeabilized with a NP40-Digitonin Wash Buffer. Next, the chromatin is digested with micrococcal nuclease (NEB) following the buffer recommendations of the supplier. After another wash in NP40-Digitonin Wash Buffer, the nucleosomes are captured by the immobilized nucleosome-binding conjugates and washed with RIPA buffer (see above). The ends of the nucleosomal DNA are repaired following the blunt end protocol described in Example 3. Blunt end ligation of the adapters is induced by suspending the surface bound nucleosomes in ligation buffer (50 mM Tris-HCl pH 7.5, 150 mM NaCl, 10 mM MgCl2, 1 mM ATP, 10% PEG-8K, 0.05% Tween20, and 400 U T4 DNA ligase), supplemented with 0.5 uM of each MBC101 (/5deoxyI//ideoxyI//ideoxyI/CGATCAC). Following barcoding, the adapter is released from the antibody by USER treatment (NEB), which cleaves the single uracil that is part of the adapter sequence. Complementary DNA strands are synthesized in a standard primer extension reaction with 8 units of Bst 3.0 DNA Polymerase in extension buffer (1 mM of each dNTP, 20 mM Tris-HCl, 10 mM (NH4)2SO4, 50 mM KCl, 2 mM MgSO4, 0.1% Tween® 20, pH 8.8® 25° C., 0.5 uM extension primer (GTCA-GATGTGTATAAGAGACAG; SEQ ID NO: 3) using the following thermocycler program: 72° C. 2 min-55° C. 5 min-65° C. 15 min-72° C. 5 min-80° C. 5 min-16° C. hold. The second sequencing adapter is introduced by repeating the same ligation step that was used for introducing the spatial MBC adapters in the presence of 100 units T4 DNA ligase and 10 units T4 Polynucleotide Kinase to phosphorylate the 5'ends of bead strands. The second adapter is universal and comprises only the Illumina P7 adapter (AGACGTGTGCTCTTCCGATCT; SEQ ID NO: 4) and its complement (GATCGGAAGAGC; SEQ ID NO: 5). The barcoded DNA is purified with Ampure beads and PCR amplified using the NEBNext Ultra II Q5 master mix (NEB) following the manufacturer's protocol. Indexed libraries were purified with AMPure beads, inspected on a 4% agarose gel, quantified by Qubit (Thermo Fisher) and sequenced. The result of this experiment is a sequencing library that spatially encodes the histone modification H3K4Me3 present in the tissue sample.

Numbered Aspects

Notwithstanding the appended claims, the following numbered aspects also form part of the instant disclosure and are also examples and representative species of the present invention.

1. A composition comprising:
   i) a substrate,
   ii) a binding domain coupled to the substrate, and
   iii) an adapter,
   wherein the binding domain binds to a DNA binding protein or a nucleosome comprising a histone modification,
   wherein the adapter comprises a nucleic acid barcode sequence unique to the histone modification or the DNA binding protein.

2. The composition of any one or combination of numbered aspects disclosed herein, wherein the substrate is a bead, a microarray, a chip, a flowcell, or a fluidics device.

3. The composition of any one or combination of numbered aspects disclosed herein, wherein the binding domain comprises an antibody, a scFv, a Fab fragment, a light chain of an antibody (VL), a heavy chain of an antibody (VH), a variable fragment (Fv), a F(ab')2 fragment, a diabody, a VHH domain, a nanobody, a bispecific antibody, a bivalent binding domain directed at two histone modifications, an aptamer, an engineered macromolecule scaffold, an engineered protein scaffold, or a selective covalent capture reagent, or a fragment or derivative thereof.

4. The composition of any one or combination of numbered aspects disclosed herein, wherein the binding domain comprises a histone modification reader protein, a writer protein, or an eraser protein.

5. The composition of any one or combination of numbered aspects disclosed herein, wherein the writer protein is a histone acetyltransferase, a lysine methyltransferase, an arginine methyltransferase.

6. The composition of any one or combination of numbered aspects disclosed herein, wherein the reader protein comprises a Methyl-CpG-binding domain (MBD), a bromodomain adjacent to the zinc finger proteins (BAZ) domain, a bromodomain (BRD), a malignant brain tumor (MBT) domain, a plant homeodomain finger (PHD) domain, a chromatin binding (chromo) domain, a proline-tryptophan-tryptophan-proline domain (PWWP) domain, a tryptophan-aspartic acid dipeptide repeat domain (WD40), or a tudor domain.

7. The composition of any one or combination of numbered aspects disclosed herein, wherein the eraser protein is a histone deacetylase, histone lysine demethylase, or a histone arginine demethylase.

8. The composition of any one or combination of numbered aspects disclosed herein, wherein the binding domain comprises a catalytically inactive variant of a histone modification writer or eraser protein.

9. The composition of any one or combination of numbered aspects disclosed herein, wherein the binding domain is coupled to the substrate covalently, via an affinity interaction, or a combination thereof.

10. The composition of any one or combination of numbered aspects disclosed herein, wherein the adapter is coupled to the substrate.

11. The composition of any one or combination of numbered aspects disclosed herein, wherein the adapter is coupled to the substrate covalently, or via an affinity interaction, or a combination thereof.

12. The composition of any one or combination of numbered aspects disclosed herein, wherein the adapter comprises at least one universal sequence element in addition to the barcode.

13. The composition of any one or combination of numbered aspects disclosed herein, wherein the adapter comprises a unique molecular identifier in addition to the barcode.

14. The composition any one or combination of numbered aspects disclosed herein, wherein the adapter comprises a spatial identifier sequence in addition to the barcode.

15. The composition of any one or combination of numbered aspects disclosed herein, wherein the adapter comprises uracil bases, inosine bases, 8-oxo-G bases, ribonucleosides, or a restriction sequence.

16. The composition of any one or combination of numbered aspects disclosed herein, wherein the adapter comprises a recognition sequence of a restriction enzyme, a 8-oxoguanine-DNA glycosylase, a uracil-DNA glycosylase (UDG), an endonuclease, or a ribonuclease.

17. The composition of any one or combination of numbered aspects disclosed herein, wherein the adapter comprises a substrate anchoring moiety.

18. The composition of any one or combination of numbered aspects disclosed herein, wherein the substrate anchoring moiety is biotin or desthiobiotin.

19. The composition of any one or combination of numbered aspects disclosed herein, wherein the substrate anchoring moiety is trans-cyclooctene (TCO), methyl-tetrazine (mTET), Dibenzocyclooctyl (DBCO), an azido or an alkyne.

20. The composition of any one or combination of numbered aspects disclosed herein, wherein the adapter is partially double-stranded forming a Y-shape, where the double-stranded portion is configured for ligation to the target nucleic acid and each single-stranded arm comprises universal sequences, a modification barcode, and a unique molecular identifier.

21. The composition of any one or combination of numbered aspects disclosed herein, wherein the adapter is partially double-stranded forming a hairpin comprising a stem region that is configured for ligation to the target nucleic acid and a single stranded loop, wherein the single-stranded loop comprises universal sequences, a modification barcode and a unique molecular identifier.

22. The composition of any one or combination of numbered aspects disclosed herein, wherein the adapter is partially double-stranded with a single-stranded 3' overhang.

23. The composition of any one or combination of numbered aspects disclosed herein, wherein the adapter is partially double-stranded with single-stranded 3' overhangs on both sides.

24. The composition of any one or combination of numbered aspects disclosed herein, where a double-stranded end is either a blunt end or has a single 3'-base overhang.

25. The composition of any one or combination of numbered aspects disclosed herein, wherein the histone modification is a methylation, citrullination, acetylation, ubiquitination, ADP ribosylation, deamination, proline isomerization, or sumoylation of lysine or arginine.

26. The composition of any one or combination of numbered aspects disclosed herein, wherein the histone modification is phosphorylation of tyrosine, serine, or threonine.

27. The composition of any one or combination of numbered aspects disclosed herein, wherein the DNA binding protein is a transcription factor or RNA polymerase II.

28. A method for analyzing a plurality of nucleosomes, the method comprising:
   (i) contacting a plurality of substrates comprising at least one composition of any one of any one or combination of numbered aspects disclosed herein with a solution comprising the plurality of nucleosomes, wherein the binding domain binds to a DNA binding protein or a nucleosome comprising a histone modification;
   (ii) ligating an adapter with the nucleic acid barcode to the target DNA of the nucleosome comprising the histone modification or DNA binding protein;
   (iii) introducing universal sequences for amplifying the target DNA;
   (iv) amplifying the barcoded target DNA; and
   (v) analyzing the amplified barcoded target DNA by sequencing.

29. A method for analyzing a plurality of nucleosomes, the method comprising:
   (i) contacting a plurality of substrates comprising at least one composition of any one of any one or combination of numbered aspects disclosed herein with a solution comprising the plurality of nucleosomes, wherein the binding domain binds to a DNA binding protein or a nucleosome comprising a histone modification;
   (ii) ligating an adapter with the nucleic acid barcode to the target DNA of the nucleosome comprising the histone modification or DNA binding protein;
   (iii) releasing the nucleosome from the substrate by cleaving the ligated adapter;
   (iv) repeating steps (i) through (iii) at least once;
   (v) introducing universal nucleic acid sequences for amplifying the target DNA;
   (vi) amplifying the barcoded target DNA; and
   (vii) analyzing the amplified barcoded target DNA by sequencing.

30. The method of any one or combination of numbered aspects disclosed herein, wherein steps (i) through (iii) are repeated at least twice.

31. The method of any one or combination of numbered aspects disclosed herein, wherein the releasing step comprises cleavage of the ligated adapter at a restriction site, uracil, inosine, an 8-oxoG or a ribonucleoside of the adapter by an enzyme that is specific for these bases.

32. The method of any one or combination of numbered aspects disclosed herein, wherein the releasing step comprises cleaving the recognition sequence of an adapter using a restriction enzyme, 8-oxoguanine-DNA glycosylase, a uracil-DNA glycosylase (UDG), an endonuclease, a ribonuclease, or derivative of any of these enzymes.

33. The method of any one or combination of numbered aspects disclosed herein, wherein steps (i) through (iii) are performed using two or more different types of substrates each comprising a different binding domain and adapter with a nucleic acid barcode.

34. The method of any one or combination of numbered aspects disclosed herein, wherein both the binding domain and the adapter are attached to the substrate covalently, via an affinity interaction, or a combination thereof.

35. The method of any one or combination of numbered aspects disclosed herein, comprising using a different binding domain and adapter each time steps (i)-(iii) are repeated.

36. A method for analyzing a plurality of nucleosomes, the method comprising:

(i) contacting one type of substrates comprising one composition of any one or combination of numbered aspects disclosed herein with a solution comprising the plurality of nucleosomes, wherein the binding domain binds to a DNA binding protein or a nucleosome comprising a histone modification;

(ii) adding an adapter to the plurality of nucleosomes bound to the binding domain;

(iii) ligating the adapter with the nucleic acid barcode to the target DNA of the nucleosome comprising the histone modification or DNA binding protein;

(iv) releasing the nucleosome from the binding domain by adding a buffer that disrupts the interaction between binding domain and nucleosome;

(v) repeating steps (i) to (iv) at least once;

(vi) introducing universal sequences for amplifying the target DNA;

(vii) amplifying the barcoded target DNA; and (viii) analyzing the amplified barcoded target DNA by sequencing.

37. The method of any one or combination of numbered aspects disclosed herein, wherein steps (i) through (iv) are repeated at least twice.

38. The method of any one or combination of numbered aspects disclosed herein, wherein ligating the adapter comprises a T4 DNA ligase, CircLigase, T3 DNA ligase, T7 DNA ligase, 9° N DNA Ligase, Taq DNA Ligase, or *E. coli* DNA ligase.

39. The method of any one or combination of numbered aspects disclosed herein, wherein the step of introducing the universal sequences comprises ligating to the adapter with the nucleic acid barcode to the target DNA a partially double-stranded Y-shape adaptor or a partially double-stranded bell-shaped adapter.

40. The method of any one or combination of numbered aspects disclosed herein, wherein the releasing step comprises adding a buffer comprising a reducing agent, an enzyme that specifically digests antibodies (e.g., papain and/or pepsin), a synthetic modified histone peptide that acts as a competitive binder, a surfactant (e.g., SDS, Sodium Deoxycholate), an acidic buffer with a pH of 6.5 or below, or an alkaline buffer with a pH of 8.5 or above, about 0.3 M to about 2 M NaCl, or about 0.5 M to about 1 M NaCl.

41. A nucleosome-binding conjugate comprising:

i) a binding domain, and ii) an adapter conjugated to the binding domain, wherein the binding domain binds to a DNA binding protein or a nucleosome comprising a histone modification, wherein the adapter comprises a nucleic acid barcode sequence unique to the histone modification or the DNA binding protein.

42. The nucleosome-binding conjugate of any one or combination of numbered aspects disclosed herein, where 1, 2, 3, 4, 5, 6, 7, 8, 9, 10, 11, 12, 13, 14, or 15 adapters are conjugated to the nucleosome-binding conjugate.

43. The nucleosome-binding conjugate of any one or combination of numbered aspects disclosed herein, wherein the binding domain comprises an antibody, a scFv, a Fab fragment, a light chain of an antibody (VL), a heavy chain of an antibody (VH), a variable fragment (Fv), a F(ab')2 fragment, a diabody, a VHH domain, a nanobody, a bispecific antibody, a bivalent binding domain directed at two histone modifications, an aptamer, an engineered macromolecule scaffold, an engineered protein scaffold, or a selective covalent capture reagent, or a fragment or derivative thereof.

44. The nucleosome-binding conjugate of any one or combination of numbered aspects disclosed herein, wherein the binding domain comprises a DNA or chromatin reader protein, a writer protein, or an eraser protein.

45. The nucleosome-binding conjugate of any one or combination of numbered aspects disclosed herein, wherein the writer protein is a DNA methyltransferase, a histone acetyltransferase, a lysine methyltransferase, or an arginine methyltransferase.

46. The nucleosome-binding conjugate of any one or combination of numbered aspects disclosed herein, wherein the reader comprises a MBD domain, a BAZ domain, a BRD domain, a MBT domain, a PHD domain, a chromo domain, a PWWP domain, a WD40 domain, or tudor domain.

47. The nucleosome-binding conjugate of any one or combination of numbered aspects disclosed herein, wherein the eraser protein is a methylcytosine dioxygenase, a histone deacetylase, or a histone lysine demethylase.

48. The nucleosome-binding conjugate of any one or combination of numbered aspects disclosed herein, wherein the binding domain comprises a catalytically inactive variant of a histone modification writer or eraser protein.

49. The nucleosome-binding conjugate of any one or combination of numbered aspects disclosed herein, wherein the adapter comprises a universal sequence in addition to the barcode.

50. The nucleosome-binding conjugate of any one or combination of numbered aspects disclosed herein, wherein the adapter comprises a unique molecular identifier in addition to the barcode.

51. The composition of any one or combination of numbered aspects disclosed herein, wherein the adapter comprises a spatial identifier sequence in addition to the barcode.

52. The nucleosome-binding conjugate of any one or combination of numbered aspects disclosed herein, wherein the adapter comprises uracil bases, inosine bases, 8-oxo-G bases, ribonucleosides, or a restriction sequence.

53. The nucleosome-binding conjugate of any one or combination of numbered aspects disclosed herein, wherein the adapter comprises a recognition sequence of a restriction enzyme, 8-oxoguanine-DNA glycosylase, an uracil-DNA glycosylase (UDG), an endonuclease, a ribonuclease, or derivative of any of these enzymes.

54. The nucleosome-binding conjugate of any one or combination of numbered aspects disclosed herein, wherein the adapter is partially double-stranded forming a Y-shape, where the double-stranded portion is configured for ligation to the target nucleic acid and each single-stranded arm may comprise universal sequences, a modification barcode, a unique molecular identifier, and optionally a spatial identifier sequence.

55. The nucleosome-binding conjugate of any one or combination of numbered aspects disclosed herein, wherein the adapter is partially double-stranded forming a hairpin comprising a stem region that is configured for ligation to the target nucleic acid and a single stranded loop, wherein the single-stranded loop comprises universal sequences, a modification barcode, a unique molecular identifier, and optionally a spatial identifier sequence.

56. The nucleosome-binding conjugate of any one or combination of numbered aspects disclosed herein, wherein the adapter is partially double-stranded with a single-stranded 3'overhang.

57. The nucleosome-binding conjugate of any one or combination of numbered aspects disclosed herein, wherein the adapter is partially double-stranded with single-stranded 3'overhangs on both sides.

58. The nucleosome-binding conjugate of any one or combination of numbered aspects disclosed herein, where a double-stranded end is either a blunt end or has a single 3'-base overhang.

59. The nucleosome-binding conjugate of any one or combination of numbered aspects disclosed herein, wherein the histone modification is methylation, citrullination, acetylation, ubiquitination, ADP ribosylation, proline isomerization, or sumoylation of lysine or arginine.

60. The nucleosome-binding conjugate of any one or combination of numbered aspects disclosed herein, wherein the histone modification is phosphorylation of tyrosine, serine, and threonine.

61. The nucleosome-binding conjugate of any one or combination of numbered aspects disclosed herein, wherein the DNA binding protein is a transcription factor or RNA polymerase II.

62. A method for analyzing a plurality of nucleosomes, the method comprising:

(i) contacting a solution comprising the plurality of nucleosomes with a solution comprising at least one nucleosome-binding conjugate of any one of any one or combination of numbered aspects disclosed herein, wherein the binding domain binds to a DNA binding protein or a nucleosome comprising a histone modification;

(ii) ligating an adapter with the nucleic acid barcode of the nucleosome-binding conjugate to the target DNA of the nucleosome comprising the histone modification or DNA binding protein to produce barcoded target DNA in an environment wherein generation of off-target barcoded DNA is less than 20% of the barcoded target DNA;

(iii) introducing universal sequences for amplifying the target DNA;

(iv) amplifying the barcoded target DNA; and (v) analyzing the amplified barcoded target DNA by sequencing.

63. The method of any one or combination of numbered aspects disclosed herein, comprising transferring the adapters of one or two nucleosome-binding conjugates to the same target DNA.

64. The method of any one or combination of numbered aspects disclosed herein, comprising transferring the adapters of two nucleosome-binding conjugates to the same target DNA.

65. The method of any one or combination of numbered aspects disclosed herein, comprising limiting the off-target barcoding by performing the ligating step in a micromolar, nanomolar, picomolar, femtomolar, attomolar, or zeptomolar solution of nucleosome and nucleosome-binding conjugate.

66. A method for analyzing a plurality of nucleosomes, the method comprising:

(i) immobilizing a plurality of nucleosomes on a substrate at a spacing wherein off-target barcoding is less than 20%;

(ii) contacting the immobilized nucleosomes with a solution comprising at least one nucleosome-binding conjugate of any one of any one or combination of numbered aspects disclosed herein, wherein the binding domain binds to a DNA binding protein or a nucleosome comprising a histone modification;

(iii) ligating an adapter with the nucleic acid barcode of the nucleosome-binding conjugate to the target DNA of the nucleosome comprising the histone modification or DNA binding protein;

(iv) cleaving the adapter such that a nucleic acid end is generated with the structure suitable for ligation to other adapters;

(v) repeating steps (ii) through (iv) at least once;

(vi) introducing universal nucleic acid sequences for amplifying the target DNA;

(vii) amplifying the barcoded target DNA; and (viii) analyzing the amplified barcoded target DNA by sequencing.

67. The method of any one or combination of numbered aspects disclosed herein, wherein steps (ii) through (iv) are repeated at least two times.

68. The method of any one or combination of numbered aspects disclosed herein, comprising limiting off-target barcoding by immobilizing the nucleosomes on a substrate at a spacing distance of 50 nm or more, e.g., 50, 55, 60, 65, 70, 75, 80, 85, 90, 95, 100, 50-500, 50-400, 50-300, 50-250, 50-200, 50-100, or any integer, value or range between 50 and 1000 nm.

69. The method of any one or combination of numbered aspects disclosed herein, comprising cleaving the adapter at an uracil, an inosine, an 8-oxoG, or a ribonucleoside of the adapter by an enzyme that is specific for the uracil, the inosine, the 8-oxoG, or the ribonucleoside of the adapter.

70. The method of any one or combination of numbered aspects disclosed herein, comprising cleaving the recognition sequence of an adapter using a restriction enzyme.

71. The method of any one or combination of numbered aspects disclosed herein, wherein the adapter comprises a recognition sequence of a restriction enzyme, 8-oxoguanine-DNA glycosylase, a uracil-DNA glycosylase (UDG), endonuclease, or a ribonuclease.

72. The method of any one or combination of numbered aspects disclosed herein, comprising using a different binding domain and adapter each time steps (ii)-(iv) are repeated.

73. The method of any one or combination of numbered aspects disclosed herein, wherein ligating comprises using a T4 DNA ligase, CircLigase, T3 DNA ligase, T7 DNA ligase, 9° N DNA Ligase, Taq DNA Ligase, or *E. coli* DNA ligase.

74. A method for analyzing a plurality of nucleosomes in the context of a tissue, the method comprising:

(i) immobilizing a plurality of nucleosome-binding conjugates on a planar microarray substrate at a spacing wherein off-target barcoding is less than about 20%;

(ii) layering a tissue section on top of the planar microarray substrate comprising the plurality of nucleosome-binding conjugates;

(iii) permeabilizing the tissue cells;

(iv) digesting the chromatin with endonuclease and capturing the nucleosomes by the immobilized nucleosome-binding conjugates;

(v) ligating an adapter with the nucleic acid barcode and a spatial identifier sequence of the nucleosome-binding conjugate to the target DNA of the nucleosome comprising the histone modification or DNA binding protein to produce barcoded target DNA in an environment wherein generation of off-target barcoded DNA is less than 20% of the barcoded target DNA;

(vi) introducing universal sequences for amplifying the target DNA;

(vii) amplifying the barcoded target DNA;

(vii) analyzing the amplified barcoded target DNA by sequencing; and (viii) determining the identity of the histone modification or DNA binding protein and their spatial location on the planar microarray substrate based on the barcode and the spatial identifier sequence.

75. The method of any one of any one or combination of numbered aspects disclosed herein, comprising limiting the off-target barcoding by immobilizing the nucleosomes or the nucleosome-binding conjugates on a substrate at a spacing distance of 50 nm or more.

76. A method for analyzing a plurality of nucleosomes, the method comprising:

(i) introducing a universal connector to the target DNA of the nucleosome;

(ii) contacting a solution comprising the plurality of nucleosomes with a solution comprising at least one nucleosome-binding conjugate of any one of any one or combination of numbered aspects disclosed herein, wherein the binding domain binds to a DNA binding protein or a nucleosome comprising a histone modification;

(iii) connecting the adapters of the bound plurality of nucleosome-binding conjugates by ligation;

(iv) hybridizing the universal connector of the target DNA to the 3'end of the ligated adapters;

(v) copying the sequence of the ligated adapters to produce a copy of barcoded target DNA;

(vi) introducing universal nucleic acid sequences for amplifying the target DNA;

(vii) amplifying the barcoded nucleosome DNA, and (viii) analyzing the barcoded target DNA by sequencing.

77. The method of any one or combination of numbered aspects disclosed herein, wherein introducing the universal sequences comprises ligating a forward or reverse sequencing adapter to the barcode.

78. The method of any one or combination of numbered aspects disclosed herein, wherein the binding domain of the nucleosome-binding conjugate is linked to an internal position of the nucleic acid adapter.

79. The method of any one or combination of numbered aspects disclosed herein, comprising A-tailing the nucleosome in step (i).

80. The method of any one or combination of numbered aspects disclosed herein, comprising ligating a universal connector sequence in step (i).

81. The method of any one or combination of numbered aspects disclosed herein, comprising connecting the adapters of the bound plurality of nucleosome-binding conjugates by double-stranded, single-stranded, or splint ligation.

82. The methods of any one or combination of numbered aspects disclosed herein, wherein amplifying the barcoded target DNA comprises generating substrate-tethered colonies of monoclonal copies of the target DNA by surface amplification.

83. The methods of any one or combination of numbered aspects disclosed herein, wherein analyzing the amplified barcoded target DNA comprises in situ sequencing of substrate-tethered colonies of monoclonal copies of the target DNA.

84. The methods of any one or combination of numbered aspects disclosed herein, where analyzing the barcoded target DNA comprises analyzing the barcoded DNA by nucleic acid probe hybridization.

85. The methods of any one or combination of numbered aspects disclosed herein, where analyzing the barcoded target DNA comprises analyzing the barcoded DNA by PCR.

86. The methods of any one or combination of numbered aspects disclosed herein, comprising obtaining the nucleosome from a cell free circulating nucleosome.

87. The methods of any one or combination of numbered aspects disclosed herein, comprising obtaining the nucleosome from chromatin by enzymatic or mechanical shearing.

88. The methods of any one or combination of numbered aspects disclosed herein, comprising obtaining the nucleosome from single cells.

89. A method for diagnosing a cancer or cancer sub-type associated with one or more types of histone modifications, comprising analyzing a plurality of nucleosomes according to any one or combination of numbered aspects disclosed herein.

90. A method of monitoring the progression or treatment response of a cancer, comprising analyzing a plurality of nucleosomes according to any one or combination of numbered aspects disclosed herein.

91. The method of any one or combination of numbered aspects disclosed herein, comprising obtaining the plurality of nucleosomes from a blood sample.

92. The method of any one or combination of numbered aspects disclosed herein, comprising obtaining the plurality of nucleosomes from a tissue biopsy sample.

93. A kit for monitoring epigenetic changes over time in a sample obtained from a subject undergoing a treatment, comprising the composition of any one or combination of numbered aspects disclosed herein or the nucleosome binding conjugate of any one or combination of numbered aspects disclosed herein and instructions for using the composition or nucleosome binding conjugate for monitoring epigenetic changes over time.

94. The kit of any one or combination of numbered aspects disclosed herein, wherein the subject is being treated for cancer.

---

We claim:

1. A method for analyzing a plurality of nucleosomes, the method comprising:
   (i) contacting a composition with a solution comprising the plurality of nucleosomes, the composition comprising:
      a substrate,
      a binding domain coupled to the substrate, and
      an adapter,
      wherein the binding domain binds to a DNA binding protein or a nucleosome comprising a histone modification,
      wherein the adapter comprises a nucleic acid barcode sequence unique to the histone modification or the DNA binding protein,
   (ii) ligating the adapter comprising the nucleic acid barcode to a target DNA of the nucleosomes;
   (iii) introducing universal sequences for amplifying the target DNA;
   (iv) amplifying the barcoded target DNA to obtain amplified barcoded target DNA; and
   (v) analyzing the amplified barcoded target DNA by sequencing.

2. The method of claim 1, wherein after step (ii), further comprising (iia) releasing the nucleosomes from the substrate by cleaving the ligated adapter; and (iib) repeating steps (i) through (iia) at least once before performing step (iii).

3. The method of claim 2, wherein the steps (i) through (iia) are performed using one or more different types of substrates each comprising a different binding domain and adapter comprising the nucleic acid barcode; and/or using a different binding domain and adapter each time the contacting through the releasing steps are repeated.

4. The method of claim 2, wherein the releasing step (iia) comprises cleavage of the ligated adapter at a restriction site, uracil, inosine, an 8-oxoG or a ribonucleoside of the adapter by an enzyme that is specific for these bases, optionally in the presence of a second enzyme that cleaves abasic sites.

5. The method of claim 1, wherein prior to step (ii) adding the adapter to the plurality of nucleosomes bound to the binding domain; wherein after step (ii), step (iia) releasing the nucleosomes from the binding domain by adding a buffer that disrupts the interaction between binding domain and nucleosome; and (iib) repeating the steps (i) through (iia) at least once before performing step (iii).

6. The method of claim 5, wherein ligating the adapter comprises use of a T4 DNA ligase, CircLigase, T3 DNA ligase, T7 DNA ligase, 9°N DNA Ligase, Taq DNA Ligase, or E. coli DNA ligase.

7. The method of claim 5, wherein the step of introducing the universal sequences comprises ligating to the adapter a partially double-stranded Y-shape adaptor or a partially double-stranded bell-shaped adapter.

8. The method of claim 5, wherein the releasing step (iia) comprises adding a buffer comprising a reducing agent, an enzyme that specifically digests antibodies, a synthetic modified histone peptide that acts as a competitive binder, a surfactant, an acidic buffer with a pH of 6.5 or below, or an alkaline buffer with a pH of 8.5 or above, about 0.3 M to about 2 M NaCl, or about 0.5 M to about 1 M NaCl.

9. The method of claim 1, wherein the binding domain comprises an antibody, a scFv, a Fab fragment, a light chain of an antibody (VL), a heavy chain of an antibody (VH), a variable fragment (Fv), a F(ab')2 fragment, a diabody, a VHH domain, a nanobody, a bispecific antibody, a bivalent binding domain directed at two histone modifications, an aptamer, an engineered macromolecule scaffold, an engineered protein scaffold, or a selective covalent capture reagent; or wherein the binding domain comprises a histone modification reader protein, a writer protein, or an eraser protein.

10. The method of claim 9, wherein the writer protein is a histone acetyltransferase, a lysine methyltransferase, an arginine methyltransferase;

wherein the reader protein comprises a Methyl-CpG-binding domain (MBD), a bromodomain adjacent to the zinc finger proteins (BAZ) domain, a bromodomain (BRD), a malignant brain tumor (MBT) domain, a plant homeodomain finger (PHD) domain, a chromatin binding (chromo) domain, a proline-tryptophan-tryptophan-proline domain (PWWP) domain, a tryptophan-aspartic acid dipeptide repeat domain (WD40), or a tudor domain; and/or wherein the eraser protein is a histone deacetylase, histone lysine demethylase, or a histone arginine demethylase.

11. The method of claim 1, wherein the binding domain comprises a catalytically inactive variant of a histone modification writer or eraser protein.

12. The method of claim 1, wherein the adapter comprises at least one universal sequence element in addition to the barcode; wherein the adapter comprises a unique molecular identifier in addition to the barcode; wherein the adapter comprises a spatial identifier sequence in addition to the barcode; wherein the adapter comprises uracil bases, inosine bases, 8-oxo-G bases, ribonucleosides, or a restriction sequence; wherein the adapter comprises a recognition sequence of a restriction enzyme, a 8-oxoguanine-DNA glycosylase, a uracil-DNA glycosylase (UDG), an endonuclease, or a ribonuclease; and/or wherein the adapter comprises a substrate anchoring moiety.

13. The method of claim 12, wherein the substrate anchoring moiety is biotin or desthiobiotin; or wherein the substrate anchoring moiety is trans-cyclooctene (TCO), methyltetrazine (mTET), Dibenzocyclooctyl (DBCO), an azido or an alkyne.

14. The method of claim 1, wherein the adapter is partially double-stranded forming a Y-shape, where the double-stranded portion is configured for ligation to the target nucleic acid and each single-stranded arm comprises universal sequences, a modification barcode, and a unique molecular identifier; and/or wherein the adapter is partially double-stranded forming a hairpin comprising a stem region that is configured for ligation to the target nucleic acid and a single stranded loop, wherein the single-stranded loop comprises universal sequences, a modification barcode and a unique molecular identifier.

15. The method of claim 1, wherein the histone modification is a methylation, citrullination, acetylation, ubiquitination, ADP ribosylation, deamination, proline isomerization, or sumoylation of lysine or arginine; and/or wherein the histone modification is phosphorylation of tyrosine, serine, or threonine.

16. A method for analyzing a plurality of nucleosomes, the method comprising:

(i) contacting a solution comprising the plurality of nucleosomes with a composition comprising a nucleosome-binding conjugate comprising:
   a binding domain, and
   an adapter conjugated to the binding domain,
   wherein the binding domain binds to a DNA binding protein or a nucleosome comprising a histone modification, wherein the adapter comprises a nucleic acid barcode unique to the histone modification or the DNA binding protein, (ii) ligating the adapter with the nucleic acid barcode of the nucleosome-binding conjugate to a target DNA of the nucleosomes comprising a histone modification or a DNA binding protein to produce barcoded target DNA in an environment wherein generation of off-target barcoded DNA is less than 20% of the barcoded target DNA;

(iii) introducing universal sequences for amplifying the target DNA;

(iv) amplifying the barcoded target DNA; and (v) analyzing the amplified barcoded target DNA by sequencing.

17. The method of claim 16, comprising transferring the adapters of one or two nucleosome-binding conjugates to the same target DNA.

18. The method of claim 16, comprising limiting the off-target barcoding by performing the ligating step in a micromolar, nanomolar, picomolar, femtomolar, attomolar, or zeptomolar solution of nucleosome and nucleosome-binding conjugate.

19. The method of claim 16, wherein prior to step (i) immobilizing a plurality of nucleosomes on a substrate at a spacing wherein off-target barcoding is less than 20%; and/or prior to step (iii) cleaving the adapter such that a nucleic acid end is generated with the structure suitable for ligation to other adapters, wherein the immobilizing step through the cleaving step are repeated at least once.

20. The method of claim 19, comprising limiting off-target barcoding by immobilizing the nucleosomes on a substrate at a spacing distance of 50 nm or more.

21. The method of claim 19, wherein the method comprises cleaving the adapter at an uracil, an inosine, an 8-oxoG, or a ribonucleoside of the adapter by an enzyme that is specific for the uracil, the inosine, the 8-oxoG, or the ribonucleoside of the adapter; and/or wherein the method comprises cleaving the recognition sequence of an adapter using a restriction enzyme.

22. The method of claim 19, wherein the adapter comprises a recognition sequence of a restriction enzyme, 8-oxoguanine-DNA glycosylase, a uracil-DNA glycosylase (UDG), endonuclease, or a ribonuclease.

23. The method of claim 19, comprising using a different binding domain and adapter each time the contacting through the cleaving steps is repeated.

24. A method for analyzing a plurality of nucleosomes, the method comprising:

(i) introducing a universal connector to a target DNA of the nucleosome;

(ii) contacting a solution comprising the plurality of nucleosomes with a composition comprising a plurality of nucleosome-binding conjugates each comprising:
   a binding domain, and
   an adapter conjugated to the binding domain;
   wherein the binding domain binds to a DNA binding protein or a nucleosome comprising a histone modification, and
   wherein the adapter comprises a nucleic acid barcode sequence unique to the histone modification or the DNA binding protein, (iii) connecting the adapters by ligation to produce ligated adapters;

(iv) hybridizing the universal connector of the target DNA to a 3'end of the ligated adapters;

(v) copying the sequence of the ligated adapters to produce a copy of barcoded target DNA;

(vi) introducing universal nucleic acid sequences for amplifying the target DNA;

(vii) amplifying the barcoded nucleosome DNA, and (viii) analyzing the barcoded target DNA by sequencing.

25. The method claim 24, wherein introducing the universal sequences comprises ligating a forward or reverse sequencing adapter to the barcode.

26. The method of claim 24, wherein the binding domain of the nucleosome-binding conjugate is linked to an internal position of the nucleic acid adapter.

27. The method of claim 24, comprising A-tailing the nucleosomes in step (i).

28. The method of claim 24, comprising ligating a universal connector sequence in step (i).

29. The method of claim 24, comprising connecting the adapters of the bound plurality of nucleosome-binding conjugates by double-stranded, single-stranded, or splint ligation.

30. The methods of claim 24, wherein the nucleosome is obtained as a cell free circulating nucleosome from the blood of a subject.

\*    \*    \*    \*    \*